US012485171B2

(12) United States Patent
Singh et al.

(10) Patent No.: US 12,485,171 B2
(45) Date of Patent: *Dec. 2, 2025

(54) METHODS OF DISEASE ACTIVITY PROFILING FOR PERSONALIZED THERAPY MANAGEMENT

(71) Applicant: PROMETHEUS LABORATORIES INC., San Diego, CA (US)

(72) Inventors: Sharat Singh, Rancho Santa Fe, CA (US); Nicholas Hoe, San Diego, CA (US); Steve Lockton, San Diego, CA (US); Scott Hauenstein, San Diego, CA (US); Linda Ohrmund, San Diego, CA (US)

(73) Assignee: PROMETHEUS LABORATORIES INC., San Diego, CA (US)

( * ) Notice: Subject to any disclaimer, the term of this patent is extended or adjusted under 35 U.S.C. 154(b) by 343 days.

This patent is subject to a terminal disclaimer.

(21) Appl. No.: 17/484,786

(22) Filed: Sep. 24, 2021

(65) Prior Publication Data

US 2022/0096629 A1 Mar. 31, 2022

Related U.S. Application Data

(63) Continuation of application No. 16/112,242, filed on Aug. 24, 2018, now Pat. No. 11,160,863, which is a continuation of application No. 14/072,746, filed on Nov. 5, 2013, now Pat. No. 10,086,072, which is a continuation of application No. PCT/US2012/037375, filed on May 10, 2012.

(60) Provisional application No. 61/636,575, filed on Apr. 20, 2012, provisional application No. 61/566,509, filed on Dec. 2, 2011, provisional application No. 61/553,909, filed on Oct. 31, 2011, provisional application No. 61/505,026, filed on Jul. 6, 2011, provisional application No. 61/484,607, filed on May 10, 2011.

(51) Int. Cl.

*A61K 39/395* (2006.01)
*C12Q 1/6883* (2018.01)
*G01N 33/68* (2006.01)

(52) U.S. Cl.

CPC ........ *A61K 39/3955* (2013.01); *C12Q 1/6883* (2013.01); *G01N 33/6893* (2013.01); *C12Q 2600/106* (2013.01); *C12Q 2600/156* (2013.01); *C12Q 2600/158* (2013.01); *G01N 2800/065* (2013.01)

(58) Field of Classification Search

CPC ............. A61K 39/3955; C12Q 1/6883; G01N 33/6893

See application file for complete search history.

(56) References Cited

U.S. PATENT DOCUMENTS

| | | | |
|---|---|---|---|
| 5,674,754 | A | 10/1997 | Ahrens et al. |
| 6,319,899 | B1 | 11/2001 | Schwartz |
| 7,252,971 | B2 | 8/2007 | Benson et al. |
| 7,932,372 | B2 | 4/2011 | Pullen et al. |
| 8,012,698 | B2 | 9/2011 | Stephens et al. |
| 8,165,819 | B2 | 4/2012 | Clermont et al. |
| 8,293,489 | B2 | 10/2012 | Henkin |
| 8,538,774 | B2 | 9/2013 | Michelson et al. |
| 8,630,810 | B2 | 1/2014 | Clermont et al. |
| 9,732,385 | B2 | 8/2017 | Barken et al. |
| 10,086,072 | B2 | 10/2018 | Singh et al. |
| 11,162,943 | B2 | 11/2021 | Jain et al. |
| 2002/0025553 | A1 | 2/2002 | Wei |
| 2003/0087285 | A1 | 5/2003 | Chow et al. |
| 2004/0197304 | A1 | 10/2004 | Chen et al. |
| 2005/0154536 | A1 | 7/2005 | Chow et al. |
| 2006/0216239 | A1 | 9/2006 | Zhang et al. |
| 2008/0086272 | A1 | 4/2008 | Fillet |
| 2008/0162101 | A1 | 7/2008 | Sarna et al. |
| 2008/0228456 | A1 | 9/2008 | Clermont et al. |
| 2009/0156418 | A1 | 6/2009 | Blank et al. |
| 2010/0255513 | A1 | 10/2010 | Denson et al. |
| 2011/0045476 | A1 | 2/2011 | Barken et al. |
| 2011/0059445 | A1 | 3/2011 | Rutgeerts et al. |
| 2012/0046197 | A1 | 2/2012 | Glezer et al. |

(Continued)

FOREIGN PATENT DOCUMENTS

| | | | |
|---|---|---|---|
| CA | 2772916 | A1 | 3/2011 |
| CN | 1764838 | A | 4/2006 |

(Continued)

OTHER PUBLICATIONS

Algaba et al.: Relationship between levels of angiogenic and lymphangiogenic factors and the endoscopic, histological and clinical activity, and acute-hase reactants in patients with inflammatory bowel disease. J Crohns Colitis. 7(11:e569-79 (2013).
Baugh et al.: Matrix metalloproteinase levels are elevated in inflammatory bowel disease. Gastroenterology. 117:814-822 (1999).
Breiman et al.: Chapter 6 Medical diagnosis and prognosis. Classification and regression trees. Chappman & Hall/CRC (1984) (pp. 174-346).
BREIMAN: Random Forests. Machine Learning, 45; 5-32 (2001) http://stat-www.berkeley.edu/users/breiman/RandomForests/cc_home.htm.

(Continued)

*Primary Examiner* — Jerry Lin
(74) *Attorney, Agent, or Firm* — Greenberg Traurig, LLP

(57) ABSTRACT

The present invention provides methods for personalized therapeutic management of a disease in order to optimize therapy and/or monitor therapeutic efficacy. In particular, the present invention comprises measuring an array of one or a plurality of biomarkers at a plurality of time points over the course of therapy with a therapeutic agent to determine a mucosal healing index for selecting therapy, optimizing therapy, reducing toxicity, and/or monitoring the efficacy of therapeutic treatment. In certain instances, the therapeutic agent is a TNFα inhibitor for the treatment of a TNFα-mediated disease or disorder.

18 Claims, 35 Drawing Sheets

(56) References Cited

U.S. PATENT DOCUMENTS

| | | | |
|---|---|---|---|
| 2013/0071860 | A1 | 3/2013 | Hale et al. |
| 2013/0224210 | A1 | 8/2013 | Adamkewicz et al. |
| 2013/0273566 | A1 | 10/2013 | Denson et al. |
| 2014/0113306 | A1 | 4/2014 | Haimovich et al. |
| 2014/0141983 | A1 | 5/2014 | Singh et al. |
| 2014/0236166 | A1 | 8/2014 | Park et al. |
| 2014/0329721 | A1 | 11/2014 | Joern et al. |
| 2014/0356882 | A1 | 12/2014 | Moses et al. |
| 2015/0072879 | A1 | 3/2015 | Princen et al. |
| 2015/0301055 | A1 | 10/2015 | Spetzler |
| 2015/0355195 | A1 | 12/2015 | Singh et al. |
| 2017/0360926 | A1 | 12/2017 | Rosario et al. |
| 2017/0368027 | A1 | 12/2017 | Blum-Sperisen et al. |
| 2018/0086833 | A1 | 3/2018 | Hassanali et al. |
| 2019/0060449 | A1 | 2/2019 | Singh et al. |
| 2022/0082563 | A1 | 3/2022 | Jain |

FOREIGN PATENT DOCUMENTS

| | | | |
|---|---|---|---|
| CN | 1839157 | A | 9/2006 |
| CN | 101291693 | A | 10/2008 |
| CN | 101472611 | A | 7/2009 |
| EP | 1725876 | B1 | 5/2009 |
| JP | 2006521537 | A | 9/2006 |
| RU | 2141332 | C1 | 11/1999 |
| WO | WO-2004090539 | A2 | 10/2004 |
| WO | WO-2005000897 | A2 | 1/2005 |
| WO | WO-2005009339 | A2 | 2/2005 |
| WO | WO-2007050607 | A2 | 5/2007 |
| WO | WO-2007149814 | A1 | 12/2007 |
| WO | WO-2008036802 | A2 | 3/2008 |
| WO | WO-2009012140 | A2 | 1/2009 |
| WO | WO-2009108637 | A1 | 9/2009 |
| WO | WO-2010025340 | A2 | 3/2010 |
| WO | WO-2010132723 | A1 | 11/2010 |
| WO | WO-2010151699 | A1 | 12/2010 |
| WO | WO-2011008990 | A1 | 1/2011 |
| WO | WO-2011050069 | A1 | 4/2011 |
| WO | WO-2011066458 | A2 | 6/2011 |
| WO | WO-2011153501 | A2 | 12/2011 |
| WO | WO-2012088337 | A1 | 6/2012 |
| WO | WO-2012119113 | A2 | 9/2012 |
| WO | WO-2012154987 | A1 | 11/2012 |
| WO | WO-2013033623 | A1 | 3/2013 |
| WO | WO-2014054013 | A1 | 4/2014 |
| WO | WO-2015110989 | A1 | 7/2015 |
| WO | WO-2018220588 | A1 | 12/2018 |
| WO | WO-2020117795 | A1 | 6/2020 |

OTHER PUBLICATIONS

Carman et al.: Clinical disease activity and endoscopic severity correlate poorly in children newly diagnosed with Crohn's disease. Gastrointest Endosc. 89(2):364-372 (2019).

Chambers et al.: Serum amyloid A protein compared with C-reactive protein, alpha 1-antichymotrypsin and alpha 1-acid glycoprotein as a monitor of inflammatory bowel disease. European Journal of Clinical Investigation. 17(5):460-467 (1987).

Christensen et al.: Understanding endoscopic disease activity in IBD: how to incorporate it into practice. Curr Gastroenterol Rep. 18(1):5 (2016).

Daperno et al.: Results of the 2nd part scientific workshop of the ECCO (II): Measures and markers of prediction to achieve, detect, and monitor intestinal healing in inflammatory bowel disease. Journal of Crohn's and Colitis. 5:484-498 (2011).

Daperno et al.: Development and validation of a new, simplified endoscopic activity score for Crohn's disease: the SES-CD. Gastrointestinal Endoscopy. 60(4):505-512 (2004).

Dave et al.: Mucosal healing in inflammatory bowel disease—A true paradigm of success?. Gastroenterology & Hepatology. 8(1):29-38 (2012).

De Bruyn et al.: Biomarker Panel for Prediction of Mucosal Healing in Patients With Crohn's Disease Under Infliximab Therapy. Biosciences Information Service (2014).

D'Haens et al.: Development and Validation of a Test to Monitor Endoscopic Activity in Patients with Crohn's Disease Based on Serum Levels of Proteins. Gastroenterology. vol. Pii:S0016-5085(19)41525-4 (2019).

Disabatino et al.: Stromelysin-1 and macrophage metalloelastase expression in the intestinal mucosa of Crohn's disease patients treated with infliximab. European Journal of Gastroenterology and Hepatology. 21(9):1049-55 (2009).

Efsen et al.: Ramiprilate Inhibits Functional Matrix Metalloproteinase Activity in Crohn's Disease Fistulas. Basic and Clinical Pharmacy and Toxicology. 109(3):208-216 (2011).

Epstein et al.: Curcumin suppresses p38 mitogen-activated protein kinase activation, reduces IL-1b and matrix metalloproteinase-3 and enhances IL-10 in the mucosa of children and adults with inflammatory bowel disease. British Journal of Nutrition. 103:824-832 (2010).

Ferrante et al.: Validation of Endoscopic Activity Scores in Patients with Crohn's Disease Based on a Post Hoc Analysis of Data From SONIC. Gastroenterology. 145(5):978-986 (2013).

Freeman et al.: Neural Networks: Algorithms, Applications and Programming Techniques. Addison-Wesley Publishing Company; 414 pages (1991).

Froslie et al.: Mucosal healing in inflammatory bowel disease: Results from a Norwegian populaiton-based cohort. Gastroenterology. 133:412-422 (2007).

Geboes et al.: Endoscopic and histologic evidence of persistent mucosal healing and correlation with clinical improvement following sustained infliximab treatment for Crohn's disease. Current Medical Research and Opinion. 21(11):1741-54 (2005).

Ghosh et al.: Anti-TNF therapy in Crohn's disease Novartis Foundation Symposium 263:193-218 (2004).

Gordon et al.: CC-10004 but not thalidomide or lenalidomide inhibits lamina propria mononuclear cell TNF-α and MMP-3 production in patients with inflammatory bowel disease. Journal of Crohn's and Colitis. 175-182 (2009).

Hu et al.: Research Progress of Inflammatory Bowel Disease. Basic and Clinical Medicine, Guangdong Science & Technology Press, Ltd.; pp. 46-47 (2006) machine translation.

International Application No. PCT/IB2013/059077 International Preliminary Report on Patentability dated Apr. 7, 2015.

International Application No. PCT/IB2013/059077 International Search Report and Written Opinion dated Dec. 5, 2013.

International Application No. PCT/IB2018/053923 International Search Report and Written Opinion dated Jul. 27, 2018.

International Application No. PCT/US2012/037375 International Search Report and Written Opinion dated Aug. 16, 2012.

Jiang et al.: Study on anti-tumor necrosis factor antibody for the treatment of inflammatory bowel disease. Clinical Medication Journal. 9(2):16-20 (2011).

Kelly et al.: Development and validation of a multi-marker serum test for the assessment of mucosal healing in Crohn's disease patients. American College of Gastroenterology. (2017).

Lewis: The utility of biomarkers in the diagnosis and therapy of inflammatory bowel disease. Gastroenterology. 140:1817-1826 (2011).

Li et al.: The effect of hepatocyte growth factor (Hgf) on mucosal morphology and absorption after rat small intestine transplantation. Medical Journal of Chinese People's Liberation Army. 25(4):242-244 (2000).

Moskovitz et al.: Defining and validating cut-offs for the Simple Endoscopic Score for Crohn's Disease. Gastroenterology. 132:S1097 (2007).

Neurath et al.: Mucosal healing in inflammatory bowel diseases: a systematic review. Gut. 61:1619-1635 (2012).

Noble et al.: Regional variation in gene expression in the healthy colon is dysregulated in ulcerative colitis. Gut. 57:1398-1405 (2008).

Oliva et al.: Endoscopy in Pediatric Inflammatory Bowel Disease: A Position Paper on Behalf of the Porto IBD Group of the European Society for Pediatric Gastroenterology, Hepatology and Nutrition. J Pediatr Gastroenterol Nutr. 63(3):414-430 (2018).

(56) References Cited

OTHER PUBLICATIONS

Ouyang: Editor-in-chief, Research Advances in Inflammatory Bowel Disease. Chengdu: Sichuan Science and Technology Press. pp. 207-210 (2000).
PCT/IB2013/059077 International Search Report and Written Opinion dated Dec. 5, 2013.
PCT/US2019/064224 International Preliminary Report on Patentability dated Jun. 17, 2021.
PCT/US2019/064224 International Search Report and Written Opinion dated Feb. 12, 2020.
Peyrin-Biroulet et al.: Selecting therapeutic targets in inflammatory bowel disease (STRIDE): determining therapeutic goals for treat-to-target. Am J Gastroenterol. 110(9):1324-1338 (2015).
Prometheus® Monitr™ Crohn's Disease Cat. #7300. Prometheus® Therapeutics & Diagnostics website (2018).
Scaldaferri et al.: Mucosal biomarkers in inflammatory bowel disease: Key pathogenic players or disease predictors?. World Journal of Gastroenterology. 16(21):2616-2625 (2010).
Schoepfer et al.: Monitoring inflammatory bowel disease activity: clinical activity is judged to be more relevant than endoscopic severity or biomarkers. Journal of Crohn's and Colitis. 6:412-418 (2012).
Sipponen et al.: Endoscopic evaluation of Crohn's disease activity: Comparison of the CDEIS and the SES-CD. Inflamm Bowel Dis. 16:2131-2136 (2010).
Steinberg et al.: CART: Tree Structured Non-Parametric Data Analysis. Salford Systems. 355 pages (1995).
Toedter et al.: Relationship of C-Reactive Protein With Clinical Response After Therapy With Ustekinumab in Crohn's Disease. American Journal of Gastroenterology. 104(11):2768-2773 (2009).
Tutina et al.: Lechebnoe pitanie pri nespetsificheskom yazvennom kolite i bolezni Krona u detei [Nutritional therapy for nonspecific ulcerative colitis and Crohn's disease in children]. Pediatricheskaya farmakologiya. 5(5):110-115 (2008).
U.S. Appl. No. 16/112,242 Final Office Action dated Apr. 14, 2021.
U.S. Appl. No. 16/112,242 Office Action dated Sep. 3, 2020.
U.S. Appl. No. 16/614,752 Final Office Action dated Sep. 22, 2020.
U.S. Appl. No. 16/614,752 Office Action dated Apr. 9, 2021.
U.S. Appl. No. 16/614,752 Office Action dated Jun. 11, 2020.
Vuitton et al.: IOIBD technical review on endoscopic indices for Crohn's disease clinical trials. Gut. 65(9):1447-1455 (2016).
Zadeh: Fuzzy Sets. Information and Control; 8:338-353 (1965).

- PRO Inflammatory Index (PII)
  - A single per-sample score describing inflammation levels based on five markers
- Score is the sum of five markers, log transformed
  - VEGF in pg/ml
  - CRP in ng/ml
  - SAA in ng/ml
  - ICAM in ng/ml
  - VCAM in ng/ml
- PII = log(VEGF + CRP + SAA + ICAM + VCAM)

- Patients with active CD and UC will be analyzed using novel Mobility Shift Assay in conjunction with measurements of disease activity:
  - Pharmacokinetics
    - Elimination rates
  - Disease activity profile markers
    - Select markers that correlate with changes in infliximab and ATI levels
  - Mucosal Healing
    - Biomarkers and endoscopy
- Correlations found utilizing these methods will allow us to personalize patient treatment

*FIG. 18*

Multiple Assays to detect cytokine biomarkers: bFGF, TNF-α, IL-12(p70), IL-1β, IL-2, GM- CSF, IL-13, IFN-γ, TGF-β1, TGF-β2,TGF-β3.

Multiplex Assays to detect inflammatory markers: SAA, CRP, ICAM, VCAM

Multiplex Assays to detect anti-Inflammatory: TGFbeta, IL-10

D. Tracey et al. / Pharmacology & Therapeutics 117 (2008) 244–279

Growth Factors, Cytokines, Chemokines, Acute Phase Proteins and Cellular Adhesion Molecules AREG
EREG
HB-EGF
HGF
NRG1, NRG2, NRG3, NRG4
BCT
EGF
IGF-1
HRG (including isoforms)
VEGFs (VEGFa, VEGFb, VEGFc, VEGFd)
FGFs (FGF1, FGF2 (bFGF), FGF7, FGF9)
SCF
PDGF
TWEAK
TGF-alpha
TGF-beta 1, TGF-beta 2
IFN-gamma
IL-1 beta, IL-6, IL-10
TNF-alpha
CRP
SAA
ICAM
VCAM

| | | |
|---|---|---|
| AREG | EREG | HB-EGF |
| HGF | HRG | BTC |
| EGF | IGF | TGFα |
| VEGF | | |
Signal Intensity (RFU)
Patient: 10101
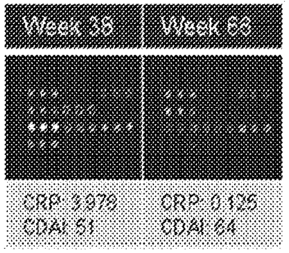
| SK05015582 Week38 | | |
|---|---|---|
| 12.16 | <7.8 | 6.6 |
| 26.6 | 143.1 | <10 |
| 0.97 | | 3.1 |
| | | |
| SK05015107 Week66 | | |
|---|---|---|
| 9.9 | <7.8 | 5 |
| 23.9 | 46.5 | <10 |
| 0.48 | | 2.0 |
| | | |
Patient: 10103
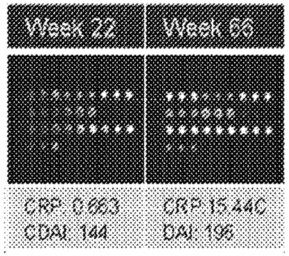
| SK05015001 Week22 | | |
|---|---|---|
| 26.06 | <7.8 | 17.8 |
| 41.3 | >2000 | <10 |
| 0.49 | | 6.6 |
| | | |
| SK05015693 Week66 | | |
|---|---|---|
| >50 | <7.8 | 18.1 |
| 82.7 | >2000 | <10 |
| 0.96 | | 6.6 |
| | | |
Patient: 10109
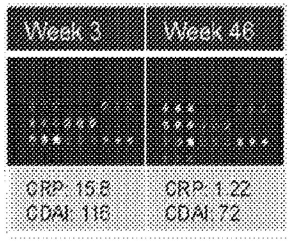
| SK05015217 Week3 | | |
|---|---|---|
| 13.91 | <7.8 | 7.8 |
| 27.4 | 243.1 | <10 |
| 0.80 | | 3.3 |
| | | |
| SK05015117 Week46 | | |
|---|---|---|
| 9.71 | <7.8 | 6.3 |
| <20 | 95.6 | <10 |
| 0.60 | | 2.6 |
| | | |
| ASCA-a | ASCA-g | Cbir-1 | OMPC |
|---|---|---|---|
| 53.49 | 20.23 | 34.91 | 10.83 |
| 42.40 | 18.01 | 32.05 | 8.74 |
Patient: 10118
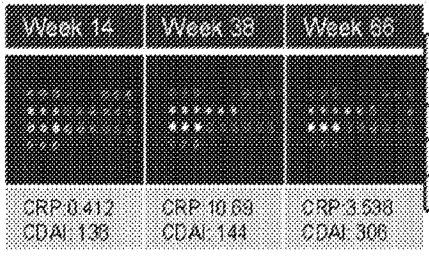
| SK05015621 Week14 | | |
|---|---|---|
| 27.14 | <15.6 | 10.5 |
| 26.1 | 541.3 | <10 |
| 1.22 | | 7.1 |
| | | |
| SK05015452 Week38 | | |
|---|---|---|
| 22.33 | <15.6 | 6.9 |
| 22.0 | 443.9 | <10 |
| 1.36 | | 5.7 |
| | | |
| SK05015744 Week46 | | |
|---|---|---|
| 21.39 | <15.6 | 7.8 |
| 29.9 | 492.7 | 26 |
| 1.32 | | 6.4 |
| | | |
| ASCA-a | ASCA-g | Cbir-1 | OMPC |
|---|---|---|---|
| 27.73 | 467.01 | 57.94 | 5.11 |
| 14.33 | 322.31 | 16.05 | 4.94 |
| 13.82 | 306.22 | 18.77 | 4.54 |
FIG. 21B Patient: 190
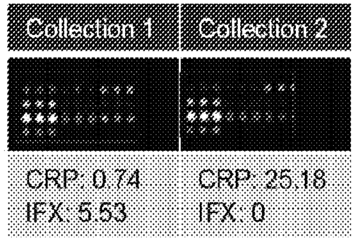
| REM-1039-VAK.3 | | |
|---|---|---|
| | | 5.9 |
| 10.8 | | |
| 0.90 | | 1.9 |
| | | |
| REM-1039-VAK.12 | | |
|---|---|---|
| | | 5.7 |
| 11.5 | | |
| 0.98 | | |
| | | |
Patient: 2546
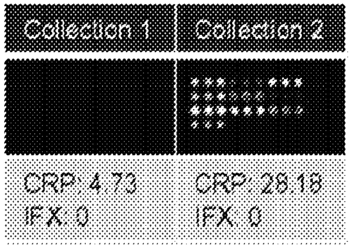
| REM-1281-LAL.96 | | |
|---|---|---|
| | | |
| | | |
| | | |
| | | |
| REM-1281-LAL.97 | | |
|---|---|---|
| 26.12 | | 13.3 |
| 38.8 | 912.7 | |
| 0.88 | | 5.4 |
| | | |
Patient: 7757
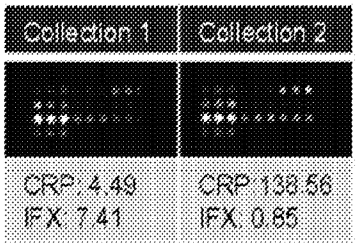
| REM-1092-HOP.709 | | |
|---|---|---|
| 2.60 | | 6.9 |
| 26.0 | | |
| 0.90 | | 6.8 |
| | | |
| REM-1092-HOP.722 | | |
|---|---|---|
| 2.74 | | 5.7 |
| 42.8 | | |
| 0.90 | | 6.8 |
| | | |
Patient: 7966
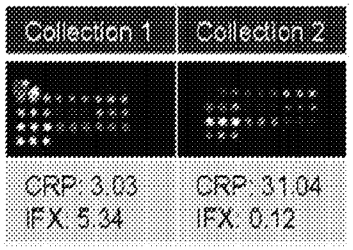
| REM-1137-DEF.742 | | |
|---|---|---|
| 4.18 | | 6.1 |
| 20.9 | | 35 |
| 0.94 | | 3.3 |
| | | |
| REM-1137-DEF.744 | | |
|---|---|---|
| 2.39 | | 5.7 |
| 35.8 | | |
| 0.91 | | 2.6 |
| | | |
| | | |
|---|---|---|
| AREG | EREG | HB-EGF |
| HGF | HRG | BTC |
| EGF | IGF | TGFα |
| VEGF | | |
Signal Intensity (RFU)
*FIG. 21D*

Patient: 10308
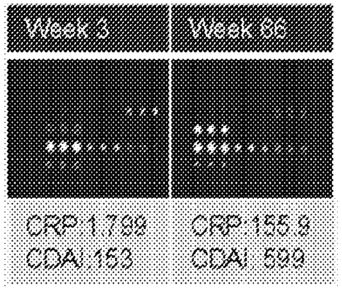
SK05015590 Week3
| | | |
|---|---|---|
| | | 4.3 |
| 45.1 | | |
| 1.26 | | |
| | | |
SK05015731 Week66
| | | |
|---|---|---|
| | | 5.3 |
| 121.7 | | |
| 1.22 | | |
| | | |
| ASCA-a | ASCA-g | Cbir-1 | OMPC |
|---|---|---|---|
| 39.22 | 53.44 | 9.24 | 8.98 |
| 88.48 | 131.55 | 6.42 | 21.21 |
Patient: 10503
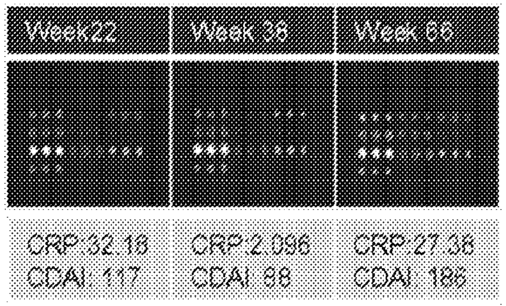
SK05015053 Week22
| | | |
|---|---|---|
| 4.88 | | 5.2 |
| 39.2 | | |
| 0.51 | | |
| | | |
SK05015661 Week38
| | | |
|---|---|---|
| 4.92 | | 2.8 |
| 35.4 | | |
| 0.49 | | |
| | | |
SK05015491 Week46
| | | |
|---|---|---|
| 7.08 | | 5.8 |
| 46.1 | 145.7 | |
| 0.50 | | 1.7 |
| | | |
Patient: 11003
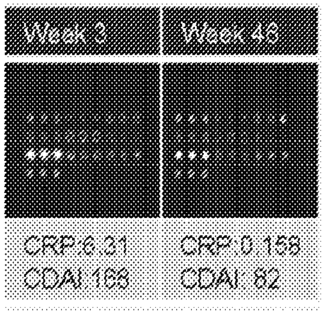
SK05015219 Week3
| | | |
|---|---|---|
| 10.22 | | 5.8 |
| 31.1 | 205.2 | |
| 0.49 | | 3.3 |
| | | |
SK05015631 Week46
| | | |
|---|---|---|
| 7.28 | | 5.4 |
| 26.0 | 124.5 | |
| 0.55 | | 2.8 |
| | | |
| | | |
|---|---|---|
| AREG | EREG | HB-EGF |
| HGF | HRG | BTC |
| EGF | IGF | TGFα |
| VEGF | | |
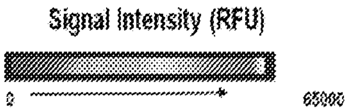
FIG. 21E

METHODS OF DISEASE ACTIVITY PROFILING FOR PERSONALIZED THERAPY MANAGEMENT

CROSS-REFERENCES TO RELATED APPLICATIONS

This application is a continuation of U.S. application Ser. No. 16/112,242, filed Aug. 24, 2018, now issued as U.S. Pat. No. 11,160,863, on Nov. 2, 2021, which is a continuation of U.S. application Ser. No. 14/072,746, filed Nov. 5, 2013, issued as U.S. Pat. No. 10,086,072 on Oct. 2, 2018, which is a continuation of Int. Application No. PCT/US2012/037375, filed May 10, 2012, which application claims priority to U.S. Provisional Patent Application No. 61/484,607, filed May 10, 2011, U.S. Provisional Patent Application No. 61/505,026, filed Jul. 6, 2011, U.S. Provisional Application No. 61/553,909, filed Oct. 31, 2011, U.S. Provisional Application No. 61/566,509, filed Dec. 2, 2011, and U.S. Provisional Application No. 61/636,575, filed Apr. 20, 2012, the disclosures of which are hereby incorporated by reference in their entirety for all purposes.

BACKGROUND OF THE INVENTION

Inflammatory bowel disease (IBD) which includes Crohn's disease (CD) and ulcerative colitis (UC) is a chronic idiopathic inflammatory disorder affecting the gastrointestine tract. Disease progression of CD and UC includes repeated episodes of inflammation and ulceration of the intestine, leading to complications requiring hospitalization, surgery and escalation of therapy (Peyrin-Biroulet et al., *Am. J. Gastroenterol.,* 105: 289-297 (2010); Langholz E., *Dan. Med. Bull.,* 46: 400-415 (1999)). Current treatments such as anti-tumor necrosis factor-alpha (TNF-α) biologics (e.g., infliximab (IFX), etanercept, adalimumab (ADL) and certolizumab pegol), thiopurine drugs (e.g., azathioprine (AZA), 6-mercaptopurin (6-MP)), anti-inflammatory drugs (e.g., mesalazine), and steroids (e.g., corticosteroids) have been shown to reduce disease activity. In some clinical trials of CD, mucosal healing which is described as the absence of intestinal ulcers, was induced in patients on combination therapy of corticosteroids, IFX and ADL. Furthermore, MH was maintained in patients receiving IFX.

Other studies have shown that mucosal healing can be a hallmark of suppression of bowel inflammation and predict long-term disease remission (Froslie et al., *Gastroenterology,* 133: 412-422 (2007); Baert et al., *Gastroenterology*, (2010)). Long-term mucosal healing has been associated with a decreased risk of colectomy and colorectal cancer in UC patients, a decreased need for corticosteroid treatment in CD patients, and possibly a decreased need for hospitalization (Dave et al., *Gastroenterology & Hepatology,* 8(1): 29-38 (2012)).

The International Organization for the Study of Inflammatory Bowel Disease proposed defining mucosal healing in UC as the absence of friability, blood, erosions an dulcers in all visualized segments of gut mucosa (D'Haens et al., Gastroenterology, 132: 763-786 (2007)). MH in CD was proposed to be the absence of ulcers. The gold standard for measurement of Crohn's disease activity is the Crohn's Disease Endoscopic Index of Severity (CDEIS). This disease index score is established from several variables such as superficial and deep ulceration, ulcerated and nonulcerated stenosis, and surface area of ulcerated and disease segments. A simplified version of the index is the Simple Endoscopic Score for Crohn's Disease, which takes into account disease variables including ulcer size, ulcerated surface, affected surface and presence of narrowing. Both indices evaluate clinical symptoms of CD, yet fail to measure the underlying cause of disease (e.g., inflammation) or resolution of disease (e.g., mucosal healing). A measurement of mucosal healing can be performed to assess disease induction as well as disease progression and resolution.

The process of mucosal healing begins with bleeding (e.g., degradation of the endothelial layers of the blood vessels) and inflammation, then progresses to cell and tissue proliferation, and finally tissue remodeling. At the inflammation stage, inflammatory markers and anti-inflammatory markers, such as, but not limited to, IL-1, IL-2, IL-6, IL-14, IL-17, TGFβ, and TNFα are expressed. During remodeling, tissue repair and remodeling growth factors, such as, but not limited to, AREG, EREG, HB-EGF, HGF, NRG1-4, BTC, EGF, IGF, TGF-α, VEGFs, FGFs, and TWEAK are expressed. Repair of the intestinal epithelium requires multiple signal transduction pathways which are necessary for cell survival, proliferation, and migration. We have identified novel markers of mucosal healing that are predictive of the risk of disease relapse and disease remission. A measurement of mucosal healing can be used to periodically assess disease status in patients receiving a therapy regimen.

Mucosal healing is typically assessed by endoscopy. Although the invasive procedure is considered to be low-risk, its cost and patient discomfort and compliance remain obstacles to frequent, regular endoscopies to assess mucosal healing. There is an unmet need in the art for non-invasive methods of determining mucosal healing in a patient.

There is a need in the art for methods of therapeutic management of diseases such as autoimmune disorders using an individualized approach to optimize therapy and monitor efficacy. The methods need to include assessing disease course and clinical parameters such as pharmacokinetics, disease activity indices, disease burden, and mucosal status. The present invention satisfies this need and provides related advantages as well.

BRIEF SUMMARY OF THE INVENTION

The present invention provides methods for personalized therapeutic management of a disease in order to optimize therapy and/or monitor therapeutic efficacy. In particular, the present invention comprises measuring an array of one or a plurality of mucosal healing biomarkers at one or a plurality of time points over the course of therapy with a therapeutic agent to determine a mucosal healing index for selecting therapy, optimizing therapy, reducing toxicity, and/or monitoring the efficacy of therapeutic treatment. In some embodiments, the therapy is an anti-TNF therapy, an immunosuppressive agent, a corticosteroid, a drug that targets a different mechanism, a nutrition therapy and combinations thereof. In certain instances, the anti-TNF therapy is a TNF inhibitor (e.g., anti-TNF drug, anti-TNFα antibody) for the treatment of a TNFα-mediated disease or disorder.

TNFα has been implicated in inflammatory diseases, autoimmune diseases, viral, bacterial and parasitic infections, malignancies, and/or neurodegenerative diseases and is a useful target for specific biological therapy in diseases, such as rheumatoid arthritis and Crohn's disease. TNF inhibitors such as anti-TNFα antibodies are an important class of therapeutics. In some embodiments, the methods of the present invention advantageously improve therapeutic management of patients with a TNFα-mediated disease or disorder by optimizing therapy and/or monitoring therapeutic efficacy to anti-TNF drugs such as anti-TNFα therapeutic antibodies.

As such, in one aspect, the present invention provides a non-invasive method for measuring mucosal healing in an individual diagnosed with inflammatory bowel disease (IBD) receiving a therapy regimen, the method comprising:

(a) measuring the levels of an array of mucosal healing markers in a sample from the individual;

(b) comparing the levels of an array of mucosal healing markers in the individual to that of a control to compute the mucosal healing index of the individual, wherein the mucosal healing index comprises a representation of the extent of mucosal healing; and (c) determining whether the individual undergoing mucosal healing should maintain the therapy regimen.

As such, in one aspect, the present invention provides a method for monitoring therapeutic efficiency in an individual with IBD receiving therapy, the method comprising:

(a) measuring levels of an array of mucosal healing markers in a sample from the individual at a plurality of time points over the course of therapy with a therapeutic antibody;

(b) applying a statistical algorithm to the level of the one or more markers determined in step (a) to generate a mucosal healing index;

(c) comparing the individual's mucosal healing index to that of a control; and (d) determining whether the therapy is appropriate for the individual to promote mucosal healing.

In another aspect, the present invention provides a method for selecting a therapy regimen in an individual with IBD, the method comprising:

(a) measuring levels of an array of mucosal healing markers in a sample from the individual at a plurality of time points over the course of therapy, the individual receiving a therapeutic antibody;

(b) applying a statistical algorithm to the level of the one or more markers determined in step (a) to generate a mucosal healing index;

(c) comparing the individual's mucosal healing index to that of a control; and (d) selecting an appropriate therapy regimen for the individual wherein the therapy regimen promotes mucosal healing As such, in another aspect, the present invention provides a method for reducing or minimizing the risk of surgery in an individual diagnosed with IBD being administered a therapy regimen, the method comprising:

(a) measuring an array of mucosal healing markers at a plurality of time points over the course of therapy with a therapeutic antibody;

(b) generating the individual's mucosal healing index comprising a representation of the presence and/or concentration levels of each of the markers over time;

(c) comparing the individual's mucosal healing index to that of a control, and (d) selecting an appropriate therapy regimen for to reduce or minimize the risk of surgery.

As such, in another aspect, the present invention provides a method for selecting a therapy regimen to promote mucosal healing in an individual diagnosed with IBD, the method comprising:

(a) measuring levels of a panel of mucosal healing markers at time point $t_0$ to generate a mucosal healing index at to;

(b) measuring levels of a panel of mucosal healing markers at time point $t_1$ to generate a mucosal healing index at $t_1$;

(c) comparing the change in the mucosal healing index from $t_0$ to $t_1$; and (d) selecting the therapy regimen for the individual to promote mucosal healing.

As such, in one aspect, the present invention provides a non-invasive method for measuring mucosal healing in an individual diagnosed with Crohn's disease receiving an anti-TNF therapy regimen, the method comprising:

(a) measuring the levels of an array of mucosal healing markers in a sample from the individual;

(b) comparing the levels of an array of mucosal healing markers in the individual to that of a control to compute the mucosal healing index of the individual, wherein the mucosal healing index comprises a representation of the extent of mucosal healing; and (c) determining whether the individual undergoing mucosal healing should maintain the anti-TNF therapy regimen.

As such, in another aspect, the present invention provides a method for monitoring therapeutic efficiency in an individual with Crohn's disease receiving anti-TNF therapy, the method comprising:

(a) measuring levels of an array of mucosal healing markers in a sample from the individual at a plurality of time points over the course of therapy with a therapeutic antibody;

(b) applying a statistical algorithm to the level of the one or more markers determined in step (a) to generate a mucosal healing index;

(c) comparing the individual's mucosal healing index to that of a control; and (d) determining whether the anti-TNF therapy is appropriate for the individual to promote mucosal healing.

As such, in another aspect, the present invention provides a method for selecting an anti-TNF therapy regimen in an individual with Crohn's disease, the method comprising:

(a) measuring levels of an array of mucosal healing markers in a sample from the individual at a plurality of time points over the course of therapy, the individual receiving a therapeutic antibody;

(b) applying a statistical algorithm to the level of the one or more markers determined in step (a) to generate a mucosal healing index;

(c) comparing the individual's mucosal healing index to that of a control; and (d) selecting an appropriate anti-TNF therapy regimen for the individual wherein the anti-TNF therapy promotes mucosal healing.

As such, in another aspect, the present invention provides a method for reducing or minimizing the risk of surgery in an individual diagnosed with Crohn's disease being administered an anti-TNF antibody therapy regimen, the method comprising:

(a) measuring an array of mucosal healing markers at a plurality of time points over the course of therapy with a therapeutic antibody;

(b) generating the individual's mucosal healing index comprising a representation of the presence and/or concentration levels of each of the markers over time;

(c) comparing the individual's mucosal healing index to that of a control, and (d) selecting an appropriate anti-TNF antibody therapy regimen for to reduce or minimize the risk of surgery.

As such, in another aspect, the present invention provides a method for selecting an anti-TNF antibody therapy regimen to promote mucosal healing in an individual diagnosed with Crohn's disease, the method comprising:

(a) measuring levels of a panel of mucosal healing markers at time point $t_0$ to generate a mucosal healing index at to;

(b) measuring levels of a panel of mucosal healing markers at time point $t_1$ to generate a mucosal healing index at $t_1$;

(c) comparing the change in the mucosal healing index from $t_0$ to $t_1$; and (d) selecting the anti-TNF antibody therapy regimen for the individual to promote mucosal healing.

In some embodiments, the disease is a gastrointestinal disease or an autoimmune disease. In certain instances, the subject has Crohn's disease (CD) or rheumatoid arthritis (RA). In other embodiments, the therapeutic antibody is an anti-TNFα antibody. In some embodiments, the anti-TNFα antibody is a member selected from the group consisting of REMICADE™ (infliximab), ENBREL™ (etanercept), HUMIRA™ (adalimumab), CIMZIA® (certolizumab pegol), and combinations thereof. In preferred embodiments, the subject is a human.

In some embodiments, the array of markers comprises a mucosal healing marker. In some embodiments, the mucosal marker comprises AREG, EREG, HB-EGF, HGF, NRG1, NRG2, NRG3, NRG4, BTC, EGF, IGF, TGF-α, VEGF-A, VEGF-B, VEGF-C, VEGF-D, FGF1, FGF2, FGF7, FGF9, TWEAK and combinations thereof.

On other embodiments, the array of markers further comprises a member selected from the group consisting of an anti-TNFα antibody, an anti-drug antibody (ADA), an inflammatory marker, an anti-inflammatory marker, a tissue repair marker (e.g., a growth factor), and combinations thereof. In certain instances, the anti-TNFα antibody is a member selected from the group consisting of REMICADE™ (infliximab), ENBREL™ (etanercept), HUMIRA™ (adalimumab), CIMZIA® (certolizumab pegol), and combinations thereof. In certain other instances, the anti-drug antibody (ADA) is a member selected from the group consisting of a human anti-chimeric antibody (HACA), a human anti-humanized antibody (HAHA), a human anti-mouse antibody (HAMA), and combinations thereof. In yet other instances, the inflammatory marker is a member selected from the group consisting of GM-CSF, IFN-γ, IL-1β, IL-2, IL-6, IL-8, TNF-α, sTNF RII, and combinations thereof. In further instances, the anti-inflammatory marker is a member selected from the group consisting of IL-12p70, IL-10, and combinations thereof.

In certain embodiments, the array comprises at least 2, 3, 4, 5, 6, 7, 8, 9, 10, 11, 12, 13, 14, 15, 16, 17, 18, 19, 20, 21, 22, 23, 24, 25, 30, 35, 40, 45, 50, or more markers. In some embodiments, the markers are measured in a biological sample selected from the group consisting of serum, plasma, whole blood, stool, peripheral blood mononuclear cells (PBMC), polymorphonuclear (PMN) cells, and a tissue biopsy (e.g., from a site of inflammation such as a portion of the gastrointestinal tract or synovial tissue).

In certain embodiments, the plurality of time points comprises at least 2, 3, 4, 5, 6, 7, 8, 9, 10, 11, 12, 13, 14, 15, 16, 17, 18, 19, 20, 25, 30, 35, 40, 45, 50, or more time points. In some instances, the first time point in the plurality of time points is prior to the course of therapy with the therapeutic antibody. In other instances, the first time point in the plurality of time points is during the course of therapy with the therapeutic antibody. As non-limiting examples, each of the markers can be measured prior to therapy with a therapeutic antibody and/or during the course of therapy at one or more (e.g., a plurality) of the following weeks: 1, 2, 3, 4, 5, 6, 7, 8, 9, 10, 11, 12, 13, 14, 15, 16, 17, 18, 19, 20, 22, 24, 26, 28, 30, 32, 34, 36, 38, 40, 42, 44, 46, 48, 50, 52, 54, 56, 58, 60, 62, 64, 66, 68, 70, 80, 90, 100, etc.

In some embodiments, selecting an appropriate therapy comprises maintaining, increasing, or decreasing a subsequent dose of the course of therapy for the subject. In other embodiments, the method further comprises determining a different course of therapy for the subject. In certain instances, the different course of therapy comprises treatment with a different anti-TNFα antibody. In other instances, the different course of therapy comprises the current course of therapy along with another therapeutic agent, such as, but not limited to an anti-TNF therapy, an immunosuppressive agent, a corticosteroid, a drug that targets a different mechanism, a nutrition therapy and other combination treatments.

In some embodiments, selecting an appropriate therapy comprises selecting an appropriate therapy for initial treatment. In some instances, the therapy comprises an anti-TNFα antibody therapy.

In certain embodiments, the methods disclosed herein can be used as confirmation that a proposed new drug or therapeutic is the same as or is sufficiently similar to an approved drug product, such that the proposed new drug can be used as a "biosimilar" therapeutic. For example, if the proposed new drug has only a slightly different disease activity profile compared to the branded drug product, this would be apparent using the methods disclosed herein. If the proposed new drug has a significantly different disease activity profile compared to the branded drug product, then the new drug would not be biosimilar. Advantageously, the methods disclosed herein can be used in clinical trials of proposed new drugs in order to assess the effective therapeutic efficacy or value of the drug.

Accordingly, in some aspects, the methods of the invention provide information useful for guiding treatment decisions for patients receiving or about to receive anti-TNF drug therapy, e.g., by selecting an appropriate anti-TNF therapy for initial treatment, by determining when or how to adjust or modify (e.g., increase or decrease) the subsequent dose of an anti-TNF drug, by determining when or how to combine an anti-TNF drug (e.g., at an initial, increased, decreased, or same dose) with one or more immunosuppressive agents such as methotrexate (MTX) or azathioprine (AZA), and/or by determining when or how to change the current course of therapy (e.g., switch to a different anti-TNF drug or to a drug that targets a different mechanism such as an IL-6 receptor-inhibiting monoclonal antibody, anti-integrin molecule (e.g., Tysabri, Vedaluzamab), JAK-2 inhibitor, and tyrosine kinase inhibitor, or to a nutrition therapy (e.g., special carbohydrate diet)).

In other embodiments, the methods of the present invention can be used to predict responsiveness to a TNFα inhibitor, especially to an anti-TNFα antibody in a subject having an autoimmune disorder (e.g., rheumatoid arthritis, Crohn's Disease, ulcerative colitis and the like.). In this method, by assaying the subject for the correct or therapeutic dose of anti-TNFα antibody, i.e., the therapeutic concentration level, it is possible to predict whether the individual will be responsive to the therapy.

In another embodiment, the present invention provides methods for monitoring IBD (e.g., Crohn's disease and ulcerative colitis) in a subject having the IBD disorder, wherein the method comprises assaying the subject for the correct or therapeutic dose of anti-TNFα antibody, i.e., the therapeutic concentration level, over time. In this manner, it is possible to predict whether the individual will be responsive to the therapy over the given time period.

Other objects, features, and advantages of the present invention will be apparent to one of skill in the art from the following detailed description and figures.

BRIEF DESCRIPTION OF THE DRAWINGS

FIG. 18 shows details of methods for improved patient management of CD and/or UC.

FIGS. 21A-G illustrate multiplexed growth factor profiling of patient samples using CEER growth factor arrays.

FIG. 26A shows presence of IFX and ATI in the pair's first data point and CRP in the subsequent measurements. FIG. 26B shows CRP levels, IFX serum concentration and ATI status at sequential time points for a sample. In this sample CRP levels are lowest when the patient is ATI- and has a serum IFX concentration higher than threshold.

DETAILED DESCRIPTION OF THE INVENTION

I. Introduction

Figure 1:
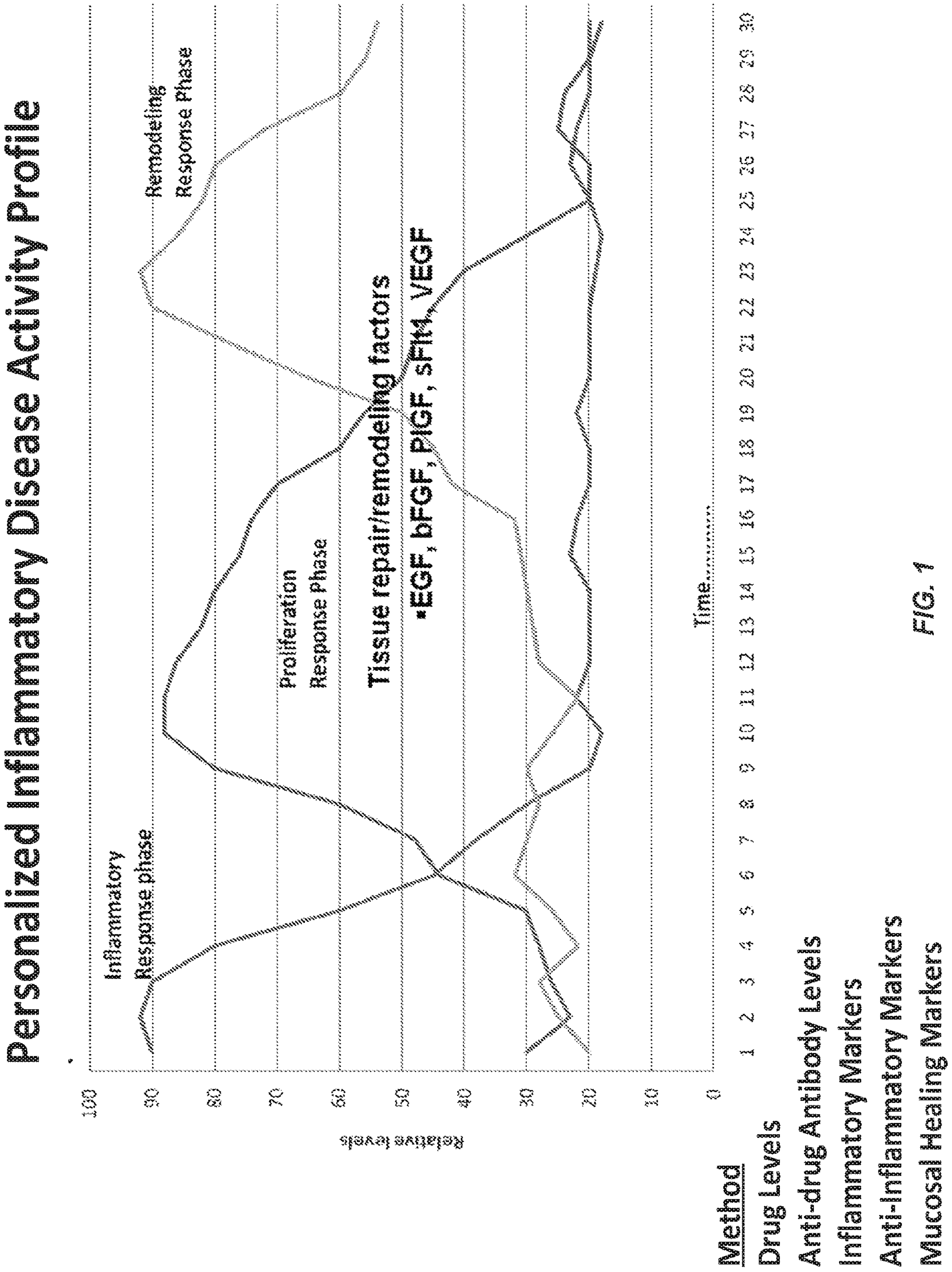
FIG. 1 shows a personalized IBD activity profile as described in Example 1.
Figure 2A:
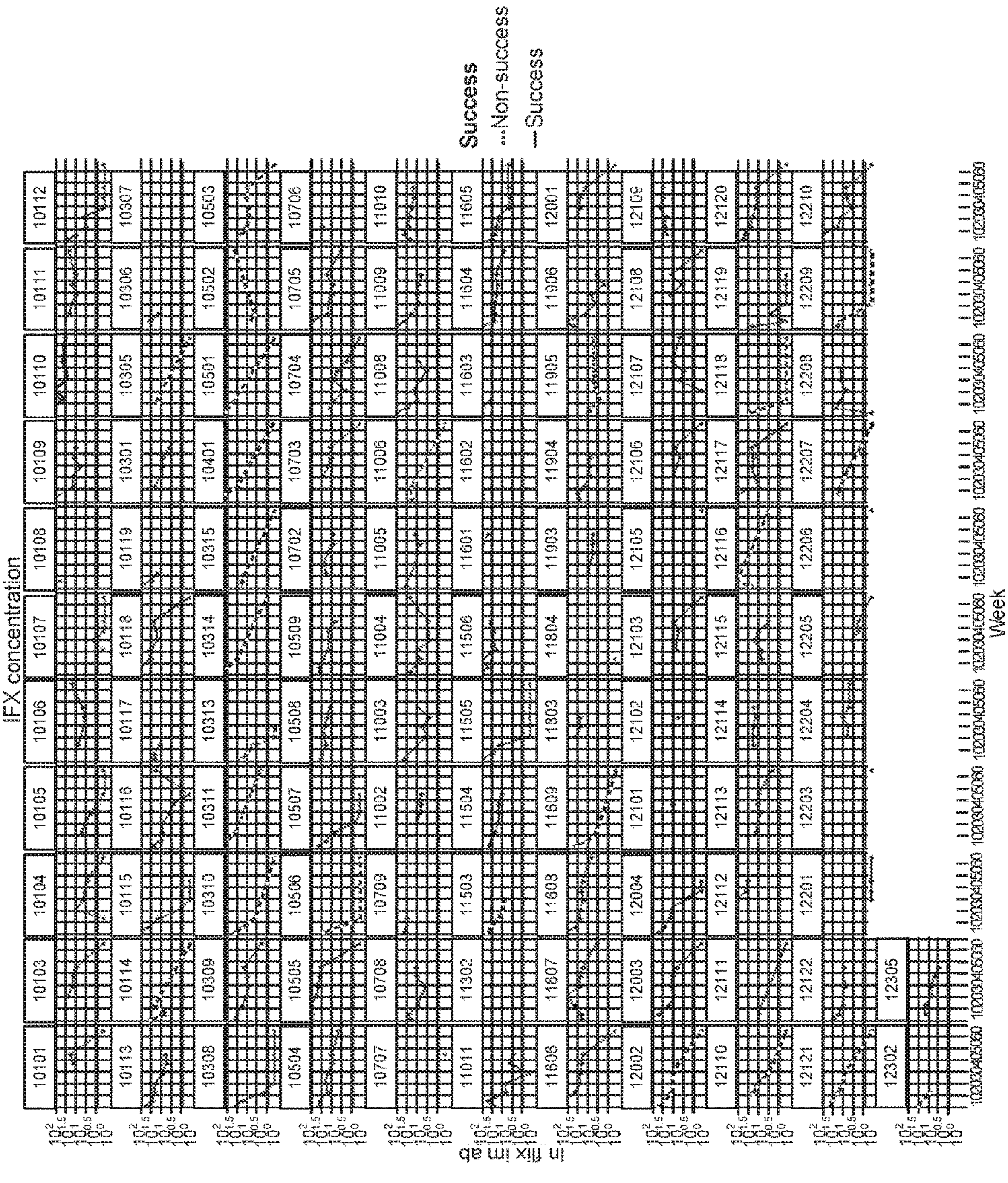
FIG. 2A show various patient infliximab concentrations as a function of treatment time.
Figure 2B:
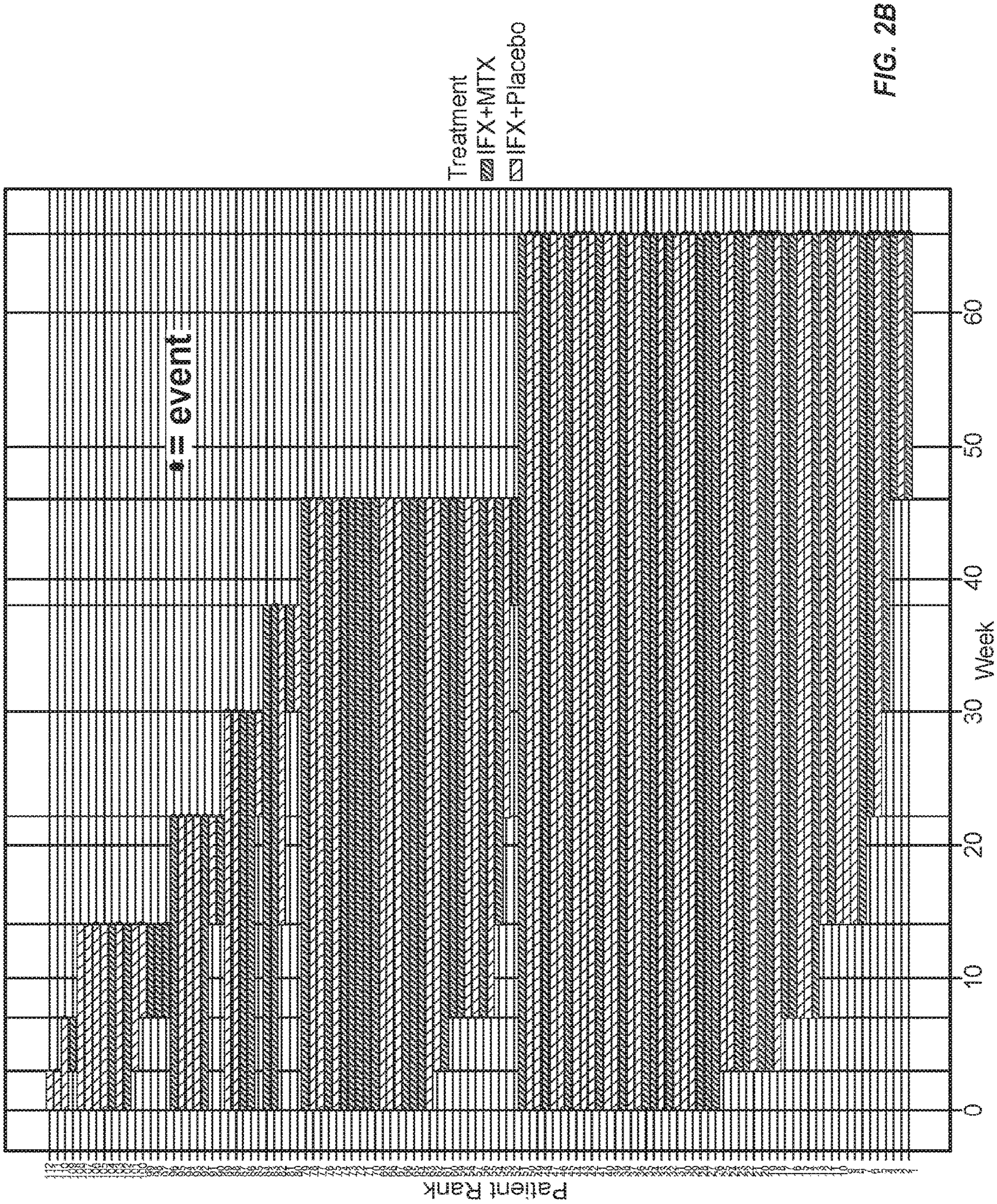
FIG. 2B shows patient ranks over a course of treatment with events (infliximab falling below a threshold concentration) noted.
Figure 3A:
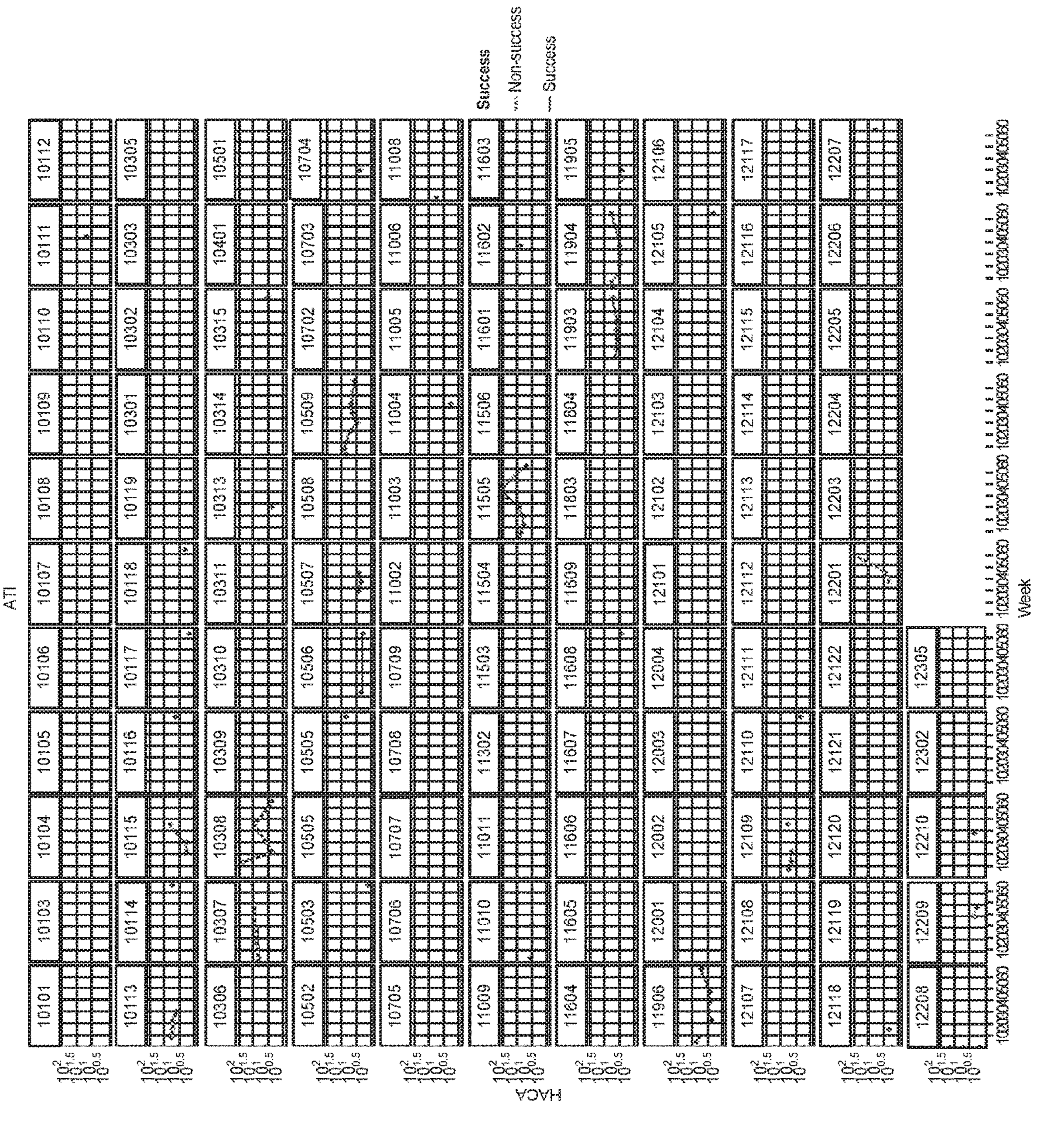
FIG. 3A show various patient HACA (ATI) concentrations as a function of treatment time.
Figure 3B:
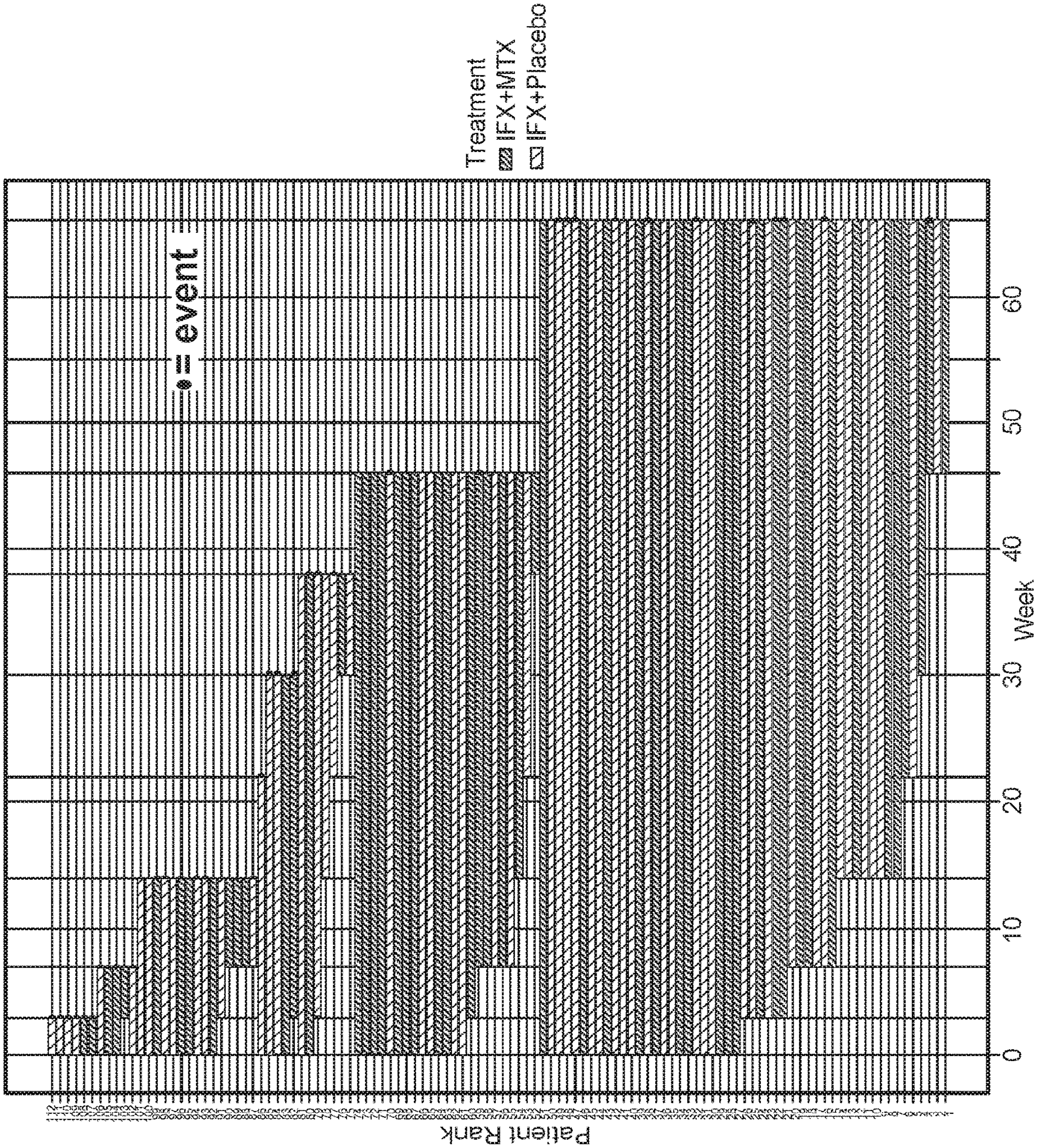
FIG. 3B shows patient ranks over a course of treatment with events (HACA detection or appearance) noted.

The present invention provides methods for measuring mucosal healing in patients with IBD, CD and/or UC. In particular, the present invention provides methods of measuring mucosal healing markers wherein the markers are indicative of intestinal tissue repair, and disease resolution or remission.

The present invention is advantageous because it addresses and overcomes current limitations associated with monitoring mucosal healing in patients with IBD (e.g., Crohn's disease and ulcerative colitis). The present invention provides non-invasive methods for monitoring mucosal healing patients receiving anti-TNF therapy. In addition, the present invention provides methods of predicting therapeutic response, risk of relapse, and risk of surgery in patients with IBD (e.g., Crohn's disease and ulcerative colitis). In particular, the methods of the present invention find utility for selecting an appropriate anti-TNF therapy for initial treatment, for determining when or how to adjust or modify (e.g., increase or decrease) the subsequent dose of an anti-TNF drug to optimize therapeutic efficacy and/or to reduce toxicity, for determining when or how to combine an anti-TNF drug (e.g., at an initial, increased, decreased, or same dose) with one or more immunosuppressive agents such as methotrexate (MTX) or azathioprine (AZA), and/or for determining when or how to change the current course of therapy (e.g., switch to a different anti-TNF drug or to a drug that targets a different mechanism). The present invention also provides methods for selecting an appropriate therapy for patients diagnosed with CD, wherein the therapy promotes mucosal healing.

II. Definitions

As used herein, the following terms have the meanings ascribed to them unless specified otherwise.

The phrase "mucosal healing index" includes an empirically derived index that is based upon an analysis of a plurality of mucosal healing markers. In one aspect, the concentration of markers or their measured concentration values are transformed into an index by an algorithm resident on a computer. In certain aspects, the index is a synthetic or human derived output, score, or cut off value(s), which expresses the biological data in numerical terms. The index can be used to determine or make or aid in making a clinical decision. A mucosal healing index can be measured multiple times over the course of time. In one aspect, the algorithm can be trained with known samples and thereafter validated with samples of known identity.

The phrase "mucosal healing index control" includes a mucosal healing index derived from a healthy individual, or an individual who has progressed from a disease state to a healthy state. Alternatively, the control can be an index representing a time course of a more diseased state to a less disease state or to a healthy state.

The phrase "determining the course of therapy" and the like includes the use of an empirically derived index, score or analysis to select for example, selecting a dose of drug, selecting an appropriate drug, or a course or length of therapy, a therapy regimen, or maintenance of an existing drug or dose. In certain aspects, a derived or measured index can be used to determine the course of therapy.

The terms "TNF inhibitor", "TNF-α inhibitor" and "TNFα inhibitor" as used herein are intended to encompass agents including proteins, antibodies, antibody fragments, fusion proteins (e.g., Ig fusion proteins or Fc fusion proteins), multivalent binding proteins (e.g., DVD Ig), small molecule TNF-α antagonists and similar naturally- or non-naturally-occurring molecules, and/or recombinant and/or engineered forms thereof, that, directly or indirectly, inhibits TNF a activity, such as by inhibiting interaction of TNF-α with a cell surface receptor for TNF-α, inhibiting TNF-α protein production, inhibiting TNF-α gene expression, inhibiting TNFα secretion from cells, inhibiting TNF-α receptor signaling or any other means resulting in decreased TNF-α activity in a subject. The term "TNFα inhibitor" preferably includes agents which interfere with TNF-α activity. Examples of TNF-α inhibitors include etanercept (ENBREL™, Amgen), infliximab (REMICADE™, Johnson and Johnson), human anti-TNF monoclonal antibody adalimumab (D2E7/HUMIRA™, Abbott Laboratories), CDP 571 (Celltech), and CDP 870 (Celltech), as well as other compounds which inhibit TNF-α activity, such that when administered to a subject suffering from or at risk of suffering from a disorder in which TNF-α activity is detrimental (e.g., RA), the disorder is treated.

The term "predicting responsiveness to a TNFα inhibitor", as used herein, is intended to refer to an ability to assess the likelihood that treatment of a subject with a TNF inhibitor will or will not be effective in (e.g., provide a measurable benefit to) the subject. In particular, such an ability to assess the likelihood that treatment will or will not be effective typically is exercised after treatment has begun, and an indicator of effectiveness (e.g., an indicator of measurable benefit) has been observed in the subject. Particularly preferred TNFα inhibitors are biologic agents that have been approved by the FDA for use in humans in the treatment of rheumatoid arthritis, which agents include adalimumab (HUMIRA™) infliximab (REMICADE™) and etanercept (ENBREL™), most preferably adalimumab (HUMIRA™).

The term "course of therapy" includes any therapeutic approach taken to relieve or prevent one or more symptoms associated with a TNFα-mediated disease or disorder. The term encompasses administering any compound, drug, procedure, and/or regimen useful for improving the health of an individual with a TNFα-mediated disease or disorder and includes any of the therapeutic agents described herein. One skilled in the art will appreciate that either the course of therapy or the dose of the current course of therapy can be changed (e.g., increased or decreased) based upon the presence or concentration level of TNF, anti-TNF drug, and/or anti-drug antibody using the methods of the present invention.

The term "immunosuppressive agent" includes any substance capable of producing an immunosuppressive effect, e.g., the prevention or diminution of the immune response, as by irradiation or by administration of drugs such as anti-metabolites, anti-lymphocyte sera, antibodies, etc. Examples of suitable immunosuppressive agents include, without limitation, thiopurine drugs such as azathioprine (AZA) and metabolites thereof, anti-metabolites such as methotrexate (MTX); sirolimus (rapamycin); temsirolimus; everolimus; tacrolimus (FK-506); FK-778; anti-lymphocyte globulin antibodies, anti-thymocyte globulin antibodies, anti-CD3 antibodies, anti-CD4 antibodies, and antibody-toxin conjugates; cyclosporine; mycophenolate; mizoribine monophosphate; scoparone; glatiramer acetate; metabolites thereof, pharmaceutically acceptable salts thereof; derivatives thereof; prodrugs thereof; and combinations thereof.

The term "thiopurine drug" includes azathioprine (AZA), 6-mercaptopurine (6-MP), or any metabolite thereof that has therapeutic efficacy and includes, without limitation, 6-thioguanine (6-TG), 6-methylmercaptopurine riboside, 6-thioinosine nucleotides (e.g., 6-thioinosine monophosphate, 6-thioinosine diphosphate, 6-thioinosine triphosphate), 6-thioguanine nucleotides (e.g., 6-thioguanosine monophosphate, 6-thioguanosine diphosphate, 6-thioguanosine triphosphate), 6-thioxanthosine nucleotides (e.g., 6-thioxanthosine monophosphate, 6-thioxanthosine diphosphate, 6-thioxanthosine triphosphate), derivatives thereof, analogues thereof, and combinations thereof.

The term "sample" as used herein includes any biological specimen obtained from a patient. Samples include, without limitation, whole blood, plasma, serum, red blood cells, white blood cells (e.g., peripheral blood mononuclear cells (PBMC), polymorphonuclear (PMN) cells), ductal lavage fluid, nipple aspirate, lymph (e.g., disseminated tumor cells of the lymph node), bone marrow aspirate, saliva, urine, stool (i.e., feces), sputum, bronchial lavage fluid, tears, fine needle aspirate (e.g., harvested by random periareolar fine needle aspiration), any other bodily fluid, a tissue sample such as a biopsy of a site of inflammation (e.g., needle biopsy), and cellular extracts thereof. In some embodiments, the sample is whole blood or a fractional component thereof such as plasma, serum, or a cell pellet. In other embodiments, the sample is obtained by isolating PBMCs and/or PMN cells using any technique known in the art. In yet other embodiments, the sample is a tissue biopsy, e.g., from a site of inflammation such as a portion of the gastrointestinal tract or synovial tissue.

The term "Crohn's Disease Activity Index" or "CDAI" includes a research tool used to quantify the symptoms of patients with Crohn's disease (CD). The CDAI is generally used to define response or remission of CD. The CDAI consists of eight factors, each summed after adjustment with a weighting factor. The components of the CDAI and weighting factors are the following:

| Clinical or laboratory variable | Weighting factor |
|---|---|
| Number of liquid or soft stools each day for seven days | ×2 |
| Abdominal pain (graded from 0-3 on severity) each day for seven days | ×5 |
| General well being, subjectively assessed from 0 (well) to 4 (terrible) each day for seven days | ×7 |
| Presence of complications* | ×20 |
| Taking Lomitil or opiates for diarrhea | ×30 |
| Presence of an abdominal mass (0 as none, 2 as questionable, 5 as definite) | ×10 |
| Hematocrit of <0.47 in men and <0.42 in women | ×6 |
| Percentage deviation from standard weight | ×1 |

One point each is added for each set of complications:
- the presence of joint pains (arthralgia) or frank arthritis;
- inflammation of the iris or uveitis;
- presence of erythema nodosum, pyoderma gangrenosum, or aphthous ulcers;
- anal fissures, fistulae or abscesses;
- other fistulae; and/or
- fever during the previous week.

Remission of Crohn's disease is typically defined as a fall in the CDAI of less than 150 points. Severe disease is typically defined as a value of greater than 450 points. In certain aspects, response to a particular medication in a Crohn's disease patient is defined as a fall of the CDAI of greater than 70 points.

The terms "mucosal injury" or "mucosal damage" include the formation of macroscopically visible mucosal lesions in the intestines detectable during endoscopy, granuloma formation and disruption of the muscularis layer at the microscopic tissue level, epithelial apoptosis and infiltration of activated inflammatory and lymphocytic cells at the cellular level, increased epithelial permeability at a sub-cellular level, and gap junction disruption at a molecular level. In IBD such as Crohn's disease, the intestinal epithelium is damaged by the inflammatory environment, which results in the formation of refractory ulcers and lesions.

The term "mucosal healing" refers to restoration of normal mucosal appearance of a previously inflamed region, and complete absence of ulceration and inflammation at the endoscopic and microscopic levels. Mucosal healing includes repair and restoration of the mucosa, submucosa, and muscularis layers. It can also include neuronal and lymphangiogenic elements of the intestinal wall.

The term "nutrition-based therapy" includes butyrate, probiotics (e.g., VSL #3, *E. coli* Nissle 1917, bacterium bacillus polyfermenticus), vitamins, proteins, macromolecules, and/or chemicals that promote mucosal healing such as growth and turnover of intestinal mucosa.

III. Description of the Embodiments

The present invention provides methods for personalized therapeutic management of a disease in order to optimize therapy and/or monitor therapeutic efficacy. In particular, the present invention comprises measuring an array of one or a plurality of mucosal healing biomarkers at one or a plurality of time points over the course of therapy with a therapeutic agent to determine a mucosal healing index for selecting therapy, optimizing therapy, reducing toxicity, and/or monitoring the efficacy of therapeutic treatment. In certain instances, the therapeutic agent is a TNFα inhibitor for the treatment of a TNFα-mediated disease or disorder. In some embodiments, the methods of the present invention advantageously improve therapeutic management of patients with a TNFα-mediated disease or disorder by optimizing therapy and/or monitoring therapeutic efficacy to anti-TNF drugs such as anti-TNFα therapeutic antibodies.

As such, in one aspect, the present invention provides a method for personalized therapeutic management of a disease in order to optimize therapy or monitor therapeutic efficacy in a subject, the method comprising:

(a) measuring an array of mucosal healing markers at a plurality of time points over the course of therapy with a therapeutic antibody;

(b) generating the subject's mucosal healing index comprising a representation of the presence and/or concentration levels of each of the markers over time;

(c) comparing the subject's mucosal healing index to that of a control; and (d) selecting an appropriate therapy for the subject, to thereby achieve personalized therapeutic management of the disease in the subject.

As such, in another aspect, the present invention provides a method for personalized therapeutic management of a disease in order to select therapy in a subject, the method comprising:

(a) measuring an array of mucosal healing markers;

(b) generating the subject's mucosal healing index comprising a representation of the presence and/or concentration levels of each of the markers;

(c) comparing the subject's mucosal healing index to that of a control; and (d) selecting an appropriate therapy for the subject, to thereby achieve personalized therapeutic management of the disease in the subject.

As such, in one aspect, the present invention provides a method for optimizing therapy in a subject, the method comprising:

(a) measuring an array of mucosal healing markers at a plurality of time points over the course of therapy with a therapeutic antibody;

(b) applying a statistical algorithm to the level of the one or more markers determined in step (a) to generate a mucosal healing index;

(c) comparing the subject's mucosal healing index to that of a control; and (d) determining a subsequence dose of the course of therapy for the subject or whether a different course of therapy should be administered to the subject based upon the mucosal healing index.

As such, in one aspect, the present invention provides a method for selecting therapy in a subject, the method comprising:

(a) measuring an array of mucosal healing markers at a plurality of time points over the course of therapy with a therapeutic antibody;

(b) applying a statistical algorithm to the level of the one or more markers determined in step (a) to generate a mucosal healing index;

(c) comparing the subject's mucosal healing index to that of a control; and (d) selecting an appropriate course of therapy for the subject based upon the mucosal healing index.

As such, in another aspect, the present invention provides a method for reducing the risk of surgery in a subject diagnosed with IBD (e.g., Crohn's disease) being administered a therapy regimen (e.g., an anti-TNF antibody therapy regimen), the method comprising: (a) measuring an array of mucosal healing markers at a plurality of time points over the course of therapy with a therapeutic antibody;

(b) applying a statistical algorithm to the level of the one or more markers determined in step (a) to generate a mucosal healing index;

(c) comparing the subject's mucosal healing index to that of a control; and (d) determining whether the therapy regimen is reducing the subject's risk of surgery.

As such, in one aspect, the present invention provides a method for monitoring therapeutic efficiency in a subject receiving therapy (e.g., anti-TNF therapy), the method comprising:

(a) measuring an array of mucosal healing markers at a plurality of time points over the course of therapy with a therapeutic antibody;

(b) applying a statistical algorithm to the level of the one or more markers determined in step (a) to generate a mucosal healing index;

(c) comparing the subject's mucosal healing index to that of a control; and (d) determining whether the current course of therapy is appropriate for the subject based upon the mucosal healing index.

In some embodiments, the disease is a gastrointestinal disease or an autoimmune disease. In certain instances, the subject has inflammatory bowel disease (IBD, e.g., Crohn's disease (CD) or ulcerative colitis (UC)). In other instances, the subject has rheumatoid arthritis (RA). In preferred embodiments, the subject is a human.

In some embodiments, the therapy is selected from the group comprising an anti-TNF therapy, an immunosuppressive agent, a corticosteroid, a drug that targets a different mechanism, a nutrition therapy or combinations thereof. In certain instances, the anti-TNF therapy is a TNF inhibitor (e.g., anti-TNF drug, anti-TNFα antibody).

In other embodiments, the anti-TNF therapy is an anti-TNFα antibody. In some embodiments, the anti-TNFα antibody is a member selected from the group consisting of REMICADE™ (infliximab), ENBREL™ (etanercept), HUMIRA™ (adalimumab), CIMZIA® (certolizumab pegol), and combinations thereof. In preferred embodiments, the subject is a human.

In some embodiments, the therapy is an immunosuppressive agent. Non-limiting examples of immunosuppressive agents include thiopurine drugs such as azathioprine (AZA), 6-mercaptopurine (6-MP), and/or any metabolite thereof that has therapeutic efficacy and includes, without limitation, 6-thioguanine (6-TG), 6-methylmercaptopurine riboside, 6-thioinosine nucleotides (e.g., 6-thioinosine monophosphate, 6-thioinosine diphosphate, 6-thioinosine triphosphate), 6-thioguanine nucleotides (e.g., 6-thioguanosine monophosphate, 6-thioguanosine diphosphate, 6-thioguanosine triphosphate), 6-thioxanthosine nucleotides (e.g., 6-thioxanthosine monophosphate, 6-thioxanthosine diphosphate, 6-thioxanthosine triphosphate), derivatives thereof, analogues thereof, and combinations thereof; anti-metabolites such as methotrexate (MTX); sirolimus (rapamycin); temsirolimus; everolimus; tacrolimus (FK-506); FK-778; anti-lymphocyte globulin antibodies, anti-thymocyte globulin antibodies, anti-CD3 antibodies, anti-CD4 antibodies, and antibody-toxin conjugates; cyclosporine; mycophenolate; mizoribine monophosphate; scoparone; glatiramer acetate; metabolites thereof, pharmaceutically acceptable salts thereof; derivatives thereof; prodrugs thereof, and combinations thereof.

In other embodiments, the therapy is a corticosteroid. In yet other embodiments, the therapy is a drug that targets a different mechanism (e.g., a mechanism that is not mediated by the TNFα pathway). Non-limiting examples of a drug that targets a different mechanism include IL-6 receptor inhibiting monoclonal antibodies, anti-integrin molecules (e.g., natalizumab (Tysabri), vedolizumab), JAK-2 inhibitors, tyrosine kinase inhibitors, and combinations thereof.

In other embodiments, the therapy is a nutrition therapy. In particular embodiments, the nutrition therapy is a special carbohydrate diet. Special carbohydrate diet (SCD) is a strict grain-free, lactose-free, and sucrose-free nutritional regimen that was designed to reduce the symptoms of IBD such as Crohn's disease and ulcerative colitis. It has been shown that SCD can promote and/or maintain mucosal healing in patients with IBD (e.g., Crohn's disease or ulcerative colitis). Typically, SCD restricts the use of complex carbohydrates and eliminates refined sugar, grains and starch from the diet. It has been described that the microvilli of patients with IBD lack the ability to break down specific types of complex carbohydrates, resulting in the overgrowth of harmful bacteria and irritation of the gut mucosa. It has been recommended that SCD is a therapy for IBD (e.g., Crohn's disease or ulcerative colitis) because it enables the gut to undergo mucosal healing.

In some embodiments, the array of markers comprises a mucosal healing marker. In some embodiments, the mucosal marker comprises AREG, EREG, HB-EGF, HGF, NRG1, NRG2, NRG3, NRG4, BTC, EGF, IGF, TGF-α, VEGF-A, VEGF-B, VEGF-C, VEGF-D, FGF1, FGF2, FGF7, FGF9, TWEAK and combinations thereof.

In other embodiments, the array of markers further comprises a member selected from the group consisting of an anti-TNFα antibody, an anti-drug antibody (ADA), an inflammatory marker, an anti-inflammatory marker, a tissue repair marker (e.g., a growth factor), and combinations thereof. In certain instances, the anti-TNFα antibody is a member selected from the group consisting of REMICADE™ (infliximab), ENBREL™ (etanercept), HUMIRA™ (adalimumab), CIMZIA® (certolizumab pegol), and combinations thereof. In certain other instances, the anti-drug antibody (ADA) is a member selected from the group consisting of a human anti-chimeric antibody (HACA), a human anti-humanized antibody (HAHA), a human anti-mouse antibody (HAMA), and combinations thereof. In yet other instances, the inflammatory marker is a member selected from the group consisting of GM-CSF, IFN-γ, IL-1β, IL-2, IL-6, IL-8, TNF-α, sTNF RII, and combinations thereof. In further instances, the anti-inflammatory marker is a member selected from the group consisting of IL-12p70, IL-10, and combinations thereof.

In certain embodiments, the array comprises at least 2, 3, 4, 5, 6, 7, 8, 9, 10, 11, 12, 13, 14, 15, 16, 17, 18, 19, 20, 21, 22, 23, 24, 25, 30, 35, 40, 45, 50, or more markers. In some embodiments, the markers are measured in a biological sample selected from the group consisting of serum, plasma, whole blood, stool, peripheral blood mononuclear cells (PBMC), polymorphonuclear (PMN) cells, and a tissue biopsy (e.g., from a site of inflammation such as a portion of the gastrointestinal tract or synovial tissue).

In certain embodiments, the plurality of time points comprises at least 2, 3, 4, 5, 6, 7, 8, 9, 10, 11, 12, 13, 14, 15, 16, 17, 18, 19, 20, 25, 30, 35, 40, 45, 50, or more time points. In some instances, the first time point in the plurality of time points is prior to the course of therapy with the therapeutic antibody. In other instances, the first time point in the plurality of time points is during the course of therapy with the therapeutic antibody. As non-limiting examples, each of the markers can be measured prior to therapy with a therapeutic antibody and/or during the course of therapy at one or more (e.g., a plurality) of the following weeks: 1, 2, 3, 4, 5, 6, 7, 8, 9, 10, 11, 12, 13, 14, 15, 16, 17, 18, 19, 20, 22, 24, 26, 28, 30, 32, 34, 36, 38, 40, 42, 44, 46, 48, 50, 52, 54, 56, 58, 60, 62, 64, 66, 68, 70, 80, 90, 100, etc.

In further embodiments, the method for assessing or measuring mucosal healing further comprises comparing the determined level of the mucosal healing marker present in a sample to an index value or cutoff value or reference value or threshold value, wherein the level of the mucosal healing marker above or below that value is predictive or indicative of an increased or higher likelihood of the subject either undergoing mucosal healing or not undergoing mucosal healing. One skilled in the art will understand that the index value or cutoff value or reference value or threshold value is in units such as mg/ml, μg/ml, ng/ml, pg/ml, fg/ml, EU/ml, or U/ml depending on the marker of interest that is being measured.

In some embodiments, the mucosal healing index includes an empirically derived index that is based upon an analysis of a plurality of mucosal healing markers. In one aspect, the concentration of markers or their measured concentration values are transformed into an index by an algorithm resident on a computer. In certain aspects, the index is a synthetic or human derived output, score, or cut off value(s), which expresses the biological data in numerical terms. The index can be used to determine or make or aid in making a clinical decision. A mucosal healing index can be measured multiple times over the course of time. In one aspect, the algorithm can be trained with known samples and thereafter validated with samples of known identity.

In some embodiments, the mucosal healing index control is a mucosal healing index derived from a healthy individual, or an individual who has progressed from a disease state to a healthy state. Alternatively, the control can be an index representing a time course of a more diseased state or healthy to disease.

In some embodiments, the methods of determining the course of therapy and the like include the use of an empirically derived index, score or analysis to select for example, selecting a dose of drug, selecting an appropriate drug, or a course or length of therapy, a therapy regimen, or maintenance of an existing drug or dose. In certain aspects, a derived or measured index can be used to determine the course of therapy.

In some embodiments, mucosal healing can be assessed or monitored by endoscopy. Non-limiting examples of endoscopy include video capsule endoscopy (capsule endoscopy), disposable endoscopy, and 3D endoscopy. In other embodiment, the mucosal healing index is monitored or confirmed by endoscopy.

In some embodiments, selecting an appropriate therapy comprises maintaining, increasing, or decreasing a subsequent dose of the course of therapy for the subject. In other embodiments, the method further comprises determining a different course of therapy for the subject. In certain instances, the different course of therapy comprises treatment with a different anti-TNFα antibody. In other instances, the different course of therapy comprises the current course of therapy along with another therapeutic agent, such as, but not limited to, an immunosuppressive agent, a corticosteroid, a drug that targets a different mechanism, nutrition therapy, and combinations thereof).

In some embodiments, selecting an appropriate therapy comprises selecting an appropriate therapy for initial treatment. In some instances, the therapy comprises an anti-TNFα antibody therapy.

In certain embodiments, the methods disclosed herein can be used as confirmation that a proposed new drug or therapeutic is the same as or is sufficiently similar to an approved drug product, such that the proposed new drug can be used as a "biosimilar" therapeutic. For example, if the proposed new drug has only a slightly different disease activity profile compared to the branded drug product, this would be apparent using the methods disclosed herein. If the proposed new drug has a significantly different disease activity profile compared to the branded drug product, then the new drug would not be biosimilar. Advantageously, the methods disclosed herein can be used in clinical trials of proposed new drugs in order to assess the effective therapeutic value of the drug.

Accordingly, in some aspects, the methods of the invention provide information useful for guiding treatment decisions for patients receiving or about to receive anti-TNF drug therapy, e.g., by selecting an appropriate anti-TNF therapy for initial treatment, by determining when or how to adjust or modify (e.g., increase or decrease) the subsequent dose of an anti-TNF drug, by determining when or how to combine an anti-TNF drug (e.g., at an initial, increased, decreased, or same dose) with one or more immunosuppressive agents such as methotrexate (MTX) or azathioprine (AZA), and/or by determining when or how to change the current course of therapy (e.g., switch to a different anti-TNF drug or to a drug that targets a different mechanism such as an IL-6 receptor-inhibiting monoclonal antibody, anti-integrin molecule (e.g., Tysabri, Vedolizumab), JAK-2 inhibitor, and tyrosine kinase inhibitor, or to a nutrition therapy (e.g., special carbohydrate diet)).

In other embodiments, the methods of the present invention can be used to predict responsiveness to a TNFα inhibitor, especially to an anti-TNFα antibody in a subject having an autoimmune disorder (e.g., rheumatoid arthritis, Crohn's Disease, ulcerative colitis and the like.). In this method, by assaying the subject for the correct or therapeutic dose of anti-TNFα antibody, i.e., the therapeutic concentration level, it is possible to predict whether the individual will be responsive to the therapy.

In another embodiment, the present invention provides methods for monitoring IBD (e.g., Crohn's disease and ulcerative colitis) in a subject having the IBD disorder, wherein the method comprises assaying the subject for the correct or therapeutic dose of anti-TNFα antibody, i.e., the therapeutic concentration level, over time. In this manner, it is possible to predict whether the individual will be responsive to the therapy over the given time period.

In certain embodiments, step (a) comprises determining the presence and/or level of at least two, three, four, five, six, seven, eight, nine, ten, fifteen, twenty, thirty, forty, fifty, or more markers in the sample.

In other embodiments, the algorithm comprises a learning statistical classifier system. In some instances, the learning statistical classifier system is selected from the group consisting of a random forest, classification and regression tree, boosted tree, neural network, support vector machine, general chi-squared automatic interaction detector model, interactive tree, multiadaptive regression spline, machine learning classifier, and combinations thereof. In certain instances, the statistical algorithm comprises a single learning statistical classifier system. In certain other instances, the statistical algorithm comprises a combination of at least two learning statistical classifier systems. In some instances, the at least two learning statistical classifier systems are applied in tandem. Non-limiting examples of statistical algorithms and analysis suitable for use in the invention are described in International Application No. PCT/US2011/056777, filed Oct. 18, 2011, the disclosure of which is hereby incorporated by reference in its entirety for all purposes.

In other embodiments, step (b) further comprises applying a statistical algorithm to the presence and/or level of one or more mucosal healing markers determined at an earlier time during the course of therapy to generate an earlier mucosal healing index. In some instances, the earlier mucosal healing index is compared to the mucosal healing index generated in step (b) to determine a subsequent dose of the course of therapy or whether a different course of therapy should be administered. In certain embodiments, the subsequent dose of the course of therapy is increased, decreased, or maintained based upon mucosal healing index generated in step (b). In some instances, the different course of therapy comprises a different anti-TNFα antibody. In other instances, the different course of therapy comprises the current course of therapy along with an immunosuppressive agent.

In some embodiments, step (b) further comprises applying a statistical algorithm to the presence and/or level of one or more of the mucosal healing markers determined at an earlier time to generate an earlier disease activity/severity index. In certain instances, the mucosal healing index is compared to the mucosal healing index generated in step (b) to predict the course of the TNF-mediated disease or disorder.

In some embodiments, the method further comprises sending the results from the selection or determination of step (d) to a clinician. In other embodiments, step (d) comprises selecting an initial course of therapy for the subject.

Once the diagnosis or prognosis of a subject receiving anti-TNF drug therapy has been determined or the likelihood of response to an anti-TNF drug has been predicted in a subject diagnosed with a disease and disorder in which TNF has been implicated in the pathophysiology, e.g., but not limited to, shock, sepsis, infections, autoimmune diseases, RA, Crohn's disease, transplant rejection and graft-versus-host disease, according to the methods described herein, the present invention may further comprise recommending a course of therapy based upon the diagnosis, prognosis, or prediction. In certain instances, the present invention may further comprise administering to a subject a therapeutically effective amount of an anti-TNFα drug useful for treating one or more symptoms associated with the TNF-mediated disease or disorder. For therapeutic applications, the anti-TNF drug can be administered alone or co-administered in combination with one or more additional anti-TNF drugs and/or one or more drugs that reduce the side-effects associated with the anti-TNF drug (e.g., an immunosuppressive agent). As such, the present invention advantageously enables a clinician to practice "personalized medicine" by guiding treatment decisions and informing therapy selection and optimization for anti-TNFα drugs such that the right drug is given to the right patient at the right time.

The present invention is advantageous because it addresses and overcomes current limitations associated with the administration of anti-TNF drugs such as infliximab, in part, by providing information useful for guiding treatment decisions for those patients receiving or about to receive anti-TNF drug therapy. In particular, the methods of the present invention find utility for selecting an appropriate anti-TNF therapy for initial treatment, for determining when or how to adjust or modify (e.g., increase or decrease) the subsequent dose of an anti-TNF drug to optimize therapeutic efficacy and/or to reduce toxicity, for determining when or how to combine an anti-TNF drug (e.g., at an initial, increased, decreased, or same dose) with one or more immunosuppressive agents such as methotrexate (MTX) or azathioprine (AZA), and/or for determining when or how to change the current course of therapy (e.g., switch to a different anti-TNF drug or to a drug that targets a different mechanism).

Accordingly, the present invention is particularly useful in the following methods of improving patient management by guiding treatment decisions:

1. Crohn's disease prognostics: Treat patients most likely to benefit from therapy
2. Anti-therapeutic antibody monitoring (ATM)+Biomarker-based disease activity profiling 3. ATM sub-stratification
4. ATM with pharmacokinetic modeling
5. Monitor response and predict risk of relapse:
   a. Avoid chronic maintenance therapy in patients with low risk of recurrence
   b. Markers of mucosal healing
   c. Therapy selection: Whether to combine or not to combine anti-TNF drug therapy with an immunosuppressive agent such as MTX or AZA
6. Patient selection for biologics.

In some embodiments, the present invention provides a method for measuring an inflammatory index for Crohn's Disease management for an individual to optimize therapy, and predict response to the anti-TNF therapeutic, the method comprising:

(a) chromatographically measuring anti-TNF therapeutics and autoantibodies in a sample from the individual to determine their concentration levels;
(b) chromatographically measuring anti-TNF therapeutics and autoantibodies in a sample from the individual to determine their concentration levels;
(c) comparing the measured values to an efficacy scale to optimize therapy, and predict response to the anti-TNF therapeutic.

In some embodiments, the present invention provides a method for predicting the likelihood the concentration of an anti-TNF therapeutic during the course of treatment will fall below a threshold value, the method comprising:

(a) measuring a panel of markers selected from the group consisting of 1) GM-CSF; 2) IL-2; 3) TNF-α; 4) sTNFRII; and 5) the disease being situated in the small intestine; and
(b) predicting the likelihood the concentration of an anti-TNFα therapeutic will fall below the threshold based upon the concentration of the markers.

For the purpose of illustration only, Example 5 shows an exemplary embodiment of the present invention In particular, a method of predicting the likelihood the concentration of an anti-TNF treatment will fall below a threshold value.

In some embodiments, the present invention provides a method for predicting the likelihood the concentration of an anti-TNF therapeutic during the course of treatment will fall below a threshold value, the method comprising:

(a) measuring a panel of markers selected from the group consisting of 1) GM-CSF; 2) IL-2; 3) TNF-α; 4) sTNFRII; and 5) the disease being situated in the small intestine; and
(b) predicting the likelihood the concentration of an anti-TNF therapeutic will fall below the threshold based upon the concentration of the markers.

In other embodiments, the present invention provides a method for predicting the likelihood that anti-drug antibodies will occur in an individual on anti-TNF therapy, the method comprising:

(a) measuring a panel of markers selected from the group consisting of t EGF, VEGF, IL-8, CRP and VCAM-1; and
(b) predicting the likelihood that anti-drug antibodies will occur in an individual on anti-TNF therapy based on the concentration of marker levels.

For the purpose of illustration only, Example 4 is an exemplary embodiment of the present invention and demonstrates the detectin of anti-drug antibodies to infliximab (ATI).

In other embodiments, the present invention provides a method for monitoring an infliximab treatment regimen, the method comprising:

(a) measuring infliximab and antidrug antibodies to infliximab (ATI);
(b) measuring inflammatory markers CRP, SAA, ICAM, VCAM;
(c) measuring tissue repair marker VEGF; and
(d) correlating the measurements to therapeutic efficacy.

For the purpose of illustration only, Example 5 is an exemplary embodiment of the present invention and shows a method of monitoring an IFX treatment regimen.

In other embodiments, the present invention provides a method for determining whether an individual is a candidate for combination therapy wherein said individual is administered infliximab, the method comprising:

(a) measuring for the presence or absence of ATI in said individual; and
(b) administering an immunosuppressant (e.g., MTX) is the individual has significant levels of ATI.

In yet other embodiments, the method also includes measuring the concentration level of CRP which is indicative of the presence of ATI. For the purpose of illustration only, Examples 6 and 7 show that the presence and absence of ATI are predictive of responders and non-responders of Remicade therapy. Examples 6 and 7 are exemplary embodiments.

In yet other embodiments, the present invention provides a method for monitoring Crohn's disease activity, the method comprising:

(a) determining an inflammatory index comprising the measurement of a panel of markers comprising VEGF in μg/ml, CRP in ng/ml, SAA in ng/ml, ICAM in ng/ml and VCAM in ng/ml; and
(b) comparing the index to an efficacy scale to monitor and mange disease.

For the purpose of illustration only, Example 9 is an exemplary embodiment and shows use of the inflammatory index.

In particular embodiments, the present invention provides methods for determining the threshold of an anti-TNF drug such as IFX that can best discriminate disease activity as measured by C-reactive protein (CRP) levels. For the purpose of illustration only, Example 12 shows that IFX dichotomized at a threshold of 3 μg/ml can be differentiated by CRP. In certain instances, random IFX<3 and IFX≥3 μg/ml serum samples have higher CRP in IFX<3 μg/ml at a 74% rate (ROC AUC). Example 12 also shows that in ATI+ samples pairs, no significant difference in CRP between IFX groups (above and below 3 μg/ml) was observed. In particular, CRP levels were generally higher in ATI+ sample pairs, and CRP levels were higher in IFX<3 μg/ml for ATI− samples. Regression confirmed that CRP was positively related to ATI and negatively related to IFX. As such, the interaction corresponds to a CRP-IFX relationship that differs between ATI+ and ATI−.

IV. Mucosal Healing Index

The methods of the present invention comprise monitoring therapy response and predicting risk of relapse. In some embodiments, the methods include detecting, measuring and/or determining the presence and/or levels of markers of mucosal healing.

The gut mucosa plays a key role in barrier defense in addition to nutrient digestion, absorption and metabolism. The dynamic processes of intestinal epithelial cell proliferation, migration, and apoptosis are highly affected by general nutritional status, route of feeding, and adequacy of specific nutrients in the diet. However, with inflammatory diseases of the gut, mucosal cell impairment can result in mucosal injury or damage, thereby resulting in enhanced permeability to macromolecules, increased bacterial translocation from the lumen, and stimulation of epithelial cell apoptosis.

Mucosal injury is a multi-faceted physiological process spanning macroscopic to molecular levels. Mucosal injury includes the formation of macroscopically visible mucosal lesions detectable during endoscopy, granuloma formation and disruption of the muscularis layer at the microscopic tissue level, epithelial apoptosis and infiltration of activated inflammatory and lymphocytic cells at the cellular level, increased epithelial permeability at a sub-cellular level, and gap junction disruption at a molecular level.

Mucosal injury is likely initiated by a combination of endogenous and environmental factors. At first stage, it is believed that food-derived compounds, viral and bacterial-derived factors, as well as host-derived factors, may cause epithelial cell destruction and activation of innate and adaptive immunity. Damaged mucosa is initially infiltrated by diverse inflammatory cells consisting of neutrophils, eosinophils, mast cells, inflammatory monocytes, activated macrophages and dendritic cells. Specific adaptive immune responses toward the intestinal flora are generated leading to the later recruitment of activated B cells, CD4+ and CD8+ T cells to the inflamed mucosa. Neutrophils secrete elastase which can result in extracellular matrix degradation of the epithelium. Likewise, T cells, macrophages and intestinal fibroblasts express inflammatory factors such as IL-1, IL-2, IL-6, IL-14, IL-17, TGFβ and TNFα that lead to extracellular matrix degradation, epithelial damage, endothelial activation, and/or fibrosis stricture formation. Non-limiting examples of markers of mucosal injury include matrix metalloproteases (MMPs) and markers of oxidative stress (e.g., iNOS, reactive oxygen metabolites).

A. Array of Mucosal Healing Markers

A variety of mucosal markers including growth factors are particularly useful in the methods of the present invention for personalized therapeutic management by selecting therapy, optimizing therapy, reducing toxicity, and/or monitoring the efficacy of therapeutic treatment with one or more therapeutic agents such as biologics (e.g., anti-TNF drugs). In particular embodiments, the methods described herein utilize the determination of a mucosal healing index based upon one or more (a plurality of) mucosal healing markers such as growth factors (e.g., alone or in combination with biomarkers from other categories) to aid or assist in predicting disease course, selecting an appropriate anti-TNF drug therapy, optimizing anti-TNF drug therapy, reducing toxicity associated with anti-TNF drug therapy, and/or monitoring the efficacy of therapeutic treatment with an anti-TNF drug.

As such, in certain embodiments, the determination of the presence and/or level of one or more growth factors in a sample is useful in the present invention. As used herein, the term "growth factor" includes any of a variety of peptides, polypeptides, or proteins that are capable of stimulating cellular proliferation and/or cellular differentiation.

In some embodiments, mucosal healing markers include, but are not limited to, growth factors, inflammatory markers, cellular adhesion markers, cytokines, anti-inflammatory markers, matrix metalloproteinases, oxidative stress markers, and/or stress response markers.

In some embodiments, mucosal healing markers include growth factors. Non-limiting examples of growth factors include amphiregulin (AREG), epiregulin (EREG), heparin binding epidermal growth factor (HB-EGF), hepatocye growth factor (HGF), heregulin-31 (HRG) and isoforms, neuregulins (NRG1, NRG2, NRG3, NRG4), betacellulin (BTC), epidermal growth factor (EGF), insulin growth factor-1 (IGF-1), transforming growth factor (TGF), platelet-derived growth factor (PDGF), vascular endothelial growth factors (VEGF-A, VEGF-B, VEGF-C, VEGF-D), stem cell factor (SCF), platelet derived growth factor (PDGF), soluble fms-like tyrosine kinase 1 (sFlt1), placenta growth factor (PIGF, PLGF or PGF), fibroblast growth factors (FGF1, FGF2, FGF7, FGF9), and combinations thereof. In other embodiments, mucosal healing markers also include pigment epithelium-derived factor (PEDF, also known as SERPINF1), endothelin-1 (ET-1), keratinocyte growth factor (KGF; also known as FGF7), bone morphogenetic proteins (e.g., BMP1-BMP15), platelet-derived growth factor (PDGF), nerve growth factor (NGF), j-nerve growth factor (0-NGF), neurotrophic factors (e.g., brain-derived neurotrophic factor (BDNF), neurotrophin 3 (NT3), neurotrophin 4 (NT4), etc.), growth differentiation factor-9 (GDF-9), granulocyte-colony stimulating factor (G-CSF), granulocyte-macrophage colony stimulating factor (GM-CSF), myostatin (GDF-8), erythropoietin (EPO), thrombopoietin (TPO), and combinations thereof.

In other embodiments, mucosal healing markers also include cytokines. Non-limiting examples of cytokines that can be used to establish a mucosal healing index include bFGF, TNF-α, IL-10, IL-12(p70), IL-1β, IL-2, IL-6, GM-CSF, IL-13, IFN-γ, TGF-β1, TGF-02, TGF-β3, and combinations thereof. Non-limiting examples of cellular adhesion markers include SAA, CRP, ICAM, VCAM, and combinations thereof. Non-limiting examples of anti-inflammatory markers include IL-12p70, IL-10, and combinations thereof.

In some embodiments, mucosal healing markers include markers specific to the gastrointestinal tract including inflammatory markers and serology markers as described herein. Non-limiting examples include antibodies to bacterial antigens such as, e.g., OmpC, flagellins (cBir-1, Fla-A, Fla-X, etc.), 12, and others (pANCA, ASCA, etc.); anti-neutrophil antibodies, anti-*Saccharomyces cerevisiae* antibodies, and anti-microbiol antibodies.

The determination of markers of oxidative stress in a sample is also useful in the present invention. Non-limiting examples of markers of oxidative stress include those that are protein-based or DNA-based, which can be detected by measuring protein oxidation and DNA fragmentation, respectively. Other examples of markers of oxidative stress include organic compounds such as malondialdehyde.

Oxidative stress represents an imbalance between the production and manifestation of reactive oxygen species and a biological system's ability to readily detoxify the reactive intermediates or to repair the resulting damage. Disturbances in the normal redox state of tissues can cause toxic effects through the production of peroxides and free radicals that damage all components of the cell, including proteins, lipids, and DNA. Some reactive oxidative species can even act as messengers through a phenomenon called redox signaling.

In certain embodiments, derivatives of reactive oxidative metabolites (DROMs), ratios of oxidized to reduced glutathione (Eh GSH), and/or ratios of oxidized to reduced cysteine (Eh CySH) can be used to quantify oxidative stress. See, e.g., Neuman et al., *Clin. Chem.,* 53:1652-1657 (2007). Oxidative modifications of highly reactive cysteine residues in proteins such as tyrosine phosphatases and thioredoxin-related proteins can also be detected or measured using a technique such as, e.g., mass spectrometry (MS). See, e.g., Naito et al., *Anti-Aging Medicine,* 7 (5):36-44 (2010). Other markers of oxidative stress include protein-bound acrolein as described, e.g., in Uchida et al., *PNAS,* 95 (9) 4882-4887 (1998), the free oxygen radical test (FORT), which reflects levels of organic hydroperoxides, and the redox potential of the reduced glutathione/glutathione disulfide couple, (Eh) GSH/GSSG. See, e.g., Abramson et al., *Atherosclerosis,* 178(1):115-21 (2005).

In some embodiments, matrix metalloproteinases (MMPs) include members of a family of $Zn^{2+}$-dependent extracellular matrix (ECM) degrading endopeptidases that are able to degrade all types of ECM proteins. Non-limiting examples of MMPs include MMP-1, MMP-2, MMP-3, MMP-7, MMP-8, MMP-9, MMP-12, MMP-13, MT1-MMP-1, and combinations thereof. It has been shown that MMP-3 and MMP-9 are associated with mucosal injury and fistulae in CD patients (Baugh et al., *Gastroenterology,* 117: 814-822, (1999); Bailey et al., *J. Clin. Pathol.,* 47: 113-116 (1994)). In some embodiments, stress response markers include markers of oxidative stress, such as reactive oxygen species (ROS), superoxide dismutase (SOD), catalase (CAT), and glutathione, and markers of endoplasmic reticulum (ER) stress. Non-limiting examples of markers of oxidative stress include those that are protein-based or DNA-based, which can be detected by measuring protein oxidation and DNA fragmentation, respectively. In other embodiments, mucosal healing markers further include markers of oxidative DNA and/or protein damage. Non-limiting examples of ER stress markers include markers of unfolded protein response (e.g., ATF6, HSPA5, PDIA4, XBP1, IRE1, PERK, EIF2A, GADD34, GRP-78, phosphoylated INK, caspase-12, caspase-3, and combinations thereof).

The human amphiregulin (AREG) polypeptide sequence is set forth in, e.g., Genbank Accession Nos. NP_001648.1 and XP_001125684.1. The human AREG mRNA (coding) sequence is set forth in, e.g., Genbank Accession Nos. NM_001657.2 and XM_001125684.3. One skilled in the art will appreciate that AREG is also known as AR, colorectum cell-derived growth factor, CRDGF, SDGF, and AREGB.

The human epiregulin (EREG) polypeptide sequence is set forth in, e.g., Genbank Accession No. NP_001423.1. The human EREG mRNA (coding) sequence is set forth in, e.g., Genbank Accession No. NM_001432.2. One skilled in the art will appreciate that EREG is also known as EPR.

The human heparin-binding EGF-like growth factor (HB-EGF) polypeptide sequence is set forth in, e.g., Genbank Accession No. NP_001936.1. The human HB-EGF mRNA (coding) sequence is set forth in, e.g., Genbank Accession No. NM_001945.2. One skilled in the art will appreciate that HB-EGF is also known as diphtheria toxin receptor, DT-R, HBEGF, DTR, DTS, and HEGFL.

The human hepatocyte growth factor (HGF) polypeptide sequence is set forth in, e.g., Genbank Accession Nos. NP_000592.3, NP_001010931.1, NP_001010932.1, NP_001010933.1, and NP_001010934.1. The human HGF mRNA (coding) sequence is set forth in, e.g., Genbank Accession Nos. NM_000601.4, NM_001010931.1, NM_001010932.1, NM_001010933.1 and NM_001010934.1. One skilled in the art will appreciate that HGF is also known as scatter factor, SF, HPTA and hepatopoietin-A. One of skill will also appreciate that HGF includes to all isoform variants.

The human neuregulin-1 (NRG1) polypeptide sequence is set forth in, e.g., Genbank Accession Nos., NP 001153467.1, NP_001153471.1, NP_001153473.1, NP_001153477.1, NP 039250.2, NP_039251.2, NP 039252.2, NP_039253.1, NP 039254.1, NP_039256.2, and NP_039258.1. The human NRG1 mRNA (coding) sequence is set forth in, e.g., Genbank Accession No. NM_001159995.1, NM_001159999.1, NM_001160001.1, NM_001160005.1, NM_013956.3, NM_013957.3, NM_013958.3, NM_013959.3, NM_013960.3, NM_013962.2, and NM_013964.3. One skilled in the art will appreciate that NRG1 is also known as GGF, HGL, HRGA, NDF, SMDF, ARIA, acetylcholine receptor-inducing activity, breast cancer cell differentiation factor p45, glial growth factor, heregulin, HRG, neu differentiation factor, and sensory and motor neuron-derived factor. One of skill will also appreciate that NRG1 includes to all isoform variants.

The human neuregulin-2 (NRG2) polypeptide sequence is set forth in, e.g., Genbank Accession Nos. NP_001171864.1, NP_004874.1, NP_053584.1, NP_053585.1 and NP_053586.1. The human NRG2 mRNA (coding) sequence is set forth in, e.g., Genbank Accession Nos. NM_001184935.1, NM_004883.2, NM_013981.3, NM_013982.2 and NM_013983.2. One skilled in the art will appreciate that NRG2 is also known as NTAK, neural- and thymus-derived activator for ERBB kinases, DON-1, and divergent of neuregulin-1. One of skill will also appreciate that NRG2 includes to all isoform variants.

The human neuregulin-3 (NRG3) polypeptide sequence is set forth in, e.g., Genbank Accession Nos. NP_001010848.2 and NP_001159445.1. The human NRG3 mRNA (coding) sequence is set forth in, e.g., Genbank Accession Nos. NM_001010848.3 and NM_001165973.1. One skilled in the art will appreciate that NRG2 includes to all isoform variants.

The human neuregulin-4 (NRG4) polypeptide sequence is set forth in, e.g., Genbank Accession No. NP_612640.1. The human NRG4 mRNA (coding) sequence is set forth in, e.g., Genbank Accession No. NM_138573.3. One skilled in the art will appreciate that NRG4 includes to all isoform variants.

The human betacellulin (BTC) polypeptide sequence is set forth in, e.g., Genbank Accession No. NP_001720.1. The human BTC mRNA (coding) sequence is set forth in, e.g., Genbank Accession No. NM_001729.2. One skilled in the art will appreciate that BTC includes to all isoform variants.

The human epidermal growth factor (EGF) polypeptide sequence is set forth in, e.g., Genbank Accession Nos. NP_001954.2 and NP_001171602.1. The human EGF mRNA (coding) sequence is set forth in, e.g., Genbank Accession Nos. NM_001963.4 and NM_001178131.1. One skilled in the art will appreciate that EGF is also known as beta-urogastrone, urogastrone, URG, and HOMG4.

The human insulin-like growth factor (IGF) polypeptide sequence is set forth in, e.g., Genbank Accession Nos. NP_000609.1 and NP_001104755.1. The human IGF mRNA (coding) sequence is set forth in, e.g., Genbank Accession No. NM_000618.3 and NM_001111285.1. One skilled in the art will appreciate that IGF includes to all isoform variants. One skilled in the art will also appreciate that IGF is also known as mechano growth factor, MGF and somatomedin-C.

The human transforming growth factor alpha (TGF-$\alpha$) polypeptide sequence is set forth in, e.g., Genbank Accession Nos. NP_003227.1 and NP_001093161.1. The human TGF-$\alpha$, mRNA (coding) sequence is set forth in, e.g., Genbank Accession Nos. NM_003236.3 and NM_001099691.2. One skilled in the art will appreciate that TGF-$\alpha$, includes to all isoform variants. One skilled in the art will also appreciate that TGF-$\alpha$, is also known as EGF-like TGF, ETGF, and TGF type 1.

The human vascular endothelial growth factor (VEGF-A) polypeptide sequence is set forth in, e.g., Genbank Accession Nos. NP_001020537, NP_001020538, NP_001020539, NP_001020540, NP_001020541, NP_001028928, and NP_003367. The human VEGF-A mRNA (coding) sequence is set forth in, e.g., Genbank Accession No. NM_001025366, NM_001025367, NM_001025368, NM_001025369, NM_001025370, NM_001033756, and NM_003376. One skilled in the art will appreciate that VEGF-A is also known as VPF, VEGFA, VEGF, and MGC70609. One skilled in the art will appreciate that VEGF-A includes to all isoform variants.

The human vascular endothelial growth factor (VEGF-B) polypeptide sequence is set forth in, e.g., Genbank Accession Nos. NP_001230662, and NP_003368. The human VEGF-B mRNA (coding) sequence is set forth in, e.g., Genbank Accession Nos. NM_001243733 and NM_003377. One skilled in the art will appreciate that VEGF-B is also known as VEGFB, VEGF-related factor, and VRF. One skilled in the art will appreciate that VEGF-B includes to all isoform variants.

The human vascular endothelial growth factor (VEGF-C) polypeptide sequence is set forth in, e.g., Genbank Accession No. NP_005420. The human VEGF-C mRNA (coding) sequence is set forth in, e.g., Genbank Accession No. NM_005429. One skilled in the art will appreciate that VEGF-C is also known as Flt4 ligand, Flt4-L, VRP and vascular endothelial growth factor-realted protein. One skilled in the art will appreciate that VEGF-C includes to all isoform variants.

The human fibroblast growth factor 1 (FGF1) polypeptide sequence is set forth in, e.g., Genbank Accession Nos. NP_000791, NP_001138364, NP_001138406, NP_001138407, NP_001138407, NP_149127, and NP_149128. The human FGF1 mRNA (coding) sequence is set forth in, e.g., Genbank Accession Nos. NM_000800, NM_001144892, NM_001144934, NM_001144934, NM_001144935, NM_033136 and NM_033137. One skilled in the art will appreciate that FGF1 is also known as FGFA, FGF-1, acidic fibroblast growth factor, aFGF, endothelial cell growth factor, ECGF, heparin-binding growth factor 1, and HB-EGF1. One skilled in the art will appreciate that FGF1 includes to all isoform variants.

The human basic fibroblast growth factor (bFGF) polypeptide sequence is set forth in, e.g., Genbank Accession No. NP_001997.5. The human bFGF mRNA (coding) sequence is set forth in, e.g., Genbank Accession No. NM_002006.4. One skilled in the art will appreciate that bFGF is also known as FGF2, FGFB, and HBGF-2.

The human fibroblast growth factor 7 (FGF7) polypeptide sequence is set forth in, e.g., Genbank Accession No. NP_002000.1. The human FGF7 mRNA (coding) sequence is set forth in, e.g., Genbank Accession No. NM_002009.3. One skilled in the art will appreciate that FGF7 is also known as FGF-7, HBGF-7 and keratinocyte growth factor.

The human fibroblast growth factor 9 (FGF9) polypeptide sequence is set forth in, e.g., Genbank Accession No. NP_002001.1. The human FGF9 mRNA (coding) sequence is set forth in, e.g., Genbank Accession No. NM_002010.2. One skilled in the art will appreciate that FGF9 is also known as FGF-9, GAF, and HBGF-9.

The human TNF-related weak inducer of apoptosis (TWEAK) polypeptide sequence is set forth in, e.g., Genbank Accession No. NP_003800.1. The human TWEAK mRNA (coding) sequence is set forth in, e.g., Genbank Accession No. NM_003809.2. One skilled in the art will appreciate that TWEAK is also known as TNF12, APO3 ligand, APO3L, DR3LG, and UNQ181/PR0207.

In certain instances, the presence or level of a particular mucosal healing marker such as a growth factor is detected at the level of mRNA expression with an assay such as, for example, a hybridization assay or an amplification-based assay. In certain other instances, the presence or level of a particular growth factor is detected at the level of protein expression using, for example, an immunoassay (e.g., ELISA) or an immunohistochemical assay. In an exemplary embodiment, the presence or level of a particular growth factor is detected using a multiplexed immunoarray, such as a Collaborative Enzyme Enhanced Reactive ImmunoAssay (CEER), also known as the Collaborative Proximity Immunoassay (COPIA). CEER is described in the following patent documents which are herein incorporated by reference in their entirety for all purposes: PCT Publication No. WO 2008/036802; PCT Publication No. WO 2009/012140; PCT Publication No. WO 2009/108637; PCT Publication No. WO 2010/132723; PCT Publication No. WO 2011/008990; and PCT Application No. PCT/US2010/053386, filed Oct. 20, 2010. Suitable ELISA kits for determining the presence or level of a growth factor in a serum, plasma, saliva, or urine sample are available from, e.g., Antigenix America Inc. (Huntington Station, NY), Promega (Madison, WI), R&D Systems, Inc. (Minneapolis, MN), Invitrogen (Camarillo, CA), CHEMICON International, Inc. (Temecula, CA), Neogen Corp. (Lexington, KY), PeproTech (Rocky Hill, NJ), Alpco Diagnostics (Salem, NH), Pierce Biotechnology, Inc. (Rockford, IL), and/or Abazyme (Needham, MA).

In particular embodiments, at least one or a plurality (e.g., 2, 3, 4, 5, 6, 7, 8, 9, 10, 11, 12, 13, 14, 15, 16, 17, 18, 19, 20, or 21, such as, e.g., a panel or an array) of the following growth factor markers can be detected (e.g., alone or in combination with biomarkers from other categories) to aid or assist in predicting disease course, and/or to improve the accuracy of selecting therapy, optimizing therapy, reducing toxicity, and/or monitoring the efficacy of therapeutic treatment to anti-TNF drug therapy: AREG, EREG, HB-EGF, HGF, NRG1, NRG2, NRG3, NRG4, BTC, EGF, IGF, TGF-α, VEGF-A, VEGF-B, VEGF-C, VEGF-D, FGF1, FGF2, FGF7, FGF9, TWEAK and combinations thereof.

B. Mucosal Healing Index

In certain aspects, the present invention provides an algorithmic-based analysis of one or a plurality of (e.g., 2, 3, 4, 5, 6, 7, 8, 9, 10, 11, 12, 13, 14, 15, 16, 17, 18, 19, 20, 21, or more) mucosal healing markers to improve the accuracy of selecting therapy, optimizing therapy, reducing toxicity, and/or monitoring the efficacy of therapeutic treatment to anti-TNFα drug therapy.

A single statistical algorithm or a combination of two or more statistical algorithms described herein can then be applied to the presence or concentration level of the mucosal healing markers detected, measured, or determined in the sample to thereby select therapy, optimize therapy, reduce toxicity, or monitor the efficacy of therapeutic treatment with an anti-TNFα drug. As such, the methods of the invention find utility in determining patient management by determining patient immune status.

In some embodiments, the statistical algorithm comprises a learning statistical classifier system. In some instances, the learning statistical classifier system is selected from the group consisting of a random forest, classification and regression tree, boosted tree, neural network, support vector machine, general chi-squared automatic interaction detector model, interactive tree, multiadaptive regression spline, machine learning classifier, and combinations thereof. In certain instances, the statistical algorithm comprises a single learning statistical classifier system. In other embodiments, the statistical algorithm comprises a combination of at least two learning statistical classifier systems. In some instances, the at least two learning statistical classifier systems are applied in tandem. Non-limiting examples of statistical algorithms and analysis suitable for use in the invention are described in International Application No. PCT/US2011/056777, filed Oct. 18, 2011, the disclosure of which is hereby incorporated by reference in its entirety for all purposes.

Preferably, mucosal healing index is an empirically derived experimentally prepared index of values. In some instances, the index of values is transformed from an array of control measurements that were experimentally determined. In one aspect, the concentration of markers or their measured concentration values are transformed into an index by an algorithm resident on a computer. In certain aspects, the index is a synthetic or human derived output, score, or cut off value(s), which expresses the biological data in numerical terms. The index can be used to determine or make or aid in making a clinical decision. A mucosal healing index can be measured multiple times over the course of time. In one aspect, the algorithm can be trained with known samples and thereafter validated with samples of known identity.

In further embodiments, the method for assessing or measuring mucosal healing further comprises comparing the determined level of the mucosal healing marker present in a sample to an index value or cutoff value or reference value or threshold value, wherein the level of the mucosal healing marker above or below that value is predictive or indicative of an increased or higher likelihood of the subject either undergoing mucosal healing or not undergoing mucosal healing. One skilled in the art will understand that the index value or cutoff value or reference value or threshold value is in units such as mg/ml, μg/ml, ng/ml, μg/ml, fg/ml, EU/ml, or U/ml depending on the marker of interest that is being measured.

In some embodiments, the mucosal healing index control is a mucosal healing index derived from a healthy individual, or an individual who has progressed from a disease state to a healthy state. Alternatively, the control can be an index representing a time course of a more diseased state or healthy to disease.

In some embodiments, the methods of determining the course of therapy and the like include the use of an empirically derived index, score or analysis to select for example, selecting a dose of drug, selecting an appropriate drug, or a course or length of therapy, a therapy regimen, or maintenance of an existing drug or dose. In certain aspects, a derived or measured index can be used to determine the course of therapy.

Understanding the clinical course of disease will enable physicians to make better informed treatment decisions for their inflammatory disease patients (e.g., IBD, Crohn's disease or ulcerative colitis) and may help to direct new drug development in the future. The ideal mucosal healing marker (s) for use in the mucosal healing index described herein should be able to identify individuals at risk for the disease and should be disease-specific. Moreover, mucosal healing marker(s) should be able to detect disease activity and monitor the effect of treatment; and should have a predictive value towards relapse or recurrence of the disease. Predicting disease course, however, has now been expanded beyond just disease recurrence, but perhaps more importantly to include predictors of disease complications including surgery. The present invention is particularly advantageous because it provides indicators of mucosal healing and enables a prediction of the risk of relapse in those patients in remission. In addition, the mucosal healing markers and mucosal healing index of present invention have enormous implications for patient management as well as therapeutic decision-making and would aid or assist in directing the appropriate therapy to those patients who would most likely benefit from it and avoid the expense and potential toxicity of chronic maintenance therapy in those who have a low risk of recurrence.

I. Disease Activity Profile

As described herein, the disease activity profile (DAP) of the present invention can advantageously be used in methods for personalized therapeutic management of a disease in order to optimize therapy and/or monitor therapeutic efficacy. In certain embodiments, the methods of the invention can improve the accuracy of selecting therapy, optimizing therapy, reducing toxicity, and/or monitoring the efficacy of therapeutic treatment to anti-TNF drug therapy. In particular embodiments, the DAP is determined by measuring an array of one or a plurality of (e.g., 2, 3, 4, 5, 6, 7, 8, 9, 10, 11, 12, 13, 14, 15, 16, 17, 18, 19, 20, 21, 22, 23, 24, 25, 30, 35, 40, 45, 50, or more) markers at a plurality of time points over the course of therapy with a therapeutic antibody (e.g., anti-TNF drug) to determine a DAP, wherein the DAP comprises a representation of the concentration level of each marker over time. In certain embodiments, the DAP may comprise a representation of the presence or absence, concentration (e.g., expression) level, activation (e.g., phosphorylation) level, and/or velocity value (e.g., change in slope of the level of a particular marker) of each marker over time. As such, the methods of the present invention find utility in determining patient management by determining patient immune status.

In certain instances, a single statistical algorithm or a combination of two or more statistical algorithms can be applied to the concentration level of each marker over the course of therapy or to the DAP itself.

Understanding the clinical course of disease enables physicians to make better informed treatment decisions for their inflammatory disease patients (e.g., IBD (e.g., Crohn's disease), rheumatoid arthritis (RA), others) and helps to direct new drug development. The ideal biomarker(s) for use in the disease activity profile described herein is able to identify individuals at risk for the disease and is disease-specific. Moreover, the biomarker(s) are able to detect disease activity and monitor the effect of treatment; and have a predictive value towards relapse or recurrence of the disease. Predicting disease course, however, has now been expanded beyond just disease recurrence, but more importantly to include predictors of disease complications including surgery. The present invention is particularly advantageous because it provides indicators of disease activity and/or severity and enables a prediction of the risk of relapse in those patients in remission. In addition, the biomarkers and disease activity profile of the present invention have enormous implications for patient management, as well as therapeutic decision-making, and aid or assist in directing the appropriate therapy to patients who most likely will benefit from it and avoid the expense and potential toxicity of chronic maintenance therapy in those who have a low risk of recurrence.

As a non-limiting example, the disease activity profile (DAP) in one embodiment comprises detecting, measuring, or determining the presence, level (concentration (e.g., total) and/or activation (e.g., phosphorylation)), or genotype of one or more specific biomarkers in one or more of the following categories of biomarkers:

(1) Drug levels (e.g., anti-TNF drug levels);

(2) Anti-drug antibody (ADA) levels (e.g., level of autoantibody to an anti-TNF drug);

(3) Inflammatory markers;

(4) Anti-inflammatory markers; and/or (5) Tissue repair markers.

Non-limiting examples of additional and/or alternative markers in which the presence, level (concentration (e.g., total) and/or activation (e.g., phosphorylation)), or genotype can be measured include:

(6) Serology (e.g., immune markers);

(7) Markers of oxidative stress;

(8) Cell surface receptors (e.g., CD64, others);

(9) Signaling pathways;

(10) kel, or the elimination rate constant of a drug such as a therapeutic antibody (e.g., infliximab); and/or

(11) Other markers (e.g., genetic markers such as inflammatory pathway genes).

A. Anti-TNF Drug Levels & Anti-Drug Antibody (ADA) Levels

In some embodiments, the disease activity profile (DAP) comprises determining the presence and/or level of anti-TNF drug (e.g., level of free anti-TNFα therapeutic antibody such as infliximab) and/or anti-drug antibody (ADA) (e.g., level of autoantibody to the anti-TNF drug such as HACA) in a patient sample (e.g., a serum sample from a patient on anti-TNF drug therapy) at multiple time points, e.g., before, during, and/or after the course of therapy.

In particular embodiments, the presence and/or level of anti-TNF drug and/or ADA is determined with a homogeneous mobility shift assay using size exclusion chromatography. This method, which is described in PCT Application No. PCT/US2010/054125, filed Oct. 26, 2010, the disclosure of which is hereby incorporated by reference in its entirety for all purposes, is particularly advantageous for measuring the presence or level of TNFα inhibitors as well as autoantibodies (e.g., HACA, HAHA, etc.) that are generated against them.

In one embodiment, the method for detecting the presence of an anti-TNFα antibody in a sample comprises:

(a) contacting labeled TNFα with a sample having or suspected of having an anti-TNFα antibody to form a labeled complex with the anti-TNFα antibody;

(b) subjecting the labeled complex to size exclusion chromatography to separate the labeled complex; and (c) detecting the labeled complex, thereby detecting the anti-TNFα antibody.

In certain instances, the methods are especially useful for the following anti-TNFα antibodies: REMICADE™ (infliximab), ENBREL™ (etanercept), HUMIRA™ (adalimumab), and CIMZIA® (certolizumab pegol).

Tumor necrosis factor α (TNFα) is a cytokine involved in systemic inflammation and is a member of a group of cytokines that stimulate the acute phase reaction. The primary role of TNFα is in the regulation of immune cells. TNFα is also able to induce apoptotic cell death, to induce inflammation, and to inhibit tumorigenesis and viral replication. TNF is primarily produced as a 212-amino acid-long type II transmembrane protein arranged in stable homotrimers.

The terms "TNF", "TNFα," and "TNF-α," as used herein, are intended to include a human cytokine that exists as a 17 kDa secreted form and a 26 kDa membrane associated form, the biologically active form of which is composed of a trimer of noncovalently bound 17 kDa molecules. The structure of TNF-α is described further in, for example, Jones, et al. (1989) *Nature,* 338:225-228. The term TNF-α is intended to include human, a recombinant human TNF-α (rhTNF-α), or at least about 80% identity to the human TNFα protein. Human TNFα consists of a 35 amino acid (aa) cytoplasmic domain, a 21 aa transmembrane segment, and a 177 aa extracellular domain (ECD) (Pennica, D. et al. (1984) *Nature* 312:724). Within the ECD, human TNFα shares 97% aa sequence identity with rhesus and 71% 92% with bovine, canine, cotton rat, equine, feline, mouse, porcine, and rat TNFα. TNFα can be prepared by standard recombinant expression methods or purchased commercially (R & D Systems, Catalog No. 210-TA, Minneapolis, Minn.).

In certain instances, after the TNF a antibody is detected, the TNF a antibody is measured using a standard curve.

In another embodiment, the method for detecting an autoantibody to an anti-TNFα antibody in a sample comprises:

(a) contacting labeled anti-TNFα antibody with the sample to form a labeled complex with the autoantibody;

(b) subjecting the labeled complex to size exclusion chromatography to separate the labeled complex; and (c) detecting the labeled complex, thereby detecting the autoantibody.

In certain instances, the autoantibodies include human anti-chimeric antibodies (HACA), human anti-humanized antibodies (HAHA), and human anti-mouse antibodies (HAMA).

Non-limiting examples of other methods for determining the presence and/or level of anti-TNF drug and/or anti-drug antibodies (ADA) include enzyme-linked immunosorbent assays (ELISAs) such as bridging ELISAs. For example, the Infliximab ELISA from Matriks Biotek Laboratories detects free infliximab in serum and plasma samples, and the HACA ELISA from PeaceHealth Laboratories detects HACA in serum samples.

B. Inflammatory Markers

Although disease course of an inflammatory disease is typically measured in terms of inflammatory activity by noninvasive tests using white blood cell count, this method has a low specificity and shows limited correlation with disease activity.

As such, in certain embodiments, a variety of inflammatory markers, including biochemical markers, serological markers, protein markers, genetic markers, and/or other clinical or echographic characteristics, are particularly useful in the methods of the present invention for personalized therapeutic management by selecting therapy, optimizing therapy, reducing toxicity, and/or monitoring the efficacy of therapeutic treatment with one or more therapeutic agents such as biologics (e.g., anti-TNF drugs). In particular embodiments, the methods described herein utilize the determination of a disease activity profile (DAP) based upon one or more (a plurality of) inflammatory markers (e.g., alone or in combination with biomarkers from other categories) to aid or assist in predicting disease course, selecting an appropriate anti-TNF drug therapy, optimizing anti-TNF drug therapy, reducing toxicity associated with anti-TNF drug therapy, and/or monitoring the efficacy of therapeutic treatment with an anti-TNF drug.

Non-limiting examples of inflammatory markers include cytokines, chemokines, acute phase proteins, cellular adhesion molecules, S100 proteins, and/or other inflammatory markers. In preferred embodiments, the inflammatory markers comprise at least 1, 2, 3, 4, 5, 6, 7, 8, 9, 10, 15, 20, 25, or more cytokines. In one particular embodiment, the cytokines are at least 1, 2, 3, 4, 5, 6, 7, or all 8 of the following: GM-CSF, IFN-γ, IL-1β, IL-2, IL-6, IL-8, TNF-α, and sTNF RII.

1. Cytokines and Chemokines

The determination of the presence or level of at least one cytokine or chemokine in a sample is particularly useful in the present invention. As used herein, the term "cytokine" includes any of a variety of polypeptides or proteins secreted by immune cells that regulate a range of immune system functions and encompasses small cytokines such as chemokines. The term "cytokine" also includes adipocytokines, which comprise a group of cytokines secreted by adipocytes that function, for example, in the regulation of body weight, hematopoiesis, angiogenesis, wound healing, insulin resistance, the immune response, and the inflammatory response.

In certain embodiments, the presence or level of at least one cytokine including, but not limited to, granulocyte-macrophage colony-stimulating factor (GM-CSF), IFN-γ, IL-1β, IL-2, IL-6, IL-8, TNF-α, soluble tumor necrosis factor-α receptor II (sTNF RII), TNF-related weak inducer of apoptosis (TWEAK), osteoprotegerin (OPG), IFN-α, IFN-β, IL-1α, IL-1 receptor antagonist (IL-1ra), IL-4, IL-5, soluble IL-6 receptor (sIL-6R), IL-7, IL-9, IL-12, IL-13, IL-15, IL-17, IL-23, and IL-27 is determined in a sample.

In certain other embodiments, the presence or level of at least one chemokine such as, for example, CXCL1/GRO1/GROα, CXCL2/GRO2, CXCL3/GRO3, CXCL4/PF-4, CXCL5/ENA-78, CXCL6/GCP-2, CXCL7/NAP-2, CXCL9/MIG, CXCL10/IP-10, CXCL11/I-TAC, CXCL12/SDF-1, CXCL13/BCA-1, CXCL14/BRAK, CXCL15, CXCL16, CXCL17/DMC, CCL1, CCL2/MCP-1, CCL3/MIP-1α, CCL4/MIP-10, CCL5/RANTES, CCL6/C10, CCL7/MCP-3, CCL8/MCP-2, CCL9/CCL10, CCL11/Eotaxin, CCL12/MCP-5, CCL13/MCP-4, CCL14/HCC-1, CCL15/MIP-5, CCL16/LEC, CCL17/TARC, CCL18/MIP-4, CCL19/MIP-3β, CCL20/MIP-3α, CCL21/SLC, CCL22/MDC, CCL23/MPIF1, CCL24/Eotaxin-2, CCL25/TECK, CCL26/Eotaxin-3, CCL27/CTACK, CCL28/MEC, CL1, CL2, and $CX_3CL1$ is determined in a sample. In certain further embodiments, the presence or level of at least one adipocytokine including, but not limited to, leptin, adiponectin, resistin, active or total plasminogen activator inhibitor-1 (PAI-1), visfatin, and retinol binding protein 4 (RBP4) is determined in a sample. Preferably, the presence or level of GM-CSF, IFN-γ, IL-1β, IL-2, IL-6, IL-8, TNF-α, sTNF RII, and/or other cytokines or chemokines is determined.

In certain instances, the presence or level of a particular cytokine or chemokine is detected at the level of mRNA expression with an assay such as, for example, a hybridization assay or an amplification-based assay. In certain other instances, the presence or level of a particular cytokine or chemokine is detected at the level of protein expression using, for example, an immunoassay (e.g., ELISA) or an immunohistochemical assay. Suitable ELISA kits for determining the presence or level of a cytokine or chemokine of interest in a serum, plasma, saliva, or urine sample are available from, e.g., R&D Systems, Inc. (Minneapolis, MN), Neogen Corp. (Lexington, KY), Alpco Diagnostics (Salem, NH), Assay Designs, Inc. (Ann Arbor, MI), BD Biosciences Pharmingen (San Diego, CA), Invitrogen (Camarillo, CA), Calbiochem (San Diego, CA), CHEMICON International, Inc. (Temecula, CA), Antigenix America Inc. (Huntington Station, NY), QIAGEN Inc. (Valencia, CA), Bio-Rad Laboratories, Inc. (Hercules, CA), and/or Bender MedSystems Inc. (Burlingame, CA).

The human IL-6 polypeptide sequence is set forth in, e.g., Genbank Accession No. NP_000591. The human IL-6 mRNA (coding) sequence is set forth in, e.g., Genbank Accession No. NM_000600. One skilled in the art will appreciate that IL-6 is also known as interferon beta 2 (IFNB2), HGF, HSF, and BSF2.

The human IL-1βpolypeptide sequence is set forth in, e.g., Genbank Accession No. NP_000567. The human IL-1βmRNA (coding) sequence is set forth in, e.g., Genbank Accession No. NM_000576. One skilled in the art will appreciate that IL-1β is also known as IL1F2 and IL-1beta.

The human IL-8 polypeptide sequence is set forth in, e.g., Genbank Accession No. NP_000575. The human IL-8 mRNA (coding) sequence is set forth in, e.g., Genbank Accession No. NM_000584. One skilled in the art will appreciate that IL-8 is also known as CXCL8, K60, NAF, GCP1, LECT, LUCT, NAP1, 3-10C, GCP-1, LYNAP, MDNCF, MONAP, NAP-1, SCYB8, TSG-1, AMCF-I, and b-ENAP.

The human TWEAK polypeptide sequence is set forth in, e.g., Genbank Accession Nos. NP_003800 and AAC51923. The human TWEAK mRNA (coding) sequence is set forth in, e.g., Genbank Accession Nos. NM_003809 and BC104420. One skilled in the art will appreciate that TWEAK is also known as tumor necrosis factor ligand superfamily member 12 (TNFSF12), APO3 ligand (APO3L), CD255, DR3 ligand, growth factor-inducible 14 (Fn14) ligand, and UNQ181/PRO207.

2. Acute Phase Proteins

The determination of the presence or level of one or more acute-phase proteins in a sample is also useful in the present invention. Acute-phase proteins are a class of proteins whose plasma concentrations increase (positive acute-phase proteins) or decrease (negative acute-phase proteins) in response to inflammation. This response is called the acute-phase reaction (also called acute-phase response). Examples of positive acute-phase proteins include, but are not limited to, C-reactive protein (CRP), D-dimer protein, mannose-binding protein, alpha 1-antitrypsin, alpha 1-antichymotrypsin, alpha 2-macroglobulin, fibrinogen, prothrombin, factor VIII, von Willebrand factor, plasminogen, complement factors, ferritin, serum amyloid P component, serum amyloid A (SAA), orosomucoid (alpha 1-acid glycoprotein, AGP), ceruloplasmin, haptoglobin, and combinations thereof. Non-limiting examples of negative acute-phase proteins include albumin, transferrin, transthyretin, transcortin, retinol-binding protein, and combinations thereof. Preferably, the presence or level of CRP and/or SAA is determined.

In certain instances, the presence or level of a particular acute-phase protein is detected at the level of mRNA expression with an assay such as, for example, a hybridization assay or an amplification-based assay. In certain other instances, the presence or level of a particular acute-phase protein is detected at the level of protein expression using, for example, an immunoassay (e.g., ELISA) or an immunohistochemical assay. For example, a sandwich colorimetric ELISA assay available from Alpco Diagnostics (Salem, NH) can be used to determine the level of CRP in a serum, plasma, urine, or stool sample. Similarly, an ELISA kit available from Biomeda Corporation (Foster City, CA) can be used to detect CRP levels in a sample. Other methods for determining CRP levels in a sample are described in, e.g., U.S. Pat. Nos. 6,838,250 and 6,406,862; and U.S. Patent Publication Nos. 20060024682 and 20060019410. Additional methods for determining CRP levels include, e.g., immunoturbidimetry assays, rapid immunodiffusion assays, and visual agglutination assays. Suitable ELISA kits for determining the presence or level of SAA in a sample such as serum, plasma, saliva, urine, or stool are available from, e.g., Antigenix America Inc. (Huntington Station, NY), Abazyme (Needham, MA), USCN Life (Missouri City, TX), and/or U.S. Biological (Swampscott, MA).

C-reactive protein (CRP) is a protein found in the blood in response to inflammation (an acute-phase protein). CRP is typically produced by the liver and by fat cells (adipocytes). It is a member of the pentraxin family of proteins. The human CRP polypeptide sequence is set forth in, e.g., Genbank Accession No. NP_000558. The human CRP mRNA (coding) sequence is set forth in, e.g., Genbank Accession No. NM_000567. One skilled in the art will appreciate that CRP is also known as PTX1, MGC88244, and MGC149895.

Serum amyloid A (SAA) proteins are a family of apolipoproteins associated with high-density lipoprotein (HDL) in plasma. Different isoforms of SAA are expressed constitutively (constitutive SAAs) at different levels or in response to inflammatory stimuli (acute phase SAAs). These proteins are predominantly produced by the liver. The conservation of these proteins throughout invertebrates and vertebrates suggests SAAs play a highly essential role in all animals. Acute phase serum amyloid A proteins (A-SAAs) are secreted during the acute phase of inflammation. The human SAA polypeptide sequence is set forth in, e.g., Genbank Accession No. NP_000322. The human SAA mRNA (coding) sequence is set forth in, e.g., Genbank Accession No. NM_000331. One skilled in the art will appreciate that SAA is also known as PIG4, TP53I4, MGC111216, and SAA1.

3. Cellular Adhesion Molecules (IgSF CAMs)

The determination of the presence or level of one or more immunoglobulin superfamily cellular adhesion molecules in a sample is also useful in the present invention. As used herein, the term "immunoglobulin superfamily cellular adhesion molecule" (IgSF CAM) includes any of a variety of polypeptides or proteins located on the surface of a cell that have one or more immunoglobulin-like fold domains, and which function in intercellular adhesion and/or signal transduction. In many cases, IgSF CAMs are transmembrane proteins. Non-limiting examples of IgSF CAMs include Neural Cell Adhesion Molecules (NCAMs; e.g., NCAM-120, NCAM-125, NCAM-140, NCAM-145, NCAM-180, NCAM-185, etc.), Intercellular Adhesion Molecules (ICAMs, e.g., ICAM-1, ICAM-2, ICAM-3, ICAM-4, and ICAM-5), Vascular Cell Adhesion Molecule-1 (VCAM-1), Platelet-Endothelial Cell Adhesion Molecule-1 (PECAM-1), L1 Cell Adhesion Molecule (LICAM), cell adhesion molecule with homology to LiCAM (close homolog of L1) (CHL1), sialic acid binding Ig-like lectins (SIGLECs; e.g., SIGLEC-1, SIGLEC-2, SIGLEC-3, SIGLEC-4, etc.), Nectins (e.g., Nectin-1, Nectin-2, Nectin-3, etc.), and Nectin-like molecules (e.g., Necl-1, Necl-2, Necl-3, Necl-4, and Necl-5). Preferably, the presence or level of ICAM-1 and/or VCAM-1 is determined.

ICAM-1 is a transmembrane cellular adhesion protein that is continuously present in low concentrations in the membranes of leukocytes and endothelial cells. Upon cytokine stimulation, the concentrations greatly increase. ICAM-1 can be induced by IL-1 and TNFα and is expressed by the vascular endothelium, macrophages, and lymphocytes. In IBD, proinflammatory cytokines cause inflammation by upregulating expression of adhesion molecules such as ICAM-1 and VCAM-1. The increased expression of adhesion molecules recruit more lymphocytes to the infected tissue, resulting in tissue inflammation (see, Goke et al., *J., Gastroenterol.,* 32:480 (1997); and Rijcken et al., Gut, 51:529 (2002)). ICAM-1 is encoded by the intercellular adhesion molecule 1 gene (ICAM1; Entrez GeneID:3383; Genbank Accession No. NM_000201) and is produced after processing of the intercellular adhesion molecule 1 precursor polypeptide (Genbank Accession No. NP_000192).

VCAM-1 is a transmembrane cellular adhesion protein that mediates the adhesion of lymphocytes, monocytes, eosinophils, and basophils to vascular endothelium. Upregulation of VCAM-1 in endothelial cells by cytokines occurs as a result of increased gene transcription (e.g., in response to Tumor necrosis factor-alpha (TNFα) and Interleukin-1 (IL-1)). VCAM-1 is encoded by the vascular cell adhesion molecule 1 gene (VCAM1; Entrez GeneID:7412) and is produced after differential splicing of the transcript (Genbank Accession No. NM_001078 (variant 1) or NM_080682 (variant 2)), and processing of the precursor polypeptide splice isoform (Genbank Accession No. NP_001069 (isoform a) or NP_542413 (isoform b)).

In certain instances, the presence or level of an IgSF CAM is detected at the level of mRNA expression with an assay such as, for example, a hybridization assay or an amplification-based assay. In certain other instances, the presence or level of an IgSF CAM is detected at the level of protein expression using, for example, an immunoassay (e.g., ELISA) or an immunohistochemical assay. Suitable antibodies and/or ELISA kits for determining the presence or level of ICAM-1 and/or VCAM-1 in a sample such as a tissue sample, biopsy, serum, plasma, saliva, urine, or stool are available from, e.g., Invitrogen (Camarillo, CA), Santa Cruz Biotechnology, Inc. (Santa Cruz, CA), and/or Abcam Inc. (Cambridge, MA).

4. S100 Proteins

The determination of the presence or level of at least one S100 protein in a sample is also useful in the present invention. As used herein, the term "S100 protein" includes any member of a family of low molecular mass acidic proteins characterized by cell-type-specific expression and the presence of 2 EF-hand calcium-binding domains. There are at least 21 different types of S100 proteins in humans. The name is derived from the fact that S100 proteins are 100% soluble in ammonium sulfate at neutral pH. Most S100 proteins are homodimeric, consisting of two identical polypeptides held together by non-covalent bonds. Although S100 proteins are structurally similar to calmodulin, they differ in that they are cell-specific, expressed in particular cells at different levels depending on environmental factors. S-100 proteins are normally present in cells derived from the neural crest (e.g., Schwann cells, melanocytes, glial cells), chondrocytes, adipocytes, myoepithelial cells, macrophages, Langerhans cells, dendritic cells, and keratinocytes. S100 proteins have been implicated in a variety of intracellular and extracellular functions such as the regulation of protein phosphorylation, transcription factors, $Ca^{2+}$ homeostasis, the dynamics of cytoskeleton constituents, enzyme activities, cell growth and differentiation, and the inflammatory response.

Calgranulin is an S100 protein that is expressed in multiple cell types, including renal epithelial cells and neutrophils, and are abundant in infiltrating monocytes and granulocytes under conditions of chronic inflammation. Examples of calgranulins include, without limitation, calgranulin A (also known as S100A8 or MRP-8), calgranulin B (also known as S100A9 or MRP-14), and calgranulin C (also known as S100A12).

In certain instances, the presence or level of a particular S100 protein is detected at the level of mRNA expression with an assay such as, for example, a hybridization assay or an amplification-based assay. In certain other instances, the presence or level of a particular S100 protein is detected at the level of protein expression using, for example, an immunoassay (e.g., ELISA) or an immunohistochemical assay. Suitable ELISA kits for determining the presence or level of an S100 protein such as calgranulin A (S100A8), calgranulin B (S100A9), or calgranulin C (S100A12) in a serum, plasma, or urine sample are available from, e.g., Peninsula Laboratories Inc. (San Carlos, CA) and Hycult biotechnology b.v. (Uden, The Netherlands).

Calprotectin, the complex of S100A8 and S100A9, is a calcium- and zinc-binding protein in the cytosol of neutrophils, monocytes, and keratinocytes. Calprotectin is a major protein in neutrophilic granulocytes and macrophages and accounts for as much as 60% of the total protein in the cytosol fraction in these cells. It is therefore a surrogate marker of neutrophil turnover. Its concentration in stool correlates with the intensity of neutrophil infiltration of the intestinal mucosa and with the severity of inflammation. In some instances, calprotectin can be measured with an ELISA using small (50-100 mg) fecal samples (see, e.g., Johne et al., *Scand J Gastroenterol.,* 36:291-296 (2001)).

5. Other Inflammatory Markers

The determination of the presence or level of lactoferrin in a sample is also useful in the present invention. In certain instances, the presence or level of lactoferrin is detected at the level of mRNA expression with an assay such as, for example, a hybridization assay or an amplification-based assay. In certain other instances, the presence or level of lactoferrin is detected at the level of protein expression using, for example, an immunoassay (e.g., ELISA) or an immunohistochemical assay. A lactoferrin ELISA kit available from Calbiochem (San Diego, CA) can be used to detect human lactoferrin in a plasma, urine, bronchoalveolar lavage, or cerebrospinal fluid sample. Similarly, an ELISA kit available from U.S. Biological (Swampscott, MA) can be used to determine the level of lactoferrin in a plasma sample. U.S. Patent Publication No. 20040137536 describes an ELISA assay for determining the presence of elevated lactoferrin levels in a stool sample. Likewise, U.S. Patent Publication No. 20040033537 describes an ELISA assay for determining the concentration of endogenous lactoferrin in a stool, mucus, or bile sample. In some embodiments, then presence or level of anti-lactoferrin antibodies can be detected in a sample using, e.g., lactoferrin protein or a fragment thereof.

The determination of the presence or level of one or more pyruvate kinase isozymes such as M1-PK and M2-PK in a sample is also useful in the present invention. In certain instances, the presence or level of M1-PK and/or M2-PK is detected at the level of mRNA expression with an assay such as, for example, a hybridization assay or an amplification-based assay. In certain other instances, the presence or level of M1-PK and/or M2-PK is detected at the level of protein expression using, for example, an immunoassay (e.g., ELISA) or an immunohistochemical assay. Pyruvate kinase isozymes M1/M2 are also known as pyruvate kinase muscle isozyme (PKM), pyruvate kinase type K, cytosolic thyroid hormone-binding protein (CTHBP), thyroid hormone-binding protein 1 (THBP1), or opa-interacting protein 3 (OIP3).

In further embodiments, the determination of the presence or level of one or more growth factors in a sample is also useful in the present invention. Non-limiting examples of growth factors include transforming growth factors (TGF) such as TGF-$\alpha$, TGF-$\beta$, TGF-$\beta$2, TGF-$\beta$3, etc., which are described in detail below.

6. Exemplary Set of Inflammatory Markers

In particular embodiments, at least one or a plurality (e.g., two, three, four, five, six, seven, or all eight, such as, e.g., a panel or an array) of the following inflammatory markers can be detected (e.g., alone or in combination with biomarkers from other categories) to aid or assist in predicting disease course, and/or to improve the accuracy of selecting therapy, optimizing therapy, reducing toxicity, and/or monitoring the efficacy of therapeutic treatment to anti-TNF drug therapy: (1) GM-CSF; (2) IFN-$\gamma$; (3) IL-1$\beta$; (4) IL-2; (5) IL-6; (6) IL-8; (7) TNF-$\alpha$; and (8) sTNF RII.

C. Anti-Inflammatory Markers

In certain embodiments, a variety of anti-inflammatory markers are particularly useful in the methods of the present invention for personalized therapeutic management by selecting therapy, optimizing therapy, reducing toxicity, and/or monitoring the efficacy of therapeutic treatment with one or more therapeutic agents such as biologics (e.g., anti-TNF drugs). In particular embodiments, the methods described herein utilize the determination of a disease activity profile (DAP) based upon one or more (a plurality of) anti-inflammatory markers (e.g., alone or in combination with biomarkers from other categories) to aid or assist in predicting disease course, selecting an appropriate anti-TNF drug therapy, optimizing anti-TNF drug therapy, reducing toxicity associated with anti-TNF drug therapy, and/or monitoring the efficacy of therapeutic treatment with an anti-TNF drug.

Non-limiting examples of anti-inflammatory markers include IL-12p70 and IL-10. In preferred embodiments, the presence and/or concentration levels of both IL-12p70 and IL-10 are determined.

In certain instances, the presence or level of a particular anti-inflammatory marker is detected at the level of mRNA expression with an assay such as, for example, a hybridization assay or an amplification-based assay. In certain other instances, the presence or level of a particular anti-inflammatory marker is detected at the level of protein expression using, for example, an immunoassay (e.g., ELISA) or an immunohistochemical assay.

The human IL-12p70 polypeptide is a heterodimer made up of two subunits of IL-12 proteins: one is 40 kDa (IL-12p40) and one is 35 kDa (IL-12p35). Suitable ELISA kits for determining the presence or level of IL-12p70 in a serum, plasma, saliva, or urine sample are available from, e.g., Gen-Probe Diaclone SAS (France), Abazyme (Needham, MA), BD Biosciences Pharmingen (San Diego, CA), Cell Sciences (Canton, MA), eBioscience (San Diego, CA), Invitrogen (Camarillo, CA), R&D Systems, Inc. (Minneapolis, MN), and Thermo Scientific Pierce Protein Research Products (Rockford, IL).

The human IL-10 polypeptide is an anti-inflammatory cytokine that is also known as human cytokine synthesis inhibitory factor (CSIF). Suitable ELISA kits for determining the presence or level of IL-12p70 in a serum, plasma, saliva, or urine sample are available from, e.g., Antigenix America Inc. (Huntington Station, NY), BD Biosciences Pharmingen (San Diego, CA), Cell Sciences (Canton, MA), eBioscience (San Diego, CA), Gen-Probe Diaclone SAS (France), Invitrogen (Camarillo, CA), R&D Systems, Inc. (Minneapolis, MN), and Thermo Scientific Pierce Protein Research Products (Rockford, IL).

D. Serology (Immune Markers)

The determination of serological or immune markers such as autoantibodies in a sample (e.g., serum sample) is also useful in the present invention. Antibodies against anti-inflammatory molecules such as IL-10, TGF-$\beta$, and others might suppress the body's ability to control inflammation and the presence or level of these antibodies in the patient indicates the use of powerful immunosuppressive medications such as anti-TNF drugs. Mucosal healing might result in a decrease in the antibody titre of antibodies to bacterial antigens such as, e.g., OmpC, flagellins (cBir-1, Fla-A, Fla-X, etc.), 12, and others (pANCA, ASCA, etc.).

As such, in certain aspects, the methods described herein utilize the determination of a disease activity profile (DAP) based upon one or more (a plurality of) serological or immune markers (e.g., alone or in combination with biomarkers from other categories) to aid or assist in predicting disease course, selecting an appropriate anti-TNF drug therapy, optimizing anti-TNF drug therapy, reducing toxicity associated with anti-TNF drug therapy, and/or monitoring the efficacy of therapeutic treatment with an anti-TNF drug.

Non-limiting examples of serological immune markers suitable for use in the present invention include anti-neutrophil antibodies, anti-*Saccharomyces cerevisiae* antibodies, and/or other anti-microbial antibodies.

1. Anti-Neutrophil Antibodies

The determination of ANCA levels and/or the presence or absence of pANCA in a sample is useful in the methods of the present invention. As used herein, the term "anti-neutrophil cytoplasmic antibody" or "ANCA" includes antibodies directed to cytoplasmic and/or nuclear components of neutrophils. ANCA activity can be divided into several broad categories based upon the ANCA staining pattern in neutrophils: (1) cytoplasmic neutrophil staining without perinuclear highlighting (cANCA); (2) perinuclear staining around the outside edge of the nucleus (pANCA); (3) perinuclear staining around the inside edge of the nucleus (NSNA); and (4) diffuse staining with speckling across the entire neutrophil (SAPPA). In certain instances, pANCA staining is sensitive to DNase treatment. The term ANCA encompasses all varieties of anti-neutrophil reactivity, including, but not limited to, cANCA, pANCA, NSNA, and SAPPA. Similarly, the term ANCA encompasses all immunoglobulin isotypes including, without limitation, immunoglobulin A and G.

ANCA levels in a sample from an individual can be determined, for example, using an immunoassay such as an enzyme-linked immunosorbent assay (ELISA) with alcohol-fixed neutrophils. The presence or absence of a particular category of ANCA such as pANCA can be determined, for example, using an immunohistochemical assay such as an indirect fluorescent antibody (IFA) assay. Preferably, the presence or absence of pANCA in a sample is determined using an immunofluorescence assay with DNase-treated, fixed neutrophils. In addition to fixed neutrophils, antigens specific for ANCA that are suitable for determining ANCA levels include, without limitation, unpurified or partially purified neutrophil extracts; purified proteins, protein fragments, or synthetic peptides such as histone H1 or ANCA-reactive fragments thereof (see, e.g., U.S. Pat. No. 6,074,835); histone H1-like antigens, porin antigens, Bacteroides antigens, or ANCA-reactive fragments thereof (see, e.g., U.S. Pat. No. 6,033,864); secretory vesicle antigens or ANCA-reactive fragments thereof (see, e.g., U.S. patent application Ser. No. 08/804,106); and anti-ANCA idiotypic antibodies. One skilled in the art will appreciate that the use of additional antigens specific for ANCA is within the scope of the present invention.

2. Anti-*Saccharomyces cerevisiae* Antibodies

The determination of ASCA (e.g., ASCA-IgA and/or ASCA-IgG) levels in a sample is useful in the present invention. As used herein, the term "anti-*Saccharomyces cerevisiae* immunoglobulin A" or "ASCA-IgA" includes antibodies of the immunoglobulin A isotype that react specifically with *S. cerevisiae*. Similarly, the term "anti-*Saccharomyces cerevisiae* immunoglobulin G" or "ASCA-IgG" includes antibodies of the immunoglobulin G isotype that react specifically with *S. cerevisiae*.

The determination of whether a sample is positive for ASCA-IgA or ASCA-IgG is made using an antigen specific for ASCA. Such an antigen can be any antigen or mixture of antigens that is bound specifically by ASCA-IgA and/or ASCA-IgG. Although ASCA antibodies were initially characterized by their ability to bind *S. cerevisiae*, those of skill in the art will understand that an antigen that is bound specifically by ASCA can be obtained from *S. cerevisiae* or from a variety of other sources so long as the antigen is capable of binding specifically to ASCA antibodies. Accordingly, exemplary sources of an antigen specific for ASCA, which can be used to determine the levels of ASCA-IgA and/or ASCA-IgG in a sample, include, without limitation, whole killed yeast cells such as *Saccharomyces* or *Candida* cells; yeast cell wall mannan such as phosphopeptidomannan (PPM); oligosachharides such as oligomannosides; neoglycolipids; anti-ASCA idiotypic antibodies; and the like. Different species and strains of yeast, such as *S. cerevisiae* strain Su1, Su2, CBS 1315, or BM 156, or *Candida albicans* strain VW32, are suitable for use as an antigen specific for ASCA-IgA and/or ASCA-IgG. Purified and synthetic antigens specific for ASCA are also suitable for use in determining the levels of ASCA-IgA and/or ASCA-IgG in a sample. Examples of purified antigens include, without limitation, purified oligosaccharide antigens such as oligomannosides. Examples of synthetic antigens include, without limitation, synthetic oligomannosides such as those described in U.S. Patent Publication No. 20030105060, e.g., D-Man β(1-2) D-Man β(1-2) D-Man β(1-2) D-Man-OR, D-Man α(1-2) D-Man α(1-2) D-Man α(1-2) D-Man-OR, and D-Man α(1-3) D-Man α(1-2) D-Man α(1-2) D-Man-OR, wherein R is a hydrogen atom, a $C_1$ to $C_{20}$ alkyl, or an optionally labeled connector group.

Preparations of yeast cell wall mannans, e.g., PPM, can be used in determining the levels of ASCA-IgA and/or ASCA-IgG in a sample. Such water-soluble surface antigens can be prepared by any appropriate extraction technique known in the art, including, for example, by autoclaving, or can be obtained commercially (see, e.g., Lindberg et al., Gut, 33:909-913 (1992)). The acid-stable fraction of PPM is also useful in the present invention (Sendid et al., *Clin. Diag. Lab. Immunol.,* 3:219-226 (1996)). An exemplary PPM that is useful in determining ASCA levels in a sample is derived from *S. uvarum* strain ATCC #38926.

Purified oligosaccharide antigens such as oligomannosides can also be useful in determining the levels of ASCA-IgA and/or ASCA-IgG in a sample. The purified oligomannoside antigens are preferably converted into neoglycolipids as described in, for example, Faille et al., *Eur. J. Microbiol. Infect. Dis.,* 11:438-446 (1992). One skilled in the art understands that the reactivity of such an oligomannoside antigen with ASCA can be optimized by varying the mannosyl chain length (Frosh et al., *Proc Natl. Acad. Sci. USA,* 82:1194-1198 (1985)); the anomeric configuration (Fukazawa et al., In "Immunology of Fungal Disease," E. Kurstak (ed.), Marcel Dekker Inc., New York, pp. 37-62 (1989); Nishikawa et al., *Microbiol. Immunol.,* 34:825-840 (1990); Poulain et al., *Eur. J. Clin. Microbiol.,* 23:46-52 (1993); Shibata et al., *Arch. Biochem. Biophys.,* 243:338-348

(1985); Trinel et al., *Infect. Immun.*, 60:3845-3851 (1992)); or the position of the linkage (Kikuchi et al., *Planta*, 190:525-535 (1993)).

Suitable oligomannosides for use in the methods of the present invention include, without limitation, an oligomannoside having the mannotetraose Man(1-3) Man(1-2) Man (1-2) Man. Such an oligomannoside can be purified from PPM as described in, e.g., Faille et al., supra. An exemplary neoglycolipid specific for ASCA can be constructed by releasing the oligomannoside from its respective PPM and subsequently coupling the released oligomannoside to 4-hexadecylaniline or the like.

3. Anti-Microbial Antibodies

The determination of anti-OmpC antibody levels in a sample is also useful in the present invention. As used herein, the term "anti-outer membrane protein C antibody" or "anti-OmpC antibody" includes antibodies directed to a bacterial outer membrane porin as described in, e.g., PCT Patent Publication No. WO 01/89361. The term "outer membrane protein C" or "OmpC" refers to a bacterial porin that is immunoreactive with an anti-OmpC antibody.

The level of anti-OmpC antibody present in a sample from an individual can be determined using an OmpC protein or a fragment thereof such as an immunoreactive fragment thereof. Suitable OmpC antigens useful in determining anti-OmpC antibody levels in a sample include, without limitation, an OmpC protein, an OmpC polypeptide having substantially the same amino acid sequence as the OmpC protein, or a fragment thereof such as an immunoreactive fragment thereof. As used herein, an OmpC polypeptide generally describes polypeptides having an amino acid sequence with greater than about 50% identity, preferably greater than about 60% identity, more preferably greater than about 70% identity, still more preferably greater than about 80%, 85%, 90%, 95%, 96%, 97%, 98%, or 99% amino acid sequence identity with an OmpC protein, with the amino acid identity determined using a sequence alignment program such as CLUSTALW. Such antigens can be prepared, for example, by purification from enteric bacteria such as *E. coli*, by recombinant expression of a nucleic acid such as Genbank Accession No. K00541, by synthetic means such as solution or solid phase peptide synthesis, or by using phage display.

The determination of anti-I2 antibody levels in a sample is also useful in the present invention. As used herein, the term "anti-I2 antibody" includes antibodies directed to a microbial antigen sharing homology to bacterial transcriptional regulators as described in, e.g., U.S. Pat. No. 6,309,643. The term "I2" refers to a microbial antigen that is immunoreactive with an anti-I2 antibody. The microbial I2 protein is a polypeptide of 100 amino acids sharing some similarity weak homology with the predicted protein 4 from *C. pasteurianum*, Rv3557c from *Mycobacterium tuberculosis*, and a transcriptional regulator from *Aquifex aeolicus*. The nucleic acid and protein sequences for the I2 protein are described in, e.g., U.S. Pat. No. 6,309,643.

The level of anti-I2 antibody present in a sample from an individual can be determined using an I2 protein or a fragment thereof such as an immunoreactive fragment thereof. Suitable I2 antigens useful in determining anti-I2 antibody levels in a sample include, without limitation, an I2 protein, an I2 polypeptide having substantially the same amino acid sequence as the I2 protein, or a fragment thereof such as an immunoreactive fragment thereof. Such I2 polypeptides exhibit greater sequence similarity to the I2 protein than to the *C. pasteurianum* protein 4 and include isotype variants and homologs thereof. As used herein, an I2 polypeptide generally describes polypeptides having an amino acid sequence with greater than about 50% identity, preferably greater than about 60% identity, more preferably greater than about 70% identity, still more preferably greater than about 80%, 85%, 90%, 95%, 96%, 97%, 98%, or 99% amino acid sequence identity with a naturally-occurring I2 protein, with the amino acid identity determined using a sequence alignment program such as CLUSTALW. Such I2 antigens can be prepared, for example, by purification from microbes, by recombinant expression of a nucleic acid encoding an I2 antigen, by synthetic means such as solution or solid phase peptide synthesis, or by using phage display.

The determination of anti-flagellin antibody levels in a sample is also useful in the present invention. As used herein, the term "anti-flagellin antibody" includes antibodies directed to a protein component of bacterial flagella as described in, e.g., PCT Patent Publication No. WO 03/053220 and U.S. Patent Publication No. 20040043931. The term "flagellin" refers to a bacterial flagellum protein that is immunoreactive with an anti-flagellin antibody. Microbial flagellins are proteins found in bacterial flagellum that arrange themselves in a hollow cylinder to form the filament.

The level of anti-flagellin antibody present in a sample from an individual can be determined using a flagellin protein or a fragment thereof such as an immunoreactive fragment thereof. Suitable flagellin antigens useful in determining anti-flagellin antibody levels in a sample include, without limitation, a flagellin protein such as Cbir-1 flagellin, flagellin X, flagellin A, flagellin B, fragments thereof, and combinations thereof, a flagellin polypeptide having substantially the same amino acid sequence as the flagellin protein, or a fragment thereof such as an immunoreactive fragment thereof. As used herein, a flagellin polypeptide generally describes polypeptides having an amino acid sequence with greater than about 50% identity, preferably greater than about 60% identity, more preferably greater than about 70% identity, still more preferably greater than about 80%, 85%, 90%, 95%, 96%, 97%, 98%, or 99% amino acid sequence identity with a naturally-occurring flagellin protein, with the amino acid identity determined using a sequence alignment program such as CLUSTALW. Such flagellin antigens can be prepared, e.g., by purification from bacterium such as *Helicobacter Bilis, Helicobacter mustelae, Helicobacter pylori, Butyrivibrio fibrisolvens*, and bacterium found in the cecum, by recombinant expression of a nucleic acid encoding a flagellin antigen, by synthetic means such as solution or solid phase peptide synthesis, or by using phage display.

E. Cell Surface Receptors

The determination of cell surface receptors in a sample is also useful in the present invention. The half-life of anti-TNF drugs such as Remicade and Humira is significantly decreased in patients with a high level of inflammation. CD64, the high-affinity receptor for immunoglobulin (Ig) G1 and IgG3, is predominantly expressed by mononuclear phagocytes. Resting polymorphonuclear (PMN) cells scarcely express CD64, but the expression of this marker is upregulated by interferon and granulocyte-colony-stimulating factor acting on myeloid precursors in the bone marrow. Crosslinking of CD64 with IgG complexes exerts a number of cellular responses, including the internalization of immune complexes by endocytosis, phagocytosis of opsonized particles, degranulation, activation of the oxidative burst, and the release of cytokines.

As such, in certain aspects, the methods described herein utilize the determination of a disease activity profile (DAP)

based upon one or more (a plurality of) cell surface receptors such as CD64 (e.g., alone or in combination with biomarkers from other categories) to aid or assist in predicting disease course, selecting an appropriate anti-TNF drug therapy, optimizing anti-TNF drug therapy, reducing toxicity associated with anti-TNF drug therapy, and/or monitoring the efficacy of therapeutic treatment with an anti-TNF drug.

F. Signaling Pathways

The determination of signaling pathways in a sample is also useful in the present invention. Polymorphonuclear (PMN) cell activation, followed by infiltration into the intestinal mucosa (synovium for RA) and migration across the crypt epithelium is regarded as a key feature of IBD. It has been estimated by fecal indium-111-labeled leukocyte excretion that migration of PMN cells from the circulation to the diseased section of the intestine is increased by 10-fold or more in IBD patients. Thus, measuring activation of PMN cells from blood or tissue inflammation by measuring signaling pathways using an assay such as the Collaborative Enzyme Enhanced Reactive ImmunoAssay (CEER) described herein is an ideal way to understand inflammatory disease.

As such, in certain aspects, the methods described herein utilize the determination of a disease activity profile (DAP) based upon one or more (a plurality of) signal transduction molecules in one or more signaling pathways (e.g., alone or in combination with biomarkers from other categories) to aid or assist in predicting disease course, selecting an appropriate anti-TNF drug therapy, optimizing anti-TNF drug therapy, reducing toxicity associated with anti-TNF drug therapy, and/or monitoring the efficacy of therapeutic treatment with an anti-TNF drug. In preferred embodiments, the total (e.g., expression) level and/or activation (e.g., phosphorylation) level of one or more signal transduction molecules in one or more signaling pathways is measured.

The term "signal transduction molecule" or "signal transducer" includes proteins and other molecules that carry out the process by which a cell converts an extracellular signal or stimulus into a response, typically involving ordered sequences of biochemical reactions inside the cell. Examples of signal transduction molecules include, but are not limited to, receptor tyrosine kinases such as EGFR (e.g., EGFR/HER1/ErbB1, HER2/Neu/ErbB2, HER3/ErbB3, HER4/ErbB4), VEGFR1/FLT1, VEGFR2/FLK1/KDR, VEGFR3/FLT4, FLT3/FLK2, PDGFR (e.g., PDGFRA, PDGFRB), c-KIT/SCFR, INSR (insulin receptor), IGF-IR, IGF-IIR, IRR (insulin receptor-related receptor), CSF-1R, FGFR 1-4, HGFR 1-2, CCK4, TRK A-C, c-MET, RON, EPHA 1-8, EPHB 1-6, AXL, MER, TYRO3, TIE 1-2, TEK, RYK, DDR 1-2, RET, c-ROS, V-cadherin, LTK (leukocyte tyrosine kinase), ALK (anaplastic lymphoma kinase), ROR 1-2, MUSK, AATYK 1-3, and RTK 106; truncated forms of receptor tyrosine kinases such as truncated HER2 receptors with missing amino-terminal extracellular domains (e.g., p95ErbB2 (p95m), p110, p95c, p95n, etc.), truncated cMET receptors with missing amino-terminal extracellular domains, and truncated HER3 receptors with missing amino-terminal extracellular domains; receptor tyrosine kinase dimers (e.g., p95HER2/HER3; p95HER2/HER2; truncated HER3 receptor with HER1, HER2, HER3, or HER4; HER2/HER2; HER3/HER3; HER2/HER3; HER1/HER2; HER1/HER3; HER2/HER4; HER3/HER4; etc.); non-receptor tyrosine kinases such as BCR-ABL, Src, Frk, Btk, Csk, Abl, Zap70, Fes/Fps, Fak, Jak, Ack, and LIMK; tyrosine kinase signaling cascade components such as AKT (e.g., AKT1, AKT2, AKT3), MEK (MAP2K1), ERK2 (MAPK1), ERK1 (MAPK3), PI3K (e.g., PIK3CA (p110), PIK3R1 (p85)), PDK1, PDK2, phosphatase and tensin homolog (PTEN), SGK3, 4E-BP1, P70S6K (e.g., p70 S6 kinase splice variant alpha I), protein tyrosine phosphatases (e.g., PTP1B, PTPN13, BDP1, etc.), RAF, PLA2, MEKK, JNKK, JNK, p38, She (p66), Ras (e.g., K-Ras, N-Ras, H-Ras), Rho, Rac1, Cdc42, PLC, PKC, p53, cyclin D1, STAT1, STAT3, phosphatidylinositol 4,5-bisphosphate (PIP2), phosphatidylinositol 3,4,5-trisphosphate (PIP3), mTOR, BAD, p21, p27, ROCK, IP3, TSP-1, NOS, GSK-3β, RSK 1-3, JNK, c-Jun, Rb, CREB, Ki67, paxillin, NF-kB, and IKK; nuclear hormone receptors such as estrogen receptor (ER), progesterone receptor (PR), androgen receptor, glucocorticoid receptor, mineralocorticoid receptor, vitamin A receptor, vitamin D receptor, retinoid receptor, thyroid hormone receptor, and orphan receptors; nuclear receptor coactivators and repressors such as amplified in breast cancer-1 (AIB1) and nuclear receptor corepressor 1 (NCOR), respectively; and combinations thereof.

The term "activation state" refers to whether a particular signal transduction molecule is activated. Similarly, the term "activation level" refers to what extent a particular signal transduction molecule is activated. The activation state typically corresponds to the phosphorylation, ubiquitination, and/or complexation status of one or more signal transduction molecules. Non-limiting examples of activation states (listed in parentheses) include: HER1/EGFR (EGFRvIII, phosphorylated (p-) EGFR, EGFR:Shc, ubiquitinated (u-) EGFR, p-EGFRvIII); ErbB2 (p-ErbB2, p95HER2 (truncated ErbB2), p-p95HER2, ErbB2:Shc, ErbB2:PI3K, ErbB2:EGFR, ErbB2:ErbB3, ErbB2:ErbB4); ErbB3 (p-ErbB3, truncated ErbB3, ErbB3:PI3K, p-ErbB3:PI3K, ErbB3:Shc); ErbB4 (p-ErbB4, ErbB4:Shc); c-MET (p-c-MET, truncated c-MET, c-Met:HGF complex); AKT1 (p-AKT1); AKT2 (p-AKT2); AKT3 (p-AKT3); PTEN (p-PTEN); P70S6K (p-P70S6K); MEK (p-MEK); ERK1 (p-ERK1); ERK2 (p-ERK2); PDK1 (p-PDK1); PDK2 (p-PDK2); SGK3 (p-SGK3); 4E-BP1 (p-4E-BP1); PIK3R1 (p-PIK3R1); c-KIT (p-c-KIT); ER (p-ER); IGF-1R (p-IGF-1R, IGF-1R:IRS, IRS:PI3K, p-IRS, IGF-1R:PI3K); INSR (p-INSR); FLT3 (p-FLT3); HGFR1 (p-HGFR1); HGFR2 (p-HGFR2); RET (p-RET); PDGFRA (p-PDGFRA); PDGFRB (p-PDGFRB); VEGFR1 (p-VEGFR1, VEGFR1:PLCT, VEGFR1:Src); VEGFR2 (p-VEGFR2, VEGFR2:PLCT, VEGFR2:Src, VEGFR2:heparin sulphate, VEGFR2:VE-cadherin); VEGFR3 (p-VEGFR3); FGFR1 (p-FGFR1); FGFR2 (p-FGFR2); FGFR3 (p-FGFR3); FGFR4 (p-FGFR4); TIE1 (p-TIE1); TIE2 (p-TIE2); EPHA (p-EPHA); EPHB (p-EPHB); GSK-3β (p-GSK-3β); NF-kB (p-NF-kB, NF-kB-IkB alpha complex and others), IkB (p-IkB, p-P65:IkB); IKK (phospho IKK); BAD (p-BAD, BAD:14-3-3); mTOR (p-mTOR); Rsk-1 (p-Rsk-1); Jnk (p-Jnk); P38 (p-P38); STAT1 (p-STAT1); STAT3 (p-STAT3); FAK (p-FAK); RB (p-RB); Ki67; p53 (p-p53); CREB (p-CREB); c-Jun (p-c-Jun); c-Src (p-c-Src); paxillin (p-paxillin); GRB2 (p-GRB2), Shc (p-Shc), Ras (p-Ras), GAB1 (p-GAB1), SHP2 (p-SHP2), GRB2 (p-GRB2), CRKL (p-CRKL), PLC7 (p-PLCT), PKC (e.g., p-PKCα, p-PKCβ, p-PKCδ), adducin (p-adducin), RB1 (p-RB1), and PYK2 (p-PYK2).

The following tables provide additional examples of signal transduction molecules for which total levels and/or activation (e.g., phosphorylation) levels can be determined in a sample (e.g., alone or in combination with biomarkers from other categories) to aid or assist in predicting disease course, selecting an appropriate anti-TNF drug therapy, optimizing anti-TNF drug therapy, reducing toxicity associated with anti-TNF drug therapy, or monitoring the efficacy of therapeutic treatment with an anti-TNF drug.

| Total/Phospho Assays | | Phospho Sites |
|---|---|---|
| VEGFR2 Total | VEGFR2 Phospho | Y951, 1212 |
| Erk Total | Erk Phospho | T202/Y204 |
| Akt Total | Akt Phospho | T308, S473 |
| MEK Total | MEK Phospho | S217/221 |
| MEK Total | MEK Phospho | S217/221 |
| P70S6K Total | P70S6k Phospho | T389(T229) |
| PTEN Total | | |
| VEGFR1 (T) | VEGFR1 Phospho | |
| SGK total | SGK phosphor | T320, S486 |
| CRKL Total | CRKL Phospho | Y207 |
| SRC Total | SRK Phospho | Y 416, 527 |
| FAK Total | FAK Phospho | Y397 |
| BCR Total | BCR Phospho | |
| PI3K Activated | PI3K complexed | P85 Y688 |
| 4EBP1 | 4EBP1 phospho | T70, T37, T46 |
| PRAS40 | PRAS40 phospho | T246 |

| Total/Phospho Assays | | Phospho Sites |
|---|---|---|
| TIE Total | TIE - 2 Phospho | Y992 (S1119) |
| Jak 2 Total | JAK 2 Phospho | Y1007/1008 |
| STAT 5 Total | STAT 5 Phospho | Y694/699 |
| STAT 3 Total | STAT 3 Phospho | Y705 |
| FGFR1 total | FGFR1 Phospho | Y 653, 766 |
| FGFR2 total | FGFR 2 Phospho | Y653 |
| FGFR3 total | FGFR 3 Phospho | |
| FGFR4 total | FGFR 4 Phospho | |
| Axl total | Axl Phospho | Y702 |
| BAD total | BAD Phospho | (S112)(S136) |
| RSK total | RSK Phospho | (T359/S363) |
| PDK total | PDK 1 Phospho | (S241) |
| JAK 1 and 3 total | JAK 1 and 3 Phospho | |
| TSC2 total | TSC 2 Phospho | S664, S939 |
| S6RP Total | S6RP Phospho | S235/236 |

The Collaborative Enzyme Enhanced Reactive Immuno-Assay (CEER), also known as the Collaborative Proximity Immunoassay (COPIA), is described in the following patent documents which are herein incorporated by reference in their entirety for all purposes: PCT Publication No. WO 2008/036802; PCT Publication No. WO 2009/012140; PCT Publication No. WO 2009/108637; PCT Publication No. WO 2010/132723; PCT Publication No. WO 2011/008990; and PCT Application No. PCT/US2010/053386, filed Oct. 20, 2010.

G. Elimination Rate Constant

In certain embodiments, a marker for the disease activity profile (DAP) is kel, or the elimination rate constant of an antibody such as an anti-TNF antibody (e.g., infliximab). The determination of an elimination rate constant such as kel is particularly useful in the methods of the invention for personalized therapeutic management by selecting therapy, optimizing therapy, reducing toxicity, and/or monitoring the efficacy of therapeutic treatment with one or more therapeutic agents such as biologics (e.g., anti-TNF drugs).

In certain instances, a differential equation can be used to model drug elimination from the patient. In certain instances, a two-compartment PK model can be used. In this instance, the equation for the drug in the central compartment following intravenous bolus administration is:

$$\frac{dX1}{dt} = -kel \cdot X1 - k12 \cdot X1 + K21 \cdot X2.$$

The kel•X1 term describes elimination of the drug from the central compartment, while the k12 •X1 and k21 •X2 terms describe the distribution of drug between the central and peripheral compartments.

H. Genetic Markers

The determination of the presence or absence of allelic variants (e.g., SNPs) in one or more genetic markers in a sample (e.g., alone or in combination with biomarkers from other categories) is also useful in the methods of the present invention to aid or assist in predicting disease course, selecting an appropriate anti-TNF drug therapy, optimizing anti-TNF drug therapy, reducing toxicity associated with anti-TNF drug therapy, or monitoring the efficacy of therapeutic treatment with an anti-TNF drug.

Non-limiting examples of genetic markers include, but are not limited to, any of the inflammatory pathway genes and corresponding SNPs that can be genotyped as set forth in Table 1 (e.g., a NOD2/CARD15 gene, an IL12/IL23 pathway gene, etc.). Preferably, the presence or absence of at least one allelic variant, e.g., a single nucleotide polymorphism (SNP), in the NOD2/CARD15 gene and/or one or more genes in the IL12/IL23 pathway is determined. See, e.g., Barrett et al., *Nat. Genet.*, 40:955-62 (2008) and Wang et al., *Amer. J. Hum. Genet.*, 84:399-405 (2009).

TABLE 1

| Gene | SNP |
|---|---|
| NOD2 (R702W) - SNP8 | rs2066844 |
| NOD2 (G908R) - SNP12 | rs2066845 |
| NOD2 (3020insC) - SNP13 | rs5743293 |
| ATG16L1 (T300A) | rs2241880 |
| IL23R (R381Q) | rs11209026 |
| DLG5 | rs2165047 |
| NOD2/CARD15 | rs2066847 |
| IL23R | rs11465804 |
| ATG16L1 | rs3828309 |
| MST1 | rs3197999 |
| PTGER4 | rs4613763 |
| IRGM | rs11747270 |
| TNFSF15 | rs4263839 |
| ZNF365 | rs10995271 |
| NKX2-3 | rs11190140 |
| PTPN2 | rs2542151 |
| PTPN22 | rs2476601 |
| ITLN1 | rs2274910 |
| IL12B | rs10045431 |
| CDKAL1 | rs6908425 |
| CCR6 | rs2301436 |
| JAK2 | rs10758669 |
| C11orf30 | rs7927894 |
| LRRK2, MUC19 | rs11175593 |
| ORMDL3 | rs2872507 |
| STAT3 | rs744166 |
| ICOSLG | rs762421 |
| GCKR | rs780094 |
| BTNL2, SLC26A3, HLA-DRB1, HLA-DQA1 | rs3763313 |
| PUS10 | rs13003464 |
| CCL2, CCL7 | rs991804 |
| LYRM4 | rs12529198 |
| SLC22A23 | rs17309827 |
| IL18RAP | rs917997 |
| IL12RB2 | rs7546245 |
| IL12RB1 | rs374326 |
| CD3D | rs3212262 |
| CD3G | rs3212262 |
| CD247 | rs704853 |
| JUN | rs6661505 |
| CD3E | rs7937334 |
| IL18R1 | rs1035127 |
| CCR5 | |
| MAPK14 | rs2237093 |
| IL18 | rs11214108 |
| IFNG | rs10878698 |
| MAP2K6 | rs2905443 |
| STAT4 | rs1584945 |

TABLE 1-continued

| Gene | SNP |
|---|---|
| IL12A | rs6800657 |
| TYK2 | rs12720356 |
| ETV5 | rs9867846 |
| MAPK8 | rs17697885 |
| IRGM | rs13361189 |
| IRGM | rs4958847 |
| IRGM | rs1000113 |
| IRGM | rs11747270 |
| TL1A/TNFSF15 | rs6478109 |
| TL1A/TNFSF15 | rs6478108 |
| TL1A/TNFSF15 | rs4263839 |
| PTN22 | rs2476601 |
| CCR6 | rs1456893 |
| CCR6 | rs2301436 |
| 5p13/PTGER4 | rs1373692 |
| 5p13/PTGER4 | rs4495224 |
| 5p13/PTGER4 | rs7720838 |
| 5p13/PTGER4 | rs4613763 |
| ITLN1 | rs2274910 |
| ITLN1 | rs9286879 |
| ITLN1 | rs11584383 |
| IBD5/5q31 | rs2188962 |
| IBD5/5q31 | rs252057 |
| IBD5/5q31 | rs10067603 |
| GCKR | rs780094 |
| TNFRSF6B | rs1736135 |
| ZNF365 | rs224136 |
| ZNF365 | rs10995271 |
| C11orf30 | rs7927894 |
| LRRK2; MUC19 | rs1175593 |
| IL-27 | rs8049439 |
| TLR2 | rs4696480 |
| TLR2 | rs3804099 |
| TLR2 | rs3804100 |
| TLR2 | rs5743704 |
| TLR2 | rs2405432 |
| TLR4 (D299G) | rs4986790 |
| TLR4 (T399I) | rs4986791 |
| TLR4 (S360N) | rs4987233 |
| TLR9 | rs187084 |
| TLR9 | rs352140 |
| NFC4 | rs4821544 |
| KIF21B | rs11584383 |
| IKZF1 | rs1456893 |
| C11orf30 | rs7927894 |
| CCL2, CCL7 | rs991804 |
| ICOSLG | rs762421 |
| TNFAIP3 | rs7753394 |
| FLJ45139 | rs2836754 |
| PTGER4 | rs4613763 |
| ECM1 | rs7511649 |
| ECM1 (T130M) | rs3737240 |
| ECM1 (G290S) | rs13294 |
| GLI1 (G933D) | rs2228224 |
| GLI1 (Q1100E) | rs2228226 |
| MDR1 (3435C > T) | rs1045642 |
| MDR1 (A893S/T) | rs2032582 |
| MAGI2 | rs6962966 |
| MAGI2 | rs2160322 |
| IL26 | rs12815372 |
| IFNG, IL26 | rs1558744 |
| IFNG, IL26 | rs971545 |
| IL26 | rs2870946 |
| ARPC2 | rs12612347 |
| IL10, IL19 | rs3024493 |
| IL10, IL19 | rs3024505 |
| IL23R | rs1004819 |
| IL23R | rs2201841 |
| IL23R | rs11465804 |
| IL23R | rs10889677 |
| BTLN2 | rs9268480 |
| HLA-DRB1 | rs660895 |
| MEP1 | rs6920863 |
| MEP1 | rs2274658 |
| MEP1 | rs4714952 |
| MEP1 | rs1059276 |
| PUS10 | rs13003464 |
| PUS10 | rs6706689 |
| RNF186 | rs3806308 |
| RNF186 | rs1317209 |
| RNF186 | rs6426833 |
| FCGR2A, C | rs10800309 |
| CEP72 | rs4957048 |
| DLD, LAMB1 | rs4598195 |
| CAPN10, KIF1A | rs4676410 |
| IL23R | rs11805303 |
| IL23R | rs7517847 |
| IL12B/p40 | rs1368438 |
| IL12B/p40 | rs10045431 |
| IL12B/p40 | rs6556416 |
| IL12B/p40 | rs6887695 |
| IL12B/p40 | rs3212227 |
| STAT3 | rs744166 |
| JAK2 | rs10974914 |
| JAK2 | rs10758669 |
| NKX2-3 | rs6584283 |
| NKX2-3 | rs10883365 |
| NKX2-3 | rs11190140 |
| IL18RAP | rs917997 |
| LYRM4 | rs12529198 |
| CDKAL1 | rs6908425 |
| MAGI2 | rs2160322 |
| TNFRSF6B | rs2160322 |
| TNFRSF6B | rs2315008 |
| TNFRSF6B | rs4809330 |
| PSMG1 | rs2094871 |
| PSMG1 | rs2836878 |
| PTPN2 | rs2542151 |
| MST1/3p21 | rs9858542 |
| MST1/3p21 | rs3197999 |
| SLC22A23 | rs17309827 |
| MHC | rs660895 |
| XBP1 | rs35873774 |
| ICOSLG1 | rs762421 |
| BTLN2 | rs3763313 |
| BTLN2 | rs2395185 |
| BTLN2 | rs9268480 |
| ATG5 | rs7746082 |
| CUL2, CREM | rs17582416 |
| CARD9 | rs4077515 |
| ORMDL3 | rs2872507 |
| ORMDL3 | rs2305480 |

Additional SNPs useful in the present invention include, e.g., rs2188962, rs9286879, rs11584383, rs7746082, rs1456893, rs1551398, rs17582416, rs3764147, rs1736135, rs4807569, rs7758080, and rs8098673. See, e.g., Barrett et al., *Nat. Genet.,* 40:955-62 (2008).

In particular embodiments, the presence or absence of one or more mutations in one or more of the following genetic markers is determined: inflammatory pathway genes, e.g., the presence or absence of variant alleles (e.g., SNPs) in one or more inflammatory markers such as, e.g., NOD2/CARD15 (e.g., SNP 8, SNP 12, and/or SNP 13 described in U.S. Pat. No. 7,592,437), ATG16L1 (e.g., the rs2241880 (T300A) SNP described in Lakatos et al., *Digestive and Liver Disease,* 40 (2008) 867-873), IL23R (e.g., the rs11209026 (R381Q) SNP described in Lakatos et al.), the human leukocyte antigen (HLA) genes and/or cytokine genes described in, e.g., Gasche et al. (*Eur. J. Gastroenterology & Hepatology*, (2003) 15:599-606), and the DLG5 and/or OCTN genes from the IBD5 locus.

1. NOD2/CARD15

The determination of the presence or absence of allelic variants such as SNPs in the NOD2/CARD15 gene is particularly useful in the present invention. As used herein, the term "NOD2/CARD15 variant" or "NOD2 variant" includes a nucleotide sequence of a NOD2 gene containing one or more changes as compared to the wild-type NOD2 gene or an amino acid sequence of a NOD2 polypeptide containing one or more changes as compared to the wild-type NOD2 polypeptide sequence. NOD2, also known as CARD15, has been localized to the IBD1 locus on chromosome 16 and identified by positional-cloning (Hugot et al., *Nature,* 411:599-603 (2001)) as well as a positional candidate gene strategy (Ogura et al., *Nature,* 411:603-606 (2001); Hampe et al., *Lancet,* 357:1925-1928 (2001)). The IBD1 locus has a high multipoint linkage score (MLS) for inflammatory bowel disease (MLS=5.7 at marker D16S411 in 16q12). See, e.g., Cho et al., *Inflamm. Bowel Dis.,* 3:186-190 (1997); Akolkar et al., *Am. J. Gastroenterol.,* 96:1127-1132 (2001); Ohmen et al., *Hum. Mol. Genet.,* 5:1679-1683 (1996); Parkes et al., *Lancet,* 348:1588 (1996); Cavanaugh et al., *Ann. Hum. Genet.,* 62:291-8 (1998); Brant et al., *Gastroenterology,* 115:1056-1061 (1998); Curran et al., *Gastroenterology,* 115:1066-1071 (1998); Hampe et al., *Am. J. Hum. Genet.,* 64:808-816 (1999); and Annese et al., *Eur. J. Hum. Genet.,* 7:567-573 (1999).

The mRNA (coding) and polypeptide sequences of human NOD2 are set forth in, e.g., Genbank Accession Nos. NM_022162 and NP_071445, respectively. In addition, the complete sequence of human chromosome 16 clone RP11-327F22, which includes NOD2, is set forth in, e.g., Genbank Accession No. AC007728. Furthermore, the sequence of NOD2 from other species can be found in the GenBank database.

The NOD2 protein contains amino-terminal caspase recruitment domains (CARDs), which can activate NF-kappa B (NF-kB), and several carboxy-terminal leucine-rich repeat domains (Ogura et al., *J. Biol. Chem.,* 276:4812-4818 (2001)). NOD2 has structural homology with the apoptosis regulator Apaf-1/CED-4 and a class of plant disease resistant gene products (Ogura et al., supra). Similar to plant disease resistant gene products, NOD2 has an amino-terminal effector domain, a nucleotide-binding domain and leucine rich repeats (LRRs). Wild-type NOD2 activates nuclear factor NF-kappa B, making it responsive to bacterial lipopolysaccharides (LPS; Ogura et al., supra; Inohara et al., *J. Biol. Chem.,* 276:2551-2554 (2001). NOD2 can function as an intercellular receptor for LPS, with the leucine rich repeats required for responsiveness.

Variations at three single nucleotide polymorphisms in the coding region of NOD2 have been previously described. These three SNPs, designated R702W ("SNP 8"), G908R ("SNP 12"), and 1007fs ("SNP 13"), are located in the carboxy-terminal region of the NOD2 gene (Hugot et al., supra). A further description of SNP 8, SNP 12, and SNP 13, as well as additional SNPs in the NOD2 gene suitable for use in the invention, can be found in, e.g., U.S. Pat. Nos. 6,835,815; 6,858,391; and 7,592,437; and U.S. Patent Publication Nos. 20030190639, 20050054021, and 20070072180.

In some embodiments, a NOD2 variant is located in a coding region of the NOD2 locus, for example, within a region encoding several leucine-rich repeats in the carboxy-terminal portion of the NOD2 polypeptide. Such NOD2 variants located in the leucine-rich repeat region of NOD2 include, without limitation, R702W ("SNP 8") and G908R ("SNP 12"). A NOD2 variant useful in the invention can also encode a NOD2 polypeptide with reduced ability to activate NF-kappa B as compared to NF-kappa B activation by a wild-type NOD2 polypeptide. As a non-limiting example, the NOD2 variant 1007fs ("SNP 13") results in a truncated NOD2 polypeptide which has reduced ability to induce NF-kappa B in response to LPS stimulation (Ogura et al., *Nature,* 411:603-606 (2001)).

A NOD2 variant useful in the invention can be, for example, R702W, G908R, or 1007fs. R702W, G908R, and 1007fs are located within the coding region of NOD2. In one embodiment, a method of the invention is practiced with the R702W NOD2 variant. As used herein, the term "R702W" includes a single nucleotide polymorphism within exon 4 of the NOD2 gene, which occurs within a triplet encoding amino acid 702 of the NOD2 protein. The wild-type NOD2 allele contains a cytosine (c) residue at position 138,991 of the AC007728 sequence, which occurs within a triplet encoding an arginine at amino acid 702. The R702W NOD2 variant contains a thymine (t) residue at position 138,991 of the AC007728 sequence, resulting in an arginine (R) to tryptophan (W) substitution at amino acid 702 of the NOD2 protein. Accordingly, this NOD2 variant is denoted "R702W" or "702W" and can also be denoted "R675W" based on the earlier numbering system of Hugot et al., supra. In addition, the R702W variant is also known as the "SNP 8" allele or a "2" allele at SNP 8. The NCBI SNP ID number for R702W or SNP 8 is rs2066844. The presence of the R702W NOD2 variant and other NOD2 variants can be conveniently detected, for example, by allelic discrimination assays or sequence analysis.

A method of the invention can also be practiced with the G908R NOD2 variant. As used herein, the term "G908R" includes a single nucleotide polymorphism within exon 8 of the NOD2 gene, which occurs within a triplet encoding amino acid 908 of the NOD2 protein. Amino acid 908 is located within the leucine rich repeat region of the NOD2 gene. The wild-type NOD2 allele contains a guanine (g) residue at position 128,377 of the AC007728 sequence, which occurs within a triplet encoding glycine at amino acid 908. The G908R NOD2 variant contains a cytosine (c) residue at position 128,377 of the AC007728 sequence, resulting in a glycine (G) to arginine (R) substitution at amino acid 908 of the NOD2 protein. Accordingly, this NOD2 variant is denoted "G908R" or "908R" and can also be denoted "G881R" based on the earlier numbering system of Hugot et al., supra. In addition, the G908R variant is also known as the "SNP 12" allele or a "2" allele at SNP 12. The NCBI SNP ID number for G908R SNP 12 is rs2066845.

A method of the invention can also be practiced with the 1007fs NOD2 variant. This variant is an insertion of a single nucleotide that results in a frame shift in the tenth leucine-rich repeat of the NOD2 protein and is followed by a premature stop codon. The resulting truncation of the NOD2 protein appears to prevent activation of NF-kappaB in response to bacterial lipopolysaccharides (Ogura et al., supra). As used herein, the term "1007fs" includes a single nucleotide polymorphism within exon 11 of the NOD2 gene, which occurs in a triplet encoding amino acid 1007 of the NOD2 protein. The 1007fs variant contains a cytosine which has been added at position 121,139 of the AC007728 sequence, resulting in a frame shift mutation at amino acid 1007. Accordingly, this NOD2 variant is denoted "1007fs" and can also be denoted "3020insC" or "980fs" based on the earlier numbering system of Hugot et al., supra. In addition, the 1007fs NOD2 variant is also known as the "SNP 13" allele or a "2" allele at SNP 13. The NCBI SNP ID number for 1007fs or SNP 13 is rs2066847.

One skilled in the art recognizes that a particular NOD2 variant allele or other polymorphic allele can be conveniently defined, for example, in comparison to a Centre d'Etude du Polymorphisme Humain (CEPH) reference individual such as the individual designated 1347-02 (Dib et al., *Nature,* 380:152-154 (1996)), using commercially available reference DNA obtained, for example, from PE Biosystems (Foster City, CA). In addition, specific information on SNPs can be obtained from the dbSNP of the National Center for Biotechnology Information (NCBI).

A NOD2 variant can also be located in a non-coding region of the NOD2 locus. Non-coding regions include, for example, intron sequences as well as 5' and 3' untranslated sequences. A non-limiting example of a NOD2 variant allele located in a non-coding region of the NOD2 gene is the JW1 variant, which is described in Sugimura et al., *Am. J. Hum. Genet.,* 72:509-518 (2003) and U.S. Patent Publication No. 20070072180. Examples of NOD2 variant alleles located in the 3' untranslated region of the NOD2 gene include, without limitation, the JW15 and JW16 variant alleles, which are described in U.S. Patent Publication No. 20070072180. Examples of NOD2 variant alleles located in the 5' untranslated region (e.g., promoter region) of the NOD2 gene include, without limitation, the JW17 and JW18 variant alleles, which are described in U.S. Patent Publication No. 20070072180.

As used herein, the term "JW1 variant allele" includes a genetic variation at nucleotide 158 of intervening sequence 8 (intron 8) of the NOD2 gene. In relation to the AC007728 sequence, the JW1 variant allele is located at position 128,143. The genetic variation at nucleotide 158 of intron 8 can be, but is not limited to, a single nucleotide substitution, multiple nucleotide substitutions, or a deletion or insertion of one or more nucleotides. The wild-type sequence of intron 8 has a cytosine at position 158. As non-limiting examples, a JW1 variant allele can have a cytosine (c) to adenine (a), cytosine (c) to guanine (g), or cytosine (c) to thymine (t) substitution at nucleotide 158 of intron 8. In one embodiment, the JW1 variant allele is a change from a cytosine (c) to a thymine (t) at nucleotide 158 of NOD2 intron 8.

The term "JW15 variant allele" includes a genetic variation in the 3' untranslated region of NOD2 at nucleotide position 118,790 of the AC007728 sequence. The genetic variation at nucleotide 118,790 can be, but is not limited to, a single nucleotide substitution, multiple nucleotide substitutions, or a deletion or insertion of one or more nucleotides. The wild-type sequence has an adenine (a) at position 118,790. As non-limiting examples, a JW15 variant allele can have an adenine (a) to cytosine (c), adenine (a) to guanine (g), or adenine (a) to thymine (t) substitution at nucleotide 118,790. In one embodiment, the JW15 variant allele is a change from an adenine (a) to a cytosine (c) at nucleotide 118,790.

As used herein, the term "JW16 variant allele" includes a genetic variation in the 3' untranslated region of NOD2 at nucleotide position 118,031 of the AC007728 sequence. The genetic variation at nucleotide 118,031 can be, but is not limited to, a single nucleotide substitution, multiple nucleotide substitutions, or a deletion or insertion of one or more nucleotides. The wild-type sequence has a guanine (g) at position 118,031. As non-limiting examples, a JW16 variant allele can have a guanine (g) to cytosine (c), guanine (g) to adenine (a), or guanine (g) to thymine (t) substitution at nucleotide 118,031. In one embodiment, the JW16 variant allele is a change from a guanine (g) to an adenine (a) at nucleotide 118,031.

The term "JW17 variant allele" includes a genetic variation in the 5' untranslated region of NOD2 at nucleotide position 154,688 of the AC007728 sequence. The genetic variation at nucleotide 154,688 can be, but is not limited to, a single nucleotide substitution, multiple nucleotide substitutions, or a deletion or insertion of one or more nucleotides. The wild-type sequence has a cytosine (c) at position 154,688. As non-limiting examples, a JW17 variant allele can have a cytosine (c) to guanine (g), cytosine (c) to adenine (a), or cytosine (c) to thymine (t) substitution at nucleotide 154,688. In one embodiment, the JW17 variant allele is a change from a cytosine (c) to a thymine (t) at nucleotide 154,688.

As used herein, the term "JW18 variant allele" includes a genetic variation in the 5' untranslated region of NOD2 at nucleotide position 154,471 of the AC007728 sequence. The genetic variation at nucleotide 154,471 can be, but is not limited to, a single nucleotide substitution, multiple nucleotide substitutions, or a deletion or insertion of one or more nucleotides. The wild-type sequence has a cytosine (c) at position 154,471. As non-limiting examples, a JW18 variant allele can have a cytosine (c) to guanine (g), cytosine (c) to adenine (a), or cytosine (c) to thymine (t) substitution at nucleotide 154,471. In one embodiment, the JW18 variant allele is a change from a cytosine (c) to a thymine (t) at nucleotide 154,471.

It is understood that the methods of the invention can be practiced with these or other NOD2 variant alleles located in a coding region or non-coding region (e.g., intron or promoter region) of the NOD2 locus. It is further understood that the methods of the invention can involve determining the presence of one, two, three, four, or more NOD2 variants, including, but not limited to, the SNP 8, SNP 12, and SNP 13 alleles, and other coding as well as non-coding region variants.

II. Statistical Analysis

In some aspects, the present invention provides methods for selecting anti-TNF drug therapy, optimizing anti-TNF drug therapy, reducing toxicity associated with anti-TNF drug therapy, and/or monitoring the efficacy of anti-TNF drug treatment by applying a statistical algorithm to one or more (e.g., a combination of two, three, four, five, six, seven, or more) biochemical markers, serological markers, and/or genetic markers to generate a disease activity profile (DAP). In particular embodiments, quantile analysis is applied to the presence, level, and/or genotype of one or more markers to guide treatment decisions for patients receiving anti-TNF drug therapy. In other embodiments, one or a combination of two of more learning statistical classifier systems are applied to the presence, level, and/or genotype of one or more markers to guide treatment decisions for patients receiving anti-TNF drug therapy. The statistical analyses of the methods of the present invention advantageously provide improved sensitivity, specificity, negative predictive value, positive predictive value, and/or overall accuracy for selecting an initial anti-TNF drug therapy and for determining when or how to adjust or modify (e.g., increase or decrease) the subsequent dose of an anti-TNF drug, to combine an anti-TNF drug (e.g., at an increased, decreased, or same dose) with one or more immunosuppressive agents such as methotrexate (MTX) or azathioprine (AZA), and/or to change the current course of therapy (e.g., switch to a different anti-TNF drug).

The term "statistical analysis" or "statistical algorithm" or "statistical process" includes any of a variety of statistical methods and models used to determine relationships between variables. In the present invention, the variables are the presence, level, or genotype of at least one marker of interest. Any number of markers can be analyzed using a statistical analysis described herein. For example, the presence or level of 1, 2, 3, 4, 5, 6, 7, 8, 9, 10, 11, 12, 13, 14, 15, 16, 17, 18, 19, 20, 25, 30, 35, 40, 45, 50, 55, 60, or more markers can be included in a statistical analysis. In one embodiment, logistic regression is used. In another embodiment, linear regression is used. In yet another embodiment, ordinary least squares regression or unconditional logistic regression is used. In certain preferred embodiments, the statistical analyses of the present invention comprise a quantile measurement of one or more markers, e.g., within a given population, as a variable. Quantiles are a set of "cut points" that divide a sample of data into groups containing (as far as possible) equal numbers of observations. For example, quartiles are values that divide a sample of data into four groups containing (as far as possible) equal numbers of observations. The lower quartile is the data value a quarter way up through the ordered data set; the upper quartile is the data value a quarter way down through the ordered data set. Quintiles are values that divide a sample of data into five groups containing (as far as possible) equal numbers of observations. The present invention can also include the use of percentile ranges of marker levels (e.g., tertiles, quartile, quintiles, etc.), or their cumulative indices (e.g., quartile sums of marker levels to obtain quartile sum scores (QSS), etc.) as variables in the statistical analyses (just as with continuous variables).

In certain embodiments, the present invention involves detecting or determining the presence, level (e.g., magnitude), and/or genotype of one or more markers of interest using quartile analysis. In this type of statistical analysis, the level of a marker of interest is defined as being in the first quartile (<25%), second quartile (25-50%), third quartile (51%-<75%), or fourth quartile (75-100%) in relation to a reference database of samples. These quartiles may be assigned a quartile score of 1, 2, 3, and 4, respectively. In certain instances, a marker that is not detected in a sample is assigned a quartile score of 0 or 1, while a marker that is detected (e.g., present) in a sample (e.g., sample is positive for the marker) is assigned a quartile score of 4. In some embodiments, quartile 1 represents samples with the lowest marker levels, while quartile 4 represent samples with the highest marker levels. In other embodiments, quartile 1 represents samples with a particular marker genotype (e.g., wild-type allele), while quartile 4 represent samples with another particular marker genotype (e.g., allelic variant). The reference database of samples can include a large spectrum of patients with a TNFα-mediated disease or disorder such as, e.g., IBD. From such a database, quartile cut-offs can be established. A non-limiting example of quartile analysis suitable for use in the present invention is described in, e.g., Mow et al., *Gastroenterology,* 126:414-24 (2004).

In some embodiments, the statistical analyses of the present invention comprise one or more learning statistical classifier systems. As used herein, the term "learning statistical classifier system" includes a machine learning algorithmic technique capable of adapting to complex data sets (e.g., panel of markers of interest) and making decisions based upon such data sets. In some embodiments, a single learning statistical classifier system such as a decision/classification tree (e.g., random forest (RF) or classification and regression tree (C&RT)) is used. In other embodiments, a combination of 2, 3, 4, 5, 6, 7, 8, 9, 10, or more learning statistical classifier systems are used, preferably in tandem. Examples of learning statistical classifier systems include, but are not limited to, those using inductive learning (e.g., decision/classification trees such as random forests, classification and regression trees (C&RT), boosted trees, etc.), Probably Approximately Correct (PAC) learning, connectionist learning (e.g., neural networks (NN), artificial neural networks (ANN), neuro fuzzy networks (NFN), network structures, the Cox Proportional-Hazards Model (CPHM), perceptrons such as multi-layer perceptrons, multi-layer feed-forward networks, applications of neural networks, Bayesian learning in belief networks, etc.), reinforcement learning (e.g., passive learning in a known environment such as naïve learning, adaptive dynamic learning, and temporal difference learning, passive learning in an unknown environment, active learning in an unknown environment, learning action-value functions, applications of reinforcement learning, etc.), and genetic algorithms and evolutionary programming. Other learning statistical classifier systems include support vector machines (e.g., Kernel methods), multivariate adaptive regression splines (MARS), Levenberg-Marquardt algorithms, Gauss-Newton algorithms, mixtures of Gaussians, gradient descent algorithms, and learning vector quantization (LVQ).

Random forests are learning statistical classifier systems that are constructed using an algorithm developed by Leo Breiman and Adele Cutler. Random forests use a large number of individual decision trees and decide the class by choosing the mode (i.e., most frequently occurring) of the classes as determined by the individual trees. Random forest analysis can be performed, e.g., using the RandomForests software available from Salford Systems (San Diego, CA). See, e.g., Breiman, *Machine Learning,* 45:5-32 (2001); and http://stat-www.berkeley.edu/users/breiman/RandomForests/cc_home.htm, for a description of random forests.

Classification and regression trees represent a computer intensive alternative to fitting classical regression models and are typically used to determine the best possible model for a categorical or continuous response of interest based upon one or more predictors. Classification and regression tree analysis can be performed, e.g., using the C&RT software available from Salford Systems or the Statistica data analysis software available from StatSoft, Inc. (Tulsa, OK). A description of classification and regression trees is found, e.g., in Breiman et al. "Classification and Regression Trees," Chapman and Hall, New York (1984); and Steinberg et al., "CART: Tree-Structured Non-Parametric Data Analysis," Salford Systems, San Diego, (1995).

Neural networks are interconnected groups of artificial neurons that use a mathematical or computational model for information processing based on a connectionist approach to computation. Typically, neural networks are adaptive systems that change their structure based on external or internal information that flows through the network. Specific examples of neural networks include feed-forward neural networks such as perceptrons, single-layer perceptrons, multi-layer perceptrons, backpropagation networks, ADALINE networks, MADALINE networks, Learnmatrix networks, radial basis function (RBF) networks, and self-organizing maps or Kohonen self-organizing networks; recurrent neural networks such as simple recurrent networks and Hopfield networks; stochastic neural networks such as Boltzmann machines; modular neural networks such as committee of machines and associative neural networks; and other types of networks such as instantaneously trained neural networks, spiking neural networks, dynamic neural networks, and cascading neural networks. Neural network analysis can be performed, e.g., using the Statistica data analysis software available from StatSoft, Inc. See, e.g., Freeman et al., In "Neural Networks: Algorithms, Applications and Programming Techniques," Addison-Wesley Publishing Company (1991); Zadeh, Information and Control, 8:338-353 (1965); Zadeh, "IEEE Trans. on Systems, Man and Cybernetics," 3:28-44 (1973); Gersho et al., In "Vector Quantization and Signal Compression," Kluywer Academic Publishers, Boston, Dordrecht, London (1992); and Hassoun, "Fundamentals of Artificial Neural Networks," MIT Press, Cambridge, MA, London (1995), for a description of neural networks.

Support vector machines are a set of related supervised learning techniques used for classification and regression and are described, e.g., in Cristianini et al., "An Introduction to Support Vector Machines and Other Kernel-Based Learning Methods," Cambridge University Press (2000). Support vector machine analysis can be performed, e.g., using the SVM$^{light}$ software developed by Thorsten Joachims (Cornell University) or using the LIBSVM software developed by Chih-Chung Chang and Chih-Jen Lin (National Taiwan University).

The various statistical methods and models described herein can be trained and tested using a cohort of samples (e.g., serological and/or genomic samples) from healthy individuals and patients with a TNFα-mediated disease or disorder such as, e.g., IBD (e.g., CD and/or UC). For example, samples from patients diagnosed by a physician, preferably by a gastroenterologist, as having IBD or a clinical subtype thereof using a biopsy, colonoscopy, or an immunoassay as described in, e.g., U.S. Pat. No. 6,218,129, are suitable for use in training and testing the statistical methods and models of the present invention. Samples from patients diagnosed with IBD can also be stratified into Crohn's disease or ulcerative colitis using an immunoassay as described in, e.g., U.S. Pat. Nos. 5,750,355 and 5,830,675. Samples from healthy individuals can include those that were not identified as IBD samples. One skilled in the art will know of additional techniques and diagnostic criteria for obtaining a cohort of patient samples that can be used in training and testing the statistical methods and models of the present invention.

As used herein, the term "sensitivity" includes the probability that a method of the present invention for selecting anti-TNF drug therapy, optimizing anti-TNF drug therapy, reducing toxicity associated with anti-TNF drug therapy, and/or monitoring the efficacy of anti-TNF drug treatment gives a positive result when the sample is positive, e.g., having the predicted therapeutic response to anti-TNF drug therapy or toxicity associated with anti-TNF drug therapy. Sensitivity is calculated as the number of true positive results divided by the sum of the true positives and false negatives. Sensitivity essentially is a measure of how well the present invention correctly identifies those who have the predicted therapeutic response to anti-TNF drug therapy or toxicity associated with anti-TNF drug therapy from those who do not have the predicted therapeutic response or toxicity. The statistical methods and models can be selected such that the sensitivity is at least about 60%, and can be, e.g., at least about 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%.

The term "specificity" includes the probability that a method of the present invention for selecting anti-TNF drug therapy, optimizing anti-TNF drug therapy, reducing toxicity associated with anti-TNF drug therapy, and/or monitoring the efficacy of anti-TNF drug treatment gives a negative result when the sample is not positive, e.g., not having the predicted therapeutic response to anti-TNF drug therapy or toxicity associated with anti-TNF drug therapy. Specificity is calculated as the number of true negative results divided by the sum of the true negatives and false positives. Specificity essentially is a measure of how well the present invention excludes those who do not have the predicted therapeutic response to anti-TNF drug therapy or toxicity associated with anti-TNF drug therapy from those who do have the predicted therapeutic response or toxicity. The statistical methods and models can be selected such that the specificity is at least about 60%, and can be, e.g., at least about 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%.

The term "negative predictive value" or "NPV" includes the probability that an individual identified as not having the predicted therapeutic response to anti-TNF drug therapy or toxicity associated with anti-TNF drug therapy actually does not have the predicted therapeutic response or toxicity. Negative predictive value can be calculated as the number of true negatives divided by the sum of the true negatives and false negatives. Negative predictive value is determined by the characteristics of the methods of the present invention as well as the prevalence of the disease in the population analyzed. The statistical methods and models can be selected such that the negative predictive value in a population having a disease prevalence is in the range of about 70% to about 99% and can be, for example, at least about 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%.

The term "positive predictive value" or "PPV" includes the probability that an individual identified as having the predicted therapeutic response to anti-TNF drug therapy or toxicity associated with anti-TNF drug therapy actually has the predicted therapeutic response or toxicity. Positive predictive value can be calculated as the number of true positives divided by the sum of the true positives and false positives. Positive predictive value is determined by the characteristics of the methods of the present invention as well as the prevalence of the disease in the population analyzed. The statistical methods and models can be selected such that the positive predictive value in a population having a disease prevalence is in the range of about 70% to about 99% and can be, for example, at least about 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%.

Predictive values, including negative and positive predictive values, are influenced by the prevalence of the disease in the population analyzed. In the present invention, the statistical methods and models can be selected to produce a desired clinical parameter for a clinical population with a particular prevalence for a TNFα-mediated disease or disorder such as, e.g., IBD. As a non-limiting example, statistical methods and models can be selected for an IBD prevalence of up to about 1%, 2%, 3%, 4%, 5%, 6%, 7%, 8%, 9%, 10%, 15%, 20%, 25%, 30%, 35%, 40%, 45%, 50%, 55%, 60%, 65%, or 70%, which can be seen, e.g., in a clinician's office such as a gastroenterologist's office or a general practitioner's office.

As used herein, the term "overall agreement" or "overall accuracy" includes the accuracy with which a method of the present invention selects anti-TNF drug therapy, optimizes anti-TNF drug therapy, reduces toxicity associated with anti-TNF drug therapy, and/or monitors the efficacy of anti-TNF drug treatment. Overall accuracy is calculated as the sum of the true positives and true negatives divided by the total number of sample results and is affected by the prevalence of the disease in the population analyzed. For example, the statistical methods and models can be selected such that the overall accuracy in a patient population having a disease prevalence is at least about 40%, and can be, e.g., at least about 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%.

III. Examples

The present invention will be described in greater detail by way of specific examples. The following examples are offered for illustrative purposes, and are not intended to limit the invention in any manner. Those of skill in the art will readily recognize a variety of noncritical parameters which can be changed or modified to yield essentially the same results.

The Examples set forth in U.S. Provisional Application No. 61/444,097, filed Feb. 17, 2011, and PCT Application No. PCT/US2010/054125, filed Oct. 26, 2010, are hereby incorporated by reference in their entirety for all purposes.

Example 1. Disease Activity Profiling for Identifying Responders and Non-Responders to Anti-TNFα Biologics This example describes methods for personalized therapeutic management of a TNFα-mediated disease in order to optimize therapy or monitor therapeutic efficacy in a subject using the disease activity profiling of the present invention to identify subjects as responders or non-responders to anti-TNF drug therapy.

FIG. 1 illustrates an exemplary IBD wound response profile in which wound progression is divided into inflammatory, proliferative, and remodeling phases. As non-limiting examples, inflammatory response phase markers tested include: anti-TNF drugs such as Remicade (infliximab); anti-drug antibodies (ADA) such as HACA; inflammatory markers such as GM-CSF, IFN-γ, IL-1β, IL-2, IL-6, IL-8, TNF-α, and sTNF RII; and anti-inflammatory markers such as IL-12p70 and IL-10. Non-limiting examples of proliferation response phase markers tested include tissue repair/remodeling factors (also referred to as mucosal healing markers) such as AREG, EREG, HB-EGF, HGF, NRG1, NRG2, NRG3, NRG4, BTC, EGF, IGF, TGF-α, VEGF-A, VEGF-B, VEGF-C, VEGF-D, FGF1, FGF2, FGF7, FGF9, and TWEAK.

A COMMIT (Combination Of Maintenance Methotrexate-Infliximab Trial) study was performed to evaluate the safety and efficacy of Remicade (infliximab) in combination with methotrexate for the long-term treatment of Crohn's disease (CD). Treatment success was defined by the proportion of subjects in clinical remission (i.e., complete discontinuation of prednisone therapy and a Crohn's Disease Activity Index (CDAI) score of <150) at week 14, and maintenance of clinical remission between study weeks 14 and 50. In particular, clinical assessment with CDAI was performed at week 0, 46, 50, and 66. Subjects with CDAI>150 were identified as non-responders. Additional information on the COMMIT study is provided at http://www.clinicaltrials.gov/ct2/show/NCT00132899, the disclosure of which is incorporated by reference in its entirety for all purposes.

Disease activity profiling was performed on a number of subjects in the COMMIT study. In particular, the following array of markers were measured at various time points during treatment with Remicade (infliximab) only or a combination of Remicade (infliximab) with methotrexate: (1) Remicade (infliximab) and HACA; (2) inflammatory markers GM-CSF, IFN-γ, IL-1β, IL-2, IL-6, IL-8, TNF-α, and sTNF RII; (3) anti-inflammatory markers IL-12p70 and IL-10; and (4) tissue repair markers EGF, bFGF, PlGF, sFlt1, and VEGF. The disease activity profile (DAP) for 7 of these subjects, which provides a comparison between responder and non-responder profiles, is illustrated herein. These patient examples show that markers for inflammation and tissue repair correlated with infliximab and HACA levels in select active CD patients, certain markers may predict the disease activity profile, and disease activity profiling will further guide patient therapy and identify mucosal healing markers. In addition, these patient examples show that whenever anti-inflammatory cytokines such as IL-12p70 and IL-10 are elevated, the patient responds, indicating that they may be markers of mucosal healing, and that tissue repair markers (TRM) go up in non-responders.

Table of Personalized Disease Activity Profiling: Levels of IFX, HACA, Inflammatory Markers, Anti-Inflammatory Markers, and Mucosal Healing Markers

| Patient ID No. | Treatment Regimen | CDAI | Clinical Definition | IFX | HACA | Inflammatory Markers | Anti-inflammatory Markers | Mucosal Healing Markers |
|---|---|---|---|---|---|---|---|---|
| 12209 | IFX + MTX | t = 0, CDAI was 202. t = wk 26, CDAI was 183 t = wk 66, CDAI = 152. | Non-responder | Low at trough (wk 14) | HACA+. LOW | HIGH | LOW | MEDIUM |
| 11010 | IFX | t = 0, CDAI was 262. t = wk 46, CDAI was 85. | Responder | High at trough (wk 14) | HACA−. ND | LOW | HIGH | HIGH |
| 10118 | IFX | t = 0, CDAI was 251. t = wk 46, CDAI was 109. | Responder | High at trough (wk 14) | HACA−. ND | MEDIUM | HIGH | HIGH |
| 11602 | IFX + MTX | t = 0, CDAI was 217. t = wk 46, CDAI was 68. | Responder | High at trough (wk 14) | HACA−. ND | LOW | HIGH | HIGH |

-continued

Table of Personalized Disease Activity Profiling: Levels of IFX, HACA, Inflammatory Markers, Anti-Inflammatory Markers, and Mucosal Healing Markers

| Patient ID No. | Treatment Regimen | CDAI | Clinical Definition | IFX | HACA | Inflammatory Markers | Anti-inflammatory Markers | Mucosal Healing Markers |
|---|---|---|---|---|---|---|---|---|
| 11505 | IFX | t = 0, CDAI was 272.<br>t = wk 46, CDAI was 145.<br>t = wk 66, CDAI = 195. | Non-responder | Very Low at trough (wk 14) | HACA++. HIGH | MEDIUM | LOW | HIGH |
| 11601 | IFX + MTX | t = 0, CDAI was 207.<br>t = wk 46, CDAI was 0. | Responder | High at trough (wk 14) | HACA+. LOW | HIGH | HIGH | MEDIUM |

IFX = infliximab.
MTX = methotrexate.
ND = no detectable level of HACA.

Patient 12209: Infliximab+Methotrexate (MTX) Treated.

CDAI at time 0 was 202. At week 46, CDAI was 183 ("Delta 19" or 202−19=183). At week 66, CDAI was 152 ("Delta 50" or 202−50=152). Clinically defined as non-responder. Disease activity profile (DAP) accurately identified this patient. In particular, DAP showed that this patient had low infliximab (IFX) levels at trough ("T"; Week 14), the presence of a detectable concentration level of HACA ("HACA+"), high inflammatory marker levels, low anti-inflammatory marker levels, and medium tissue repair marker (TRM) levels. Suggested alternative treatment options may include, for example, increasing the dose of IFX, switching to therapy with adalimumab (HUMIRA™), treating with a different immunosuppressive drug such as azathioprine (AZA), and/or switching to therapy with a drug that targets a different mechanism (e.g., an anti-INFγ antibody such as fontolizumab).

Patient 11010: Infliximab Treated.

CDAI at week 0 was 262. At week 46, CDAI was 85 ("Delta 177" or 262−177=85). Clinical responder. Disease activity profile (DAP) accurately identified this patient. In particular, DAP showed that this patient had high infliximab (IFX) levels at trough ("T"; Week 14), no detectable level of HACA ("HACA +"), low inflammatory marker levels, high anti-inflammatory marker levels, and high tissue repair marker (TRM) levels. For example, anti-inflammatory cytokines IL-12p70 and IL-10 were high. As shown with the patients in this example, whenever anti-inflammatory cytokines were high, the patient responded most probably with mucosal healing. In addition, bFGF concentration levels were low at all time points, although other TRM levels were high, indicating that tissue growth was muted, such that tissue repair had already occurred.

Patient 10118: Infliximab Treated.

CDAI at week 0 was 251. At week 46, CDAI was 109 ("Delta 142" or 251-142=109). Clinical responder. Disease activity profile (DAP) accurately identified this patient. In particular, DAP showed that this patient had high infliximab (IFX) levels at trough ("T"; Week 14), no detectable level of HACA ("HACA −"), medium inflammatory marker levels, high anti-inflammatory marker levels, and high tissue repair marker (TRM) levels. For example, anti-inflammatory cytokines IL-12p70 and IL-10 were high. Again, as shown with the patients in this example, whenever anti-inflammatory cytokines were high, the patient responded most probably with mucosal healing. In addition, bFGF concentration levels were low at all time points and remained flat over the course of therapy, although other TRM levels were higher, indicating that tissue growth was muted, such that tissue repair had already occurred.

Patient 11602: Infliximab+Methotrexate (MTX) Treated.

CDAI at week 0 was 217. At week 46, CDAI was 68 ("Delta 149" or 217−149=68). Clinical responder. Disease activity profile (DAP) accurately identified this patient. In particular, DAP showed that this patient had high infliximab (IFX) levels at trough ("T"; Week 14), no detectable level of HACA ("HACA −"), low inflammatory marker levels, high anti-inflammatory marker levels, and high tissue repair marker (TRM) levels. For example, anti-inflammatory cytokines IL-12p70 and IL-10 were high. Again, as shown with the patients in this example, whenever anti-inflammatory cytokines were high, the patient responded most probably with mucosal healing. In addition, bFGF concentration levels were lower at all time points compared to the other TRM levels, indicating that tissue growth was muted, such that tissue repair had already occurred.

Patient 11505: Infliximab Treated.

CDAI at time 0 was 272. At week 46, CDAI was 145 ("Delta 127" or 272-127=145). At week 66, CDAI was 195. Clinically defined as non-responder. Disease activity profile (DAP) accurately identified this patient. In particular, DAP showed that this patient had very low infliximab (IFX) levels at trough ("T"; Week 14), a high concentration level of HACA ("HACA++"), medium inflammatory marker levels, low anti-inflammatory marker levels, and high tissue repair marker (TRM) levels. In non-responders, the levels of TRM such as bFGF go up, while in responders they either go down or do not change. Suggested alternative treatment options may include, for example, increasing the dose of IFX, switching to therapy with adalimumab (HUMIRA™), treating with an immunosuppressive drug such as MTX or azathioprine (AZA), and/or switching to therapy with a drug that targets a different mechanism (e.g., an anti-INFγ antibody such as fontolizumab).

Patient 11601: Infliximab+Methotrexate (MTX) Treated.

CDAI at week 0 was 207. At week 46, CDAI was 0 ("Delta 207" or 207−207=0). The patient was clinically defined as responder. Disease activity profile (DAP) accurately identified this patient. In particular, DAP showed that this patient had high infliximab (IFX) levels at trough ("T"; Week 14), low HACA levels ("HACA+"), high inflammatory marker levels, high anti-inflammatory marker levels, and medium tissue repair marker (TRM) levels. For example, anti-inflammatory cytokines IL-12p70 and IL-10 were high. Again, as shown with the patients in this example, whenever anti-inflammatory cytokines were high, the patient responded most probably with mucosal healing, clearly indicating that anti-inflammatory markers are very important. The presence of high inflammation may be due to complication.

Patient 10113: Infliximab Treated.

CDAI at time 0 was 150. At week 46, CDAI was 96 ("Delta 54" or 150−54=96). At visit 10 ("V10"), CDAI was 154, and at visit 11 ("V11"), CDAI was 169. As such, CDAI started at 150 and stayed around 150. The patient was clinically defined as non-responder. Disease activity profile (DAP) accurately identified this patient. In particular, DAP showed that this patient had low infliximab (IFX) levels at trough ("T"; Week 14), a detectable concentration level of HACA ("HACA+"), medium inflammatory marker levels, low anti-inflammatory marker levels, and medium tissue repair marker (TRM) levels. Again, TRM levels go up in non-responders, while in responders they either go down or do not change. Suggested alternative treatment options may include, for example, increasing the dose of IFX, switching to therapy with adalimumab (HUMIRA™), treating with an immunosuppressive drug such as MTX or azathioprine, and/or switching to therapy with a drug that targets a different mechanism (e.g., an anti-INFγ antibody such as fontolizumab).

Example 2. Disease Activity Profiling Modeling

An exemplary 3-dimensional graph rendering of the disease activity profile (DAP) of the present invention includes each of the different markers present in the array of markers on the x-axis, normalized marker levels on the y-axis, and time on the z-axis (e.g., time points wherein samples are taken and marker levels measured). An exemplary topographic map of the DAP of the present invention (also referred to herein as a personalized disease profile) includes each of the different markers present in the array of markers the y-axis, time on the x-axis (e.g., time points wherein samples are taken and marker levels measured), and relative marker levels in grayscale.

The 3D models described herein represent a novel paradigm for treatment because they are individualized and titratable such that dose adjustments are made in a personalized manner. For example, marker panels including markers such as inflammatory, proliferative, and remodeling markers enable a determination in real-time of the best course of treatment for a patient on therapy such as anti-TNF drug therapy, e.g., for treating CD or RA. As a result, both the time course and the concentration levels of markers in the panel or array of markers are important for therapy adjustment and monitoring to personalize and individualize therapy and determine optimal doses or dose adjustments. In certain instances, the change in one or more marker levels over time is an important consideration for therapy adjustment and monitoring. In particular embodiments, the desired therapeutic zone for the set or a subset of the markers in the array or panel is within a defined range in the 3D graph or topographic map.

Example 3. Infliximab Non-Detection

This example represents a model for "time-to-event." In other words, this example uses the Cox Proportional-Hazards Model (CPHM) to model the time it takes for "an event" to occur and the risk of such an event happening. The model is a regression analysis with "time-to-event" on the Y axis, which is a response variable, and "predictor variables" on the X axis. In this example, the non-detection of infliximab (i.e., the concentration of infliximab falling below a detection threshold) is the event, with the potential predictors of such an event being biomarkers: e.g., CRP, IL-2, VEGF, and the like and or clinical information such as age, MTX treatment, gender, and the like.

Figure 11:
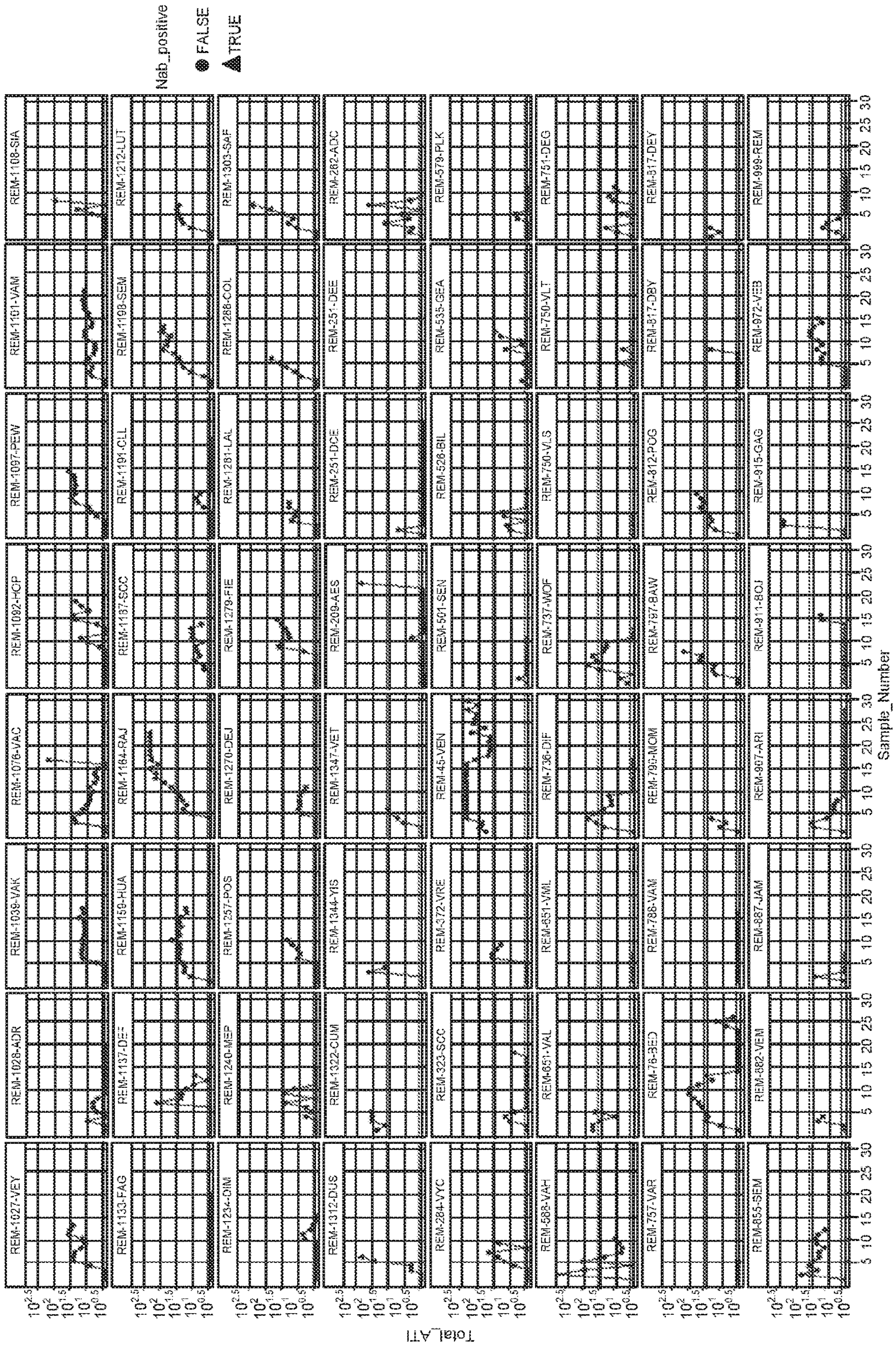
FIG. 11 illustrates that levels of ATI and neutralizing antibodies can be determined over time in a series of samples from various patients.

In this example, the "Hazard" is the risk of infliximab not being detected (e.g., non-detection) by an analytical assay such as a mobility shift assay. For example, FIG. 11 shows infliximab concentration levels for various patients during their course of treatment. An event occurs in this example when the concentration of infliximab falls below a predetermined detection threshold. In certain instances, the CPHM is being used to predict the risk of the event occurring (infliximab non-detection). The example also identifies biomarkers indicative of such a risk occurring.

Using the CPHM, time is modeled until infliximab is not detectable by a mobility shift assay. In the model, the predetermined threshold is 0.67 μg/mL, which is the lower bound of the reference range. If the infliximab concentration level is less than the threshold at time "t," then the event has occurred at time "t." In FIG. 12, patients were ranked by their time to the event. The event occurred for various patients at different points during treatment and is denoted with a bullet point.

In the initial model, there were various markers and clinical information used to predict the hazard or the risk of infliximab non-detection by the mobility shift assay. These markers included the following markers in the Table:

| |
|---|
| EGF |
| bFGF |
| PIGF |
| sFlt1 |
| VEGF |
| GM-CSF |
| IFN-γ |
| IL-10 |
| IL-12p70 |
| IL-1β |
| IL-2 |
| IL-6 |
| IL-8 |
| TNF-α |
| sTNFRII |
| CRP |
| SAA |
| ICAM-1 |
| VCAM-1 |
| AGE |
| Months since diagnosis |
| Disease @ colon |
| Disease @ small intestine |
| MTX treatment |
| Success |

From the initial marker list, the following list was derived as being the preferred markers indicative of the event:

| |
|---|
| GM-CSF |
| IL-2 |
| IL-6 |
| TNF-α |
| sRNFRII |
| SAA |
| ICAM-1 |
| Months since Dx |
| Disease @ small intestine |
| Success |

The following Table lists the significant predictors of infliximab non-detection risk or the hazard:

| Predictor | coef | exp(coef) | se(coef) | p |
|---|---|---|---|---|
| GM-CSF | −1.92E−01 | 0.826 | 9.48E−02 | 4.34E−02 |
| IL-2 | 1.42E−01 | 1.153 | 1.92E−02 | 1.63E−13 |
| TNF-α | 2.33E−02 | 1.024 | 7.57E−03 | 2.11E−03 |
| sTNFRII | 3.57E−01 | 1.429 | 5.76E−02 | 5.67E−10 |
| SAA | 6.13E−06 | 1.000 | 1.90E−06 | 1.25E−03 |
| Months since Dx | −3.20E−03 | 0.997 | 1.45E−03 | 2.68E−02 |
| Disease @ small intestine | 1.10E+00 | 2.995 | 4.46E−01 | 1.39E−02 |
| Success | 8.84E−01 | 2.421 | 3.13E−01 | 4.72E−03 |

The results in the above Table indicate the following are predictors of the hazard i.e., risk of the non-detection of infliximab:

GM-CSF: holding all other variables constant, an extra ng/μl of GM-CSF reduces the weekly hazard of infliximab non-detection by a factor of 0.826, or 17.4%.

IL-2: An additional 1 ng/μl of IL-2 increases the hazard by a factor of 1.153, or 15.3%.

TNF-α: A 1 ng/μl of TNF-α increases the hazard by a factor of 1.024/2.4%.

sTNFRII: A 1 ng/μl of sTNFRII increases the hazard by a factor of 1.429/42.9%.

SAA: A 1 ng/μl of SAA increases the hazard by a factor of 1.000006/0.0006%, which is very small, but still a detectable effect (small SE).

Months since diagnosis: Each additional month since diagnosis decreases the hazard by a factor of 0.997, or 0.3%.

Disease site at the small intestine (categorical variable): If the disease is located at the small intestine, the hazard is increased by a factor of 2.995, or nearly 200%.

Success (categorical variable): Also a predictive of hazard; in non-successful patients the hazard is increased by a factor of 2.421 or 142%.

In summary, the following markers appear to be good predictors of infliximab "clearance"/or non-detection: 1) GM-CSF; 2) IL-2; 3) TNF-α; 4) sTNFRII; and 5) the disease being situated in the small intestine.

As such, in one embodiment, the present invention provides:

A method for predicting the likelihood the concentration of an anti-TNF therapeutic or antibody during the course of treatment will fall below a threshold value, the method comprising:

measuring a panel of markers selected from the group consisting of 1) GM-CSF; 2) IL-2; 3) TNF-α; 4) sTNFRII; and 5) the disease being situated in the small intestine; and predicting the likelihood the concentration of an anti-TNF therapeutic or antibody will fall below the threshold based upon the concentration of the markers.

Example 4. Detection of Antidrug Antibody to Infliximab ("ATI" or "HACA")

This example uses the Cox Proportional-Hazards Model (CPHM) to model the time that it takes for an event to occur. This is a similar analysis to Example 3 above, but with the appearance of the anti-drug antibody also known as ATI or HACA as the event and risk of ATI formation (detection) as the hazard. FIG. 13 shows the concentration of ATI (HACA) in various patients during the course of treatment. In FIG. 14, patients were ranked by their time to the event. The event occurred for various patients at different points during treatment and is denoted with a bullet point. The risk of ATI detection is the hazard. Significant predictors of the hazard include:

| Predictor | coef | exp(coef) | se(coef) | p |
|---|---|---|---|---|
| EGF | −2.33E−03 | 0.998 | 1.18E−03 | 7.82E−03 |
| VEGF | 1.37E−03 | 1.001 | 4.10E−04 | 8.64E−04 |
| GM-CSF | −2.72E−01 | 0.762 | 1.06E−01 | 1.06E−02 |
| IL-2 | 6.15E−01 | 1.850 | 2.81E−01 | 2.83E−02 |
| IL-8 | 3.58E−04 | 1.000 | 1.22E−04 | 3.25E−03 |
| TNF-α | 2.37E−02 | 1.024 | 8.76E−03 | 6.81E−03 |
| CRP | 3.09E−05 | 1.000 | 1.04E−05 | 3.00E−03 |
| VCAM | 1.28E−03 | 1.001 | 2.01E−04 | 1.87E−10 |

The data in the above table indicates that EGF, VEGF, IL-8, CRP and VCAM-1 all have very small, but significant effects on the hazard.

GM-CSF: Holding all other variables constant, an extra ng/μl of GM-CSF reduces the weekly hazard of ATI detection by a factor of 0.762, or 27.4%.

IL-2: A 1 ng/μl increase of TL-2 increases the hazard by a factor of 1.85, or 85%.

TNF-α: A 1 ng/μl increase of TNF-α increases hazard by a factor of 1.024, or 2.4%.

In summary, the Predictors of ATI detection hazard are GM-CSF, IL-2 and TNF-α.

As such, in one embodiment, the present invention provides a method for predicting the likelihood that anti-drug antibodies will occur in an individual on anti-TNF therapy or antibodies, said method comprising:

measuring a panel of markers selected from the group consisting of EGF, VEGF, IL-8, CRP and VCAM-1; and predicting the likelihood that anti-drug antibodies will occur in an individual on anti-TNF therapy based on the concentration of marker levels.

Example 5. Disease Activity Profiling for Crohn's Disease Prognosis Using COMMIT Study Samples This example illustrates methods for personalized therapeutic management of a TNFα-mediated disease in order to optimize therapy or monitor therapeutic efficacy in a subject using the disease activity profiling of the present invention. This examples illustrates disease activity profiling which comprises detecting, measuring, or determining the presence, level and or activation of one or more specific biomarkers (e.g., drug levels, anti-drug antibody levels, inflammatory markers, anti-inflammatory markers, and tissue repair markers).

This example describes disease activity profiling on a number of samples from the COMMIT study. As described in Example 1, the COMMIT (Combination of Maintenance Methotrexate-Inflixamab Trial) study was performed to evaluate the safety and efficacy of Remicade (inflixamab) in combination with methotrexate (MTX) for the long-term treatment of Crohn's Disease (CD). In particular, the following array of markers was measured at various time points during treatment with Remicade (infliximab; IFX) only or a treatment of Remicade with MTX: (1) Remicade (inflixamab) and antidrug antibodies to infliximab (ATI); (2) inflammatory markers CRP, SAA, ICAM, VCAM; and (3) tissue repair marker VEGF. This example shows that the markers of inflammation and tissue repair correlated with IFX and ATI levels in select patients of TNF-α mediated disease (e.g., Crohn's Disease and Ulcerative Colitis). In some instances, arrays of markers may predict a disease activity index (e.g., Crohn's Disease Activity Index). Analysis of the COMMIT study is illustrated herein.

Figure 4C:
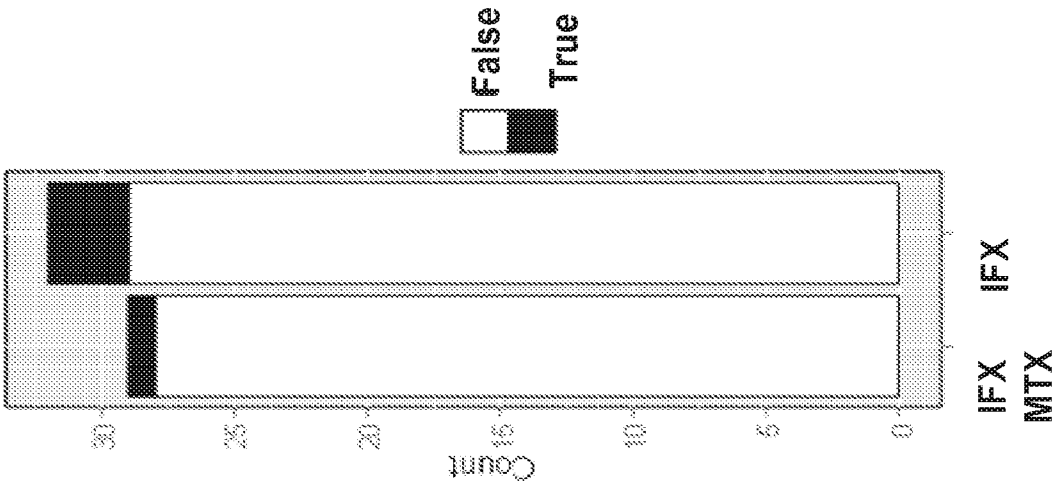
FIG. 4C shows that concurrent immunosuppressant therapy (e.g., MTX) is more likely to suppress the presence of ATI.
Figure 4B:
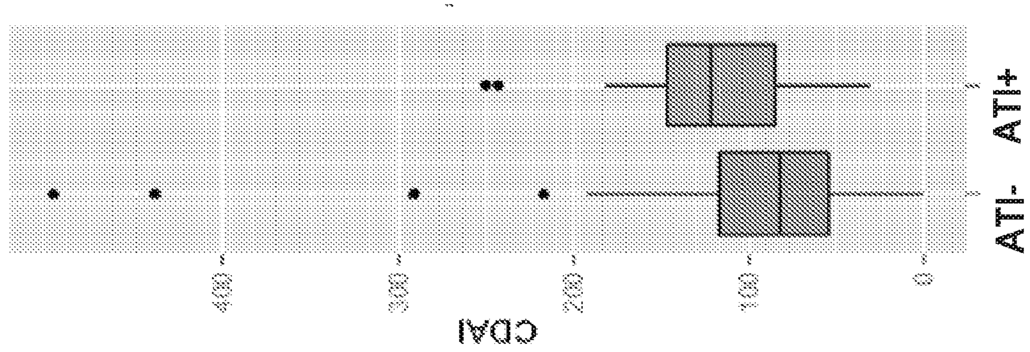
FIG. 4B illustrates that the presence of ATI correlates with higher CDAI.
Figure 4A:
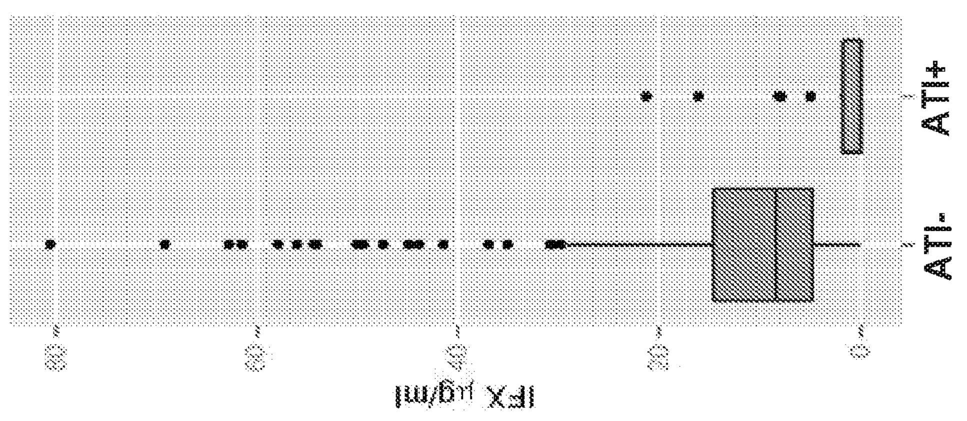
FIG. 4A illustrates an association between the presence of ATI and the level of IFX in patient samples. Samples with no detectable level of ATI had a significantly higher IFX median concentration, compared to sample with detectable ATI.

The relationship between the presence of ATI and serum levels of IFX concentration was investigated. For the evaluation, total ATI levels below the level of quantitation (BLOQ) were 3.13 U/ml, and were set to 0. IFX concentrations below the level of detection (BLOD) were set to 0. Per the sample comparison, only trough samples were used and a total of 219 were used in the evaluation. 24 samples were determined to be ATI positive (ATI+). It was determined that the median level of IFX was 0 μg/ml in ATI+ samples, while the median level of IFX was 8.373 μg/ml in ATI negative (ATI−) samples ($p=3.71\times10^{-9}$ by Mann Whitney U test). FIG. 4A illustrates an association between the presence of ATI and the level of IFX in patient samples. Patient samples with no detectable level of ATI had a significantly higher IFX median concentration, compared to ATI+ samples.

The relationship between CDAI and the presence of ATI was evaluated. In the analysis ATI of 3.13 U/ml was set as the cut-off, only trough samples were evaluated and ATI BLOQ was set as 0. 195 samples were ATI−, while 24 samples from a total of 4 patients were ATI+. The results showed that the median CDAI for ATI+ samples was 121.5 while the median CDAI for ATI− samples was 82 (p=0.0132 by Mann Whitney U test). FIG. 4B illustrates that the presence of ATI correlates with higher CDAI. The results show that ATI+ samples have significantly higher CDAI than ATI− samples.

The relationship between the presence of ATI and combination therapy of IFX and immunosuppressant agent (e.g., MTX) was investigated. ATI+ samples at any trough time point were analyzed. The results showed that there was no significant difference in odds of having ATI between IFX therapy alone and IFX+MTX combination therapy. The high odds ratio (e.g., 2.851) indicates that MTX can prevent a patient from developing an immune response to therapeutic biologics. FIG. 4C shows that concurrent immunosuppressant therapy (e.g., MTX) is more likely to suppress the presence of ATI.

Figure 5B:
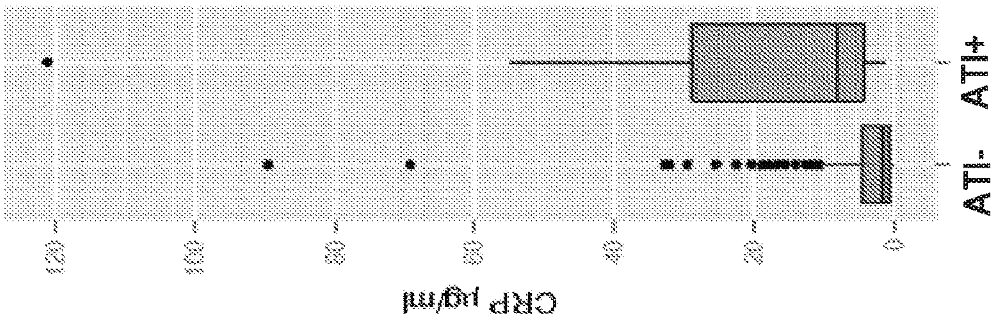
FIG. 5B illustrates that the inflammatory marker CRP is associated with increased levels of ATI.
Figure 5A:
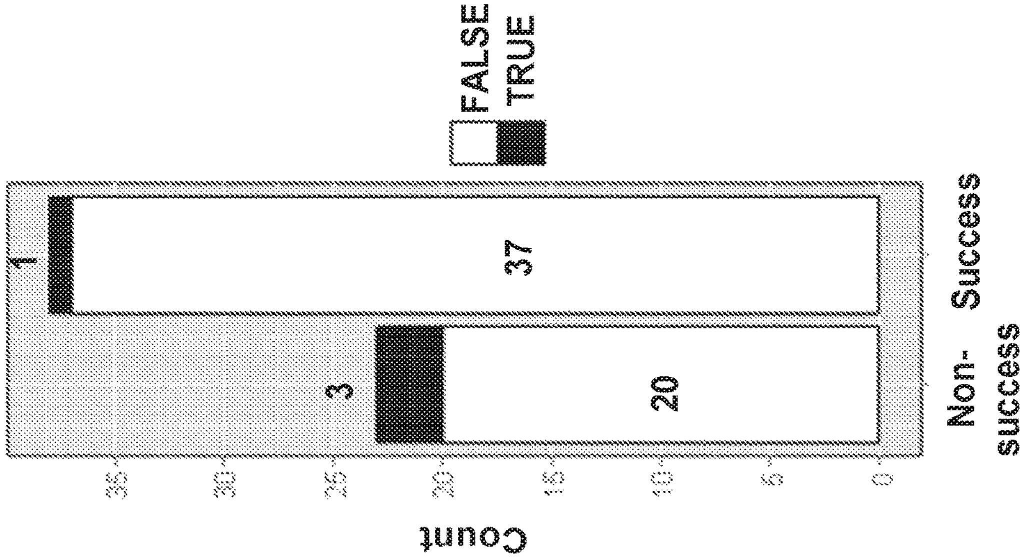
FIG. 5A shows that patients with ATI are more likely to develop a poor response to treatment.

The relationship between ATI and clinical outcome at follow-up was also investigated. ATI+ samples at any trough time point were analyzed. Clinical outcome as described from the clinical data received from the study was parsed as either "success" or "non-success". No significant difference in odds of being ATI+ was seen regardless of treatment regimen. The low odds ratio (e.g., 0.1855, p=0.1459) indicates that ATI+ patients tend to have poor clinical outcomes. FIG. 5A shows that patients with ATI are more likely to develop a poor response to treatment.

Figure 6:
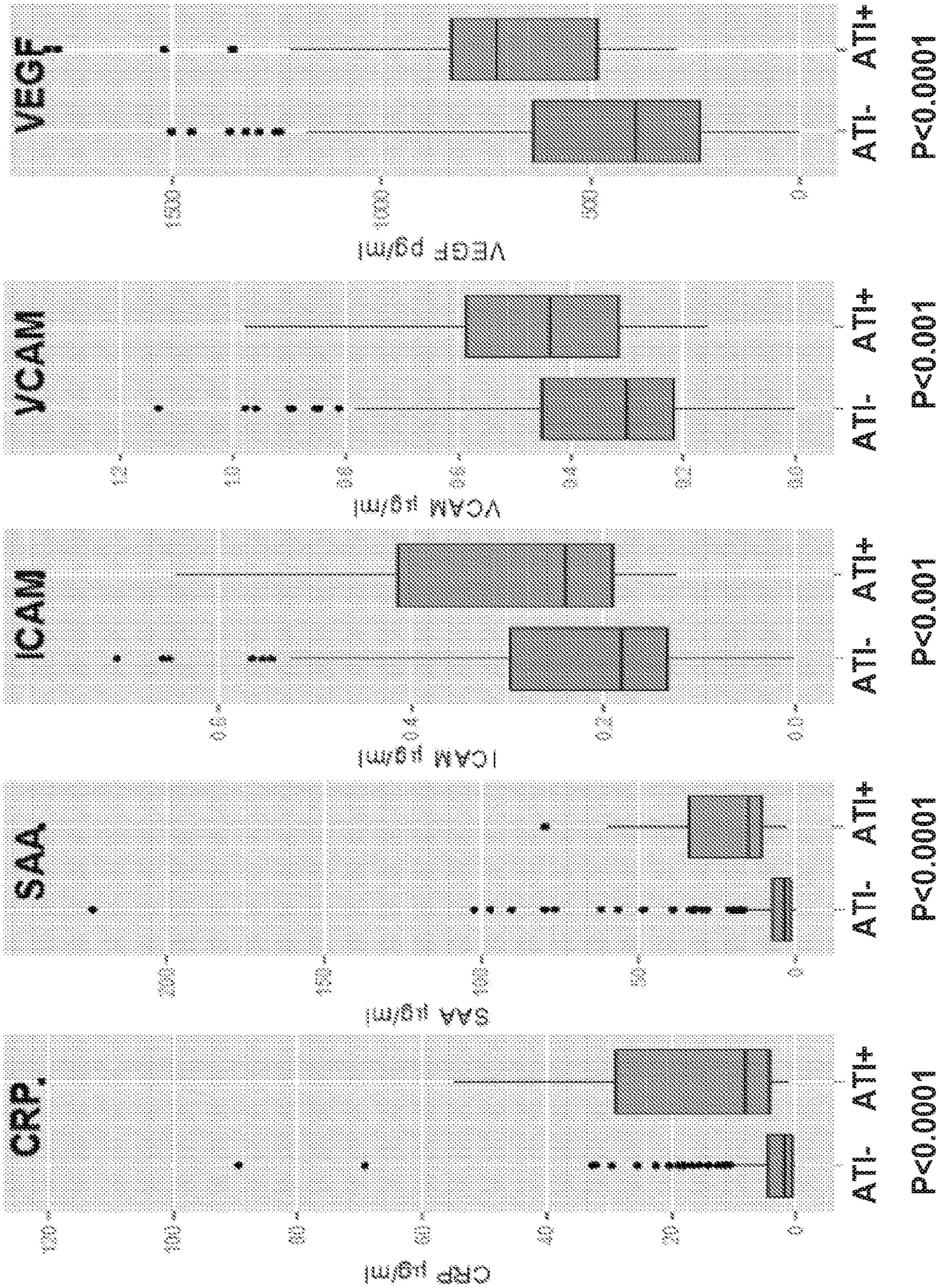
FIG. 6 illustrates that the protein levels of an array of one or more inflammatory and tissue repair markers correlate to the formation of antibodies to IFX.
Figure 7A:
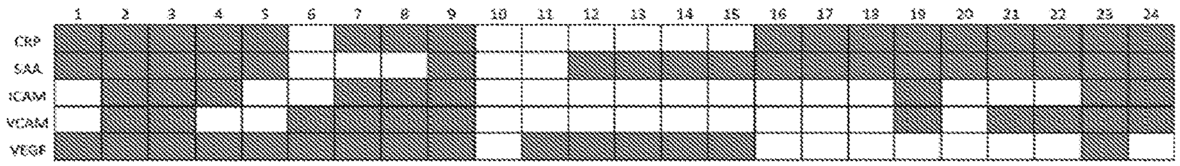
FIG. 7A illustrates that an array of inflammatory markers can be used to establish an inflammatory index what correlates with the presence of ATI and/or disease progression.

This example also illustrates an association of an exemplary PRO Inflammatory Index and serum levels of infliximab (IFX) or the presence of antibodies to IFX (ATI) in a patient sample. FIG. 5B illustrates that the inflammatory marker CRP is associated with increased levels of ATI. The data shows that the median CRP level was 8.11 μg/ml in ATI+ samples and 1.73 μg/ml in ATI− samples ($p=2.67\times10^{-6}$ by Mann Whitney U Test). Other inflammatory and tissue repair markers were evaluated. FIG. 6 illustrates that the protein levels of an array of one or more inflammatory and tissue repair markers correlate to the formation of antibodies to IFX. The data shows that of a combination of five markers (e.g., CRP, SAA, ICAM, VCAM, VEGF and including at least one inflammatory marker) was expressed in 23 out of 24 ATI positive samples (FIG. 7A, grey box). The inflammatory marker SAA was found to be positive in 19 of the 24 ATI positive samples that were also clinically described as having "high inflammation". The results also show that VEGF and CRP are the most non-overlapping markers in the analysis.

Figure 7B:
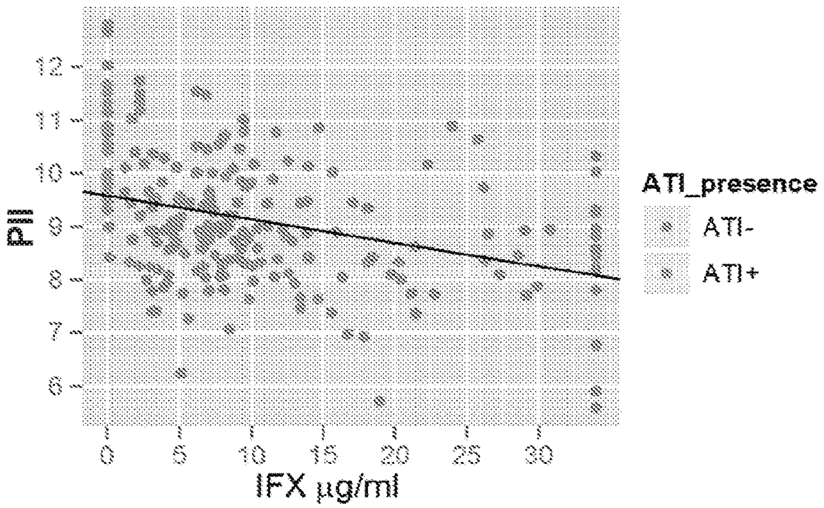
FIG. 7B shows the relationship between the PII and IFX concentrations in samples with ATI present.
Figure 7C:
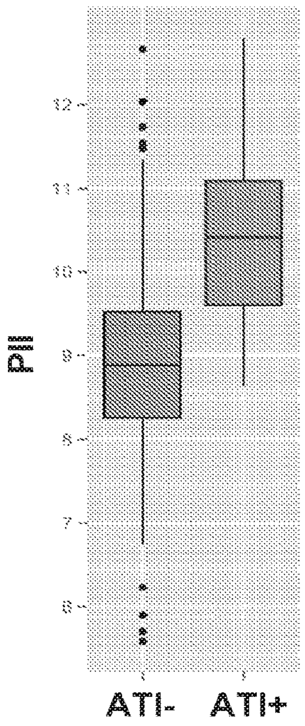
FIG. 7C illustrates that an exemplary PRO Inflammatory Index correlates with levels of IFX ($p<0.0001$ and $R^2=-0.129$) in patient samples of the COMMIT study.

This example further shows an exemplary PRO Inflammatory Index (P11). The inflammatory index score is created by logarithmic transformation of a combination of values representing determined expression levels of a plurality of markers (e.g., PII=log(CRP+SAA+ICAM+VCAM+VEGF)). FIG. 7B illustrates that an exemplary PRO Inflammatory Index (PII) correlates with levels of IFX ($p<0.0001$ and $R^2=-0.129$) in patient samples of the COMMIT study. The results show that ATI positive samples have a significantly higher inflammatory index score compared to ATI negative samples ($P=6.4\times10^{-8}$; see FIG. 7C).

As such, in one embodiment, the present invention provides a method for monitoring an infliximab treatment regimen, said method comprising:

a) measuring infliximab and antidrug antibodies to infliximab (ATI);

b) measuring inflammatory markers CRP, SAA, ICAM, VCAM;

c) measuring tissue repair marker VEGF; and d) correlating the measurements to therapeutic efficacy.

Example 6. Disease Activity Profiling for TNF-α Mediated Disease Prognosis Using Clinical Study #1 Samples This example describes methods for monitoring therapeutic efficacy in a subject using the disease activity profiling of the present invention to identify subjects as responders or non-responders to anti-TNF drug therapy. This example illustrates the use of disease activity profiling with a number of patient samples from a Crohn's Disease clinical trial #1.

In particular, an array of markers was measured at various time points during treatment with Remicade (infliximab; IFX) only or a treatment of Remicade with MTX: Remicade (inflixamab), antibodies to infliximab (ATI), and neutralizing antibodies to IFX. This example shows that a disease activity profile can show the relationship among ATI, IFX and neutralizing antibodies. Analysis of clinical study #1 is illustrated herein.

Figure 8A:
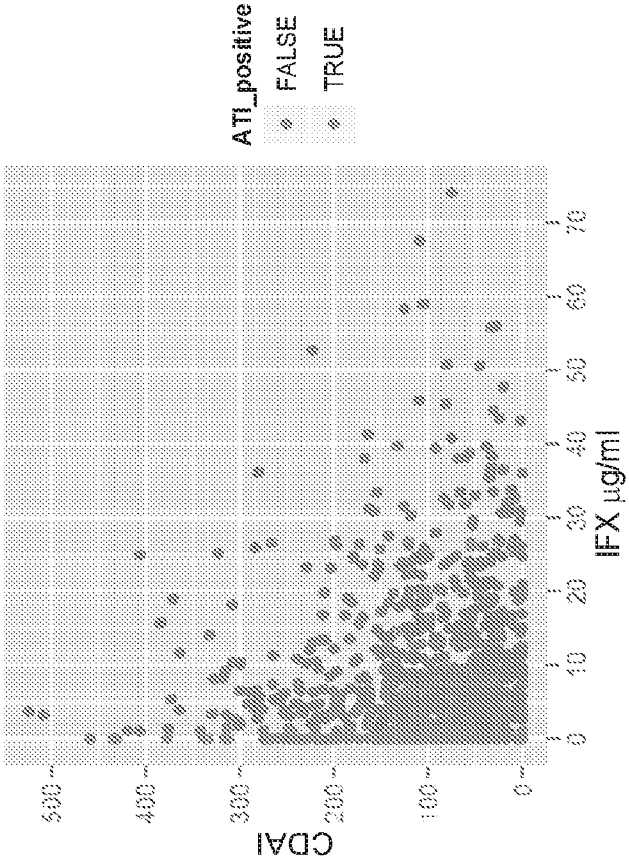
FIG. 8A illustrates the correlation between Crohn's Disease Activity Index (CDAI) score and the concentration of infliximab in serum in a number of patients in clinical study #1.
Figure 8B:
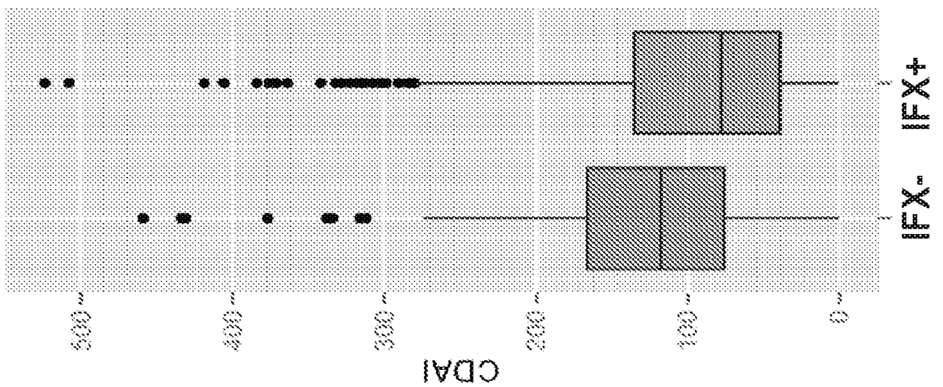
FIG. 8B shows that the presence of IFX in a sample correlated with a higher CDAI.

FIG. 8A-B illustrates the correlation between Crohn's Disease Activity Index (CDAI) score and the concentration of infliximab in serum in a number of patients in clinical study #1. In brief, 894 samples were analyzed. An IFX concentration ≥0.1 μg/ml at the limit of detection (LOD) was defined to be "present". The results showed that IFX negative (IFX−) samples also have significantly higher CDAI (p=0.0254, calculated by Mann-Whitney U test), compared to IFX positive samples (IFX+).

Figure 9A:
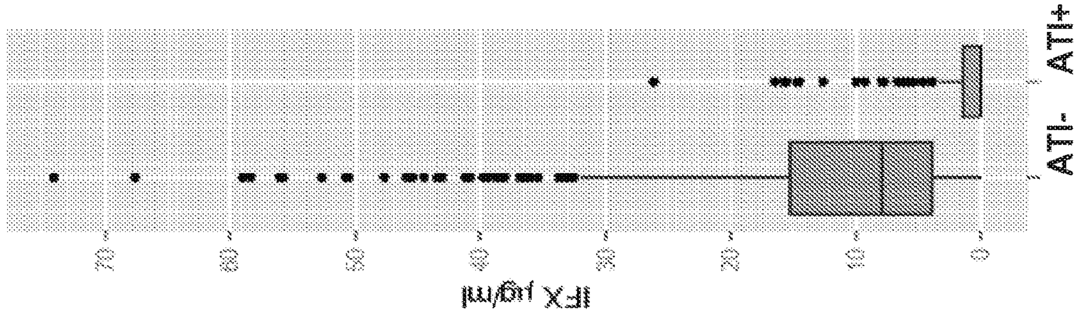
FIG. 9A illustrates the association between IFX concentration and the presence of antidrug antibodies to infliximab in samples analyzed.

Further analysis revealed that the presence of ATI correlates with lower IFX concentrations. It was assumed that total ATI below the level of quantitation (BLOQ) of 3.13 U/ml was set as 0 and IFX concentration below the level of detection (BLOD) was set at 0. It was determined that 24% of the patients (62/258) in the study were ATI+, as defined as positive total ATI levels at one of three time points. The analysis of 894 samples showed a correlation between IFX concentration and ATI levels. In particular, the median IFX was 0 μg/ml for ATI+ samples and 7.95 μg/ml for ATI− samples ($p<2.2\times10^{-16}$ by Mann-Whitney U test). FIG. 9A illustrates the association between IFX concentration and the presence of antidrug antibodies to inflixamab in samples analyzed.

Figure 9B:
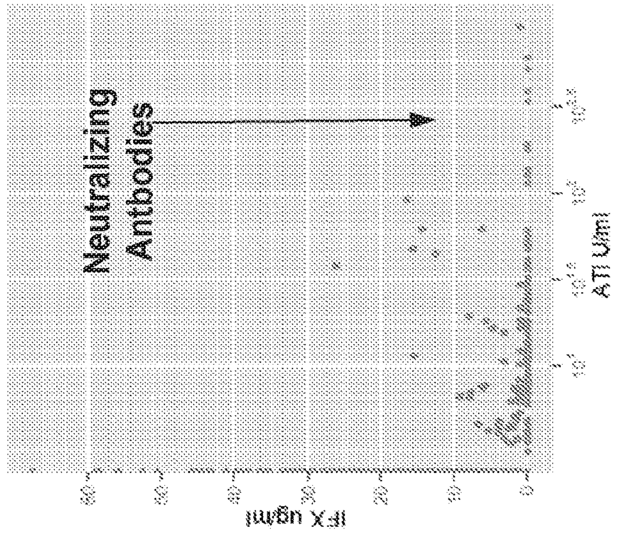
FIG. 9B illustrates that a high concentration of ATI can lead to neutralizing antibodies and undetectable levels of IFX.

Analysis shows that a high concentration of ATI in samples correlates with the presence of neutralizing antibodies that target TNF-α biologics. In some embodiments, assays can be used to detect neutralizing antibodies. Neutralizing antibodies were detected in patient samples with the highest concentrations of ATI. FIG. 9B illustrates that a high concentration of ATI can lead to the presence of neutralizing antibodies and undetectable levels of IFX.

Figure 9C:
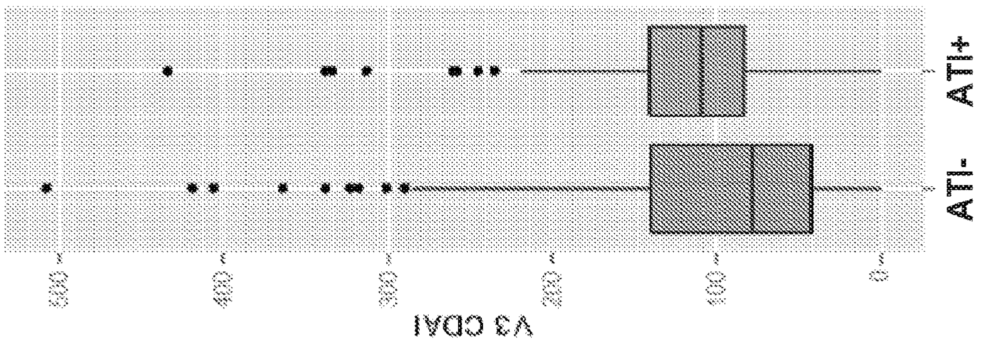
FIG. 9C illustrates that an ATI positive sample determined at an early time point leads to a higher CDAI at a later time point, compared to the lower CDAI level from an ATI negative sample. "V1"=Visit 1; "V3"=Visit 3.
Figure 9D:
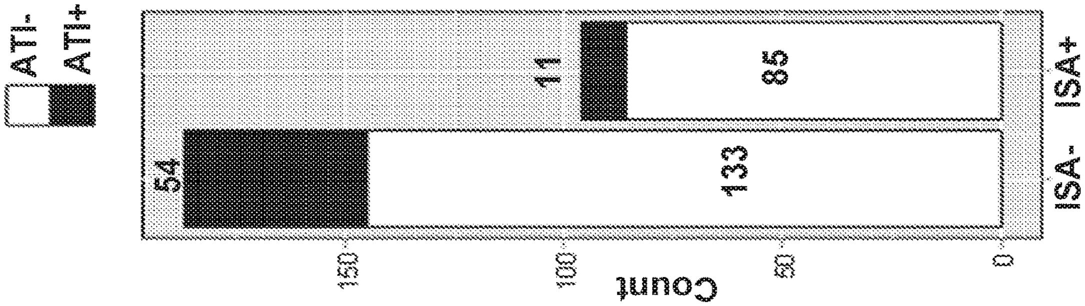
FIG. 9D illustrates that in clinical study #1, patients had lower odds of developing ATI if receiving a combination therapy of infliximab and an immunosuppressant agent (e.g., MTX and AZA).

Longitudinal analysis of the relationship of CDAI and the presence of ATI was evaluated in samples collected at clinic visit #1 and #3 from 283 patients. A correlation between the presence of ATI at visit #1 (V1) was established with CDAI at visit #3 (V3). The median CDAI was 109 at V1 in ATI+ samples, while the median CDAI was 78 in ATI-samples (p=0.027 by Mann Whitney U test). The results indicate a causal relationship between ATI positivity and CDAI. FIG. 9C illustrates that ATI+ samples determined at an early time point were more likely to have a higher CDAI at a later time. The results indicate that disease activity profiling at an early time point can predict CDAI at a later time point. FIG. 9D illustrates that in Clinical Study #1, patients had lower odds of developing ATI if receiving a combination therapy of infliximab (IFX) and an immunosuppressant agent (e.g., MTX and AZA). The odds ratio was 0.320 (p=0.0009 by Fisher's Exact test). In this analysis, ATI positivity (ATI+) was defined as total ATI≥3.13 U/ml.

Example 7. Disease Activity Profiling for TNF-α Mediated Disease Prognosis Using Clinical Study #2 Samples A. Clinical Study #2A This example illustrates the use of a method for monitoring therapeutic efficacy in patients receiving Remicade (inflixamab) alone or in combination with an immunosuppressant agent (e.g., methotrexate, azathioprine and/or corticosteroids). This example describes using methods of the prevent invention to determine the disease activity profiles of samples from a series of clinical trials.

Figure 10D:
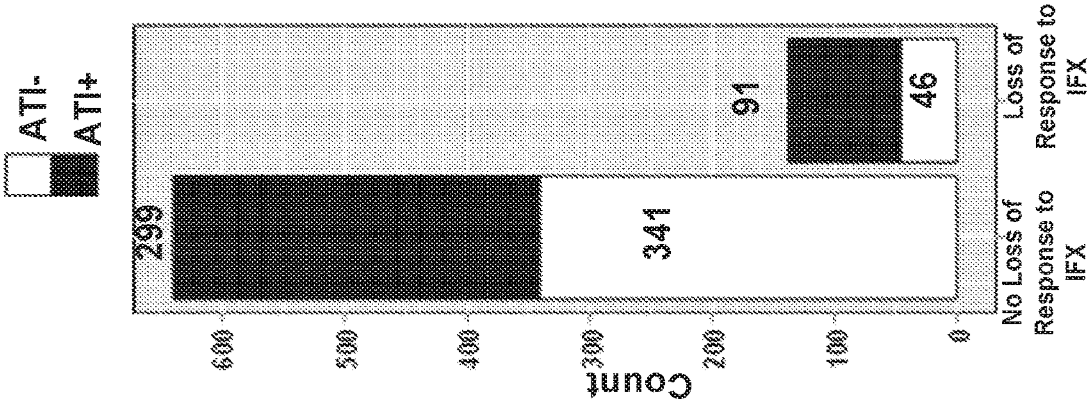
FIG. 10D illustrates the relationship between loss of responsiveness to IFX therapy and the presence of ATI in the study.
Figure 10C:
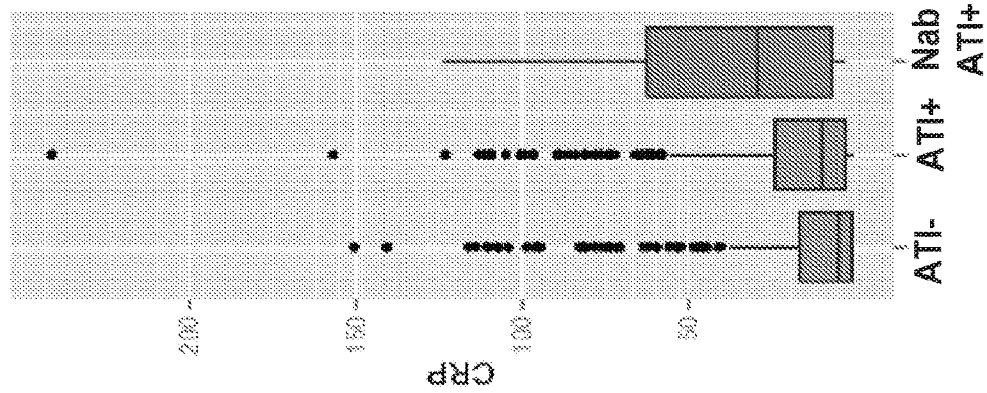
FIG. 10C illustrates the relationship between CRP concentrations and the presence of ATI (ATI and/or neutralizing ATI).
Figure 10B:
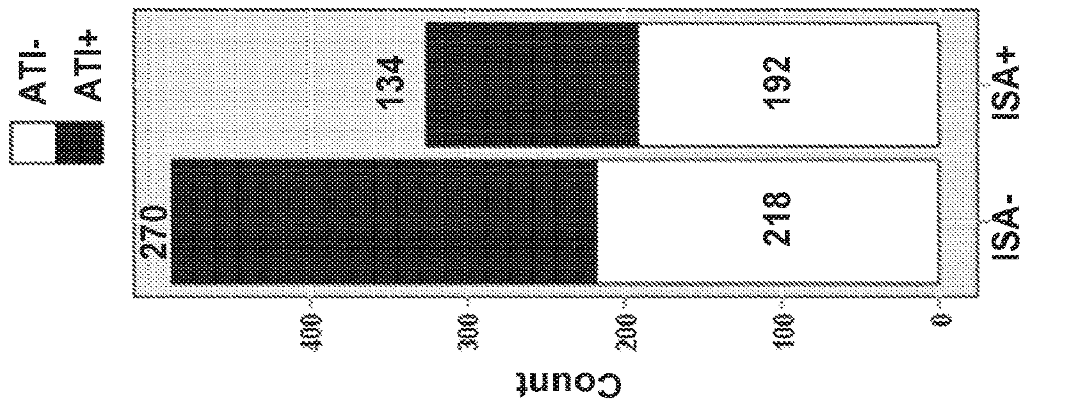
FIG. 10B illustrates the relationship between ISA therapy and the presence of ATI in the study.
Figure 10A:
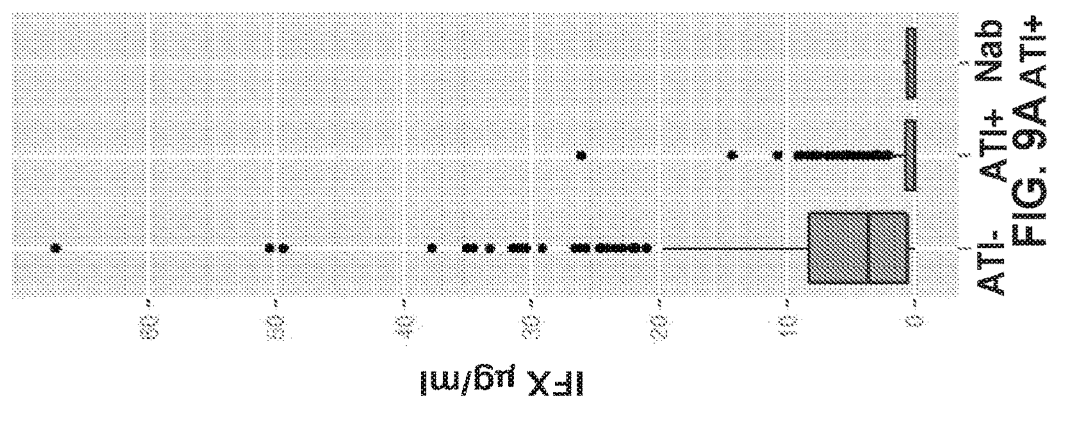
FIG. 10A shows that correlation between IFX concentration and the presence of ATI in samples of clinical study #2A.

In the analysis, we investigated the relationship between antidrug antibodies to inflixamab (ATI) and IFX concentrations in the cohort. It was determined that 90.6% of the patients were ATI+ (58/64), when ATI+ samples were defined to be those with total ATI>3.13 U/ml at at least one time point. The median concentration of IFX in ATI positive samples was 0 μg/ml and 3.74 μg/ml in ATI negative samples ($P<2.2\ 10^{-16}$ by Mann Whitney U Test). The concentration of neutralizing antibodies was 0 in ATI+ samples. The results suggest that the presence of ATI reduces IFX concentration in a patient on IFX therapy. The range of IFX concentration for ATI− samples was 0.0-67.28 μg/ml. In ATI+ samples the IFX concentration was 0.0-26.15 μg/ml. In ATI+ samples with neutralizing antibodies (Nab) the IFX concentration ranged from 0-1.07 μg/ml. FIG. 10A shows that correlation between IFX concentration and the presence of ATI in samples of clinical study #2A. The results also demonstrated that the odds of being ATI positive versus ATI negative are significantly less for samples treated with an immunosuppressant agent (ISA, e.g., methotrexate, azathioprine, corticosteroids, and combinations thereof). In this analysis 814 samples were evaluated. The odds of being ATI+ was significantly less for ISA-treated samples than of being ATI− (odd ratio=0.564; p<0.00001 by Fisher's Exact Test). In addition, fewer ISA treated samples expressed neutralizing ATIs. Of the 34 ATI+ samples with neutralizing antibodies analyzed, 9 of the 34 samples were ISA-treated and 25 samples were non-ISA treated samples. This indicates that ISA therapy can reduce the progression to ATI, and even neutralizing antibodies to IFX. FIG. 10B illustrates the relationship between ISA therapy and the presence of ATI in the study.

Next, we investigated the relationship between ATI and inflammatory markers. As described herein, total ATI BLOQ was set at 0. CRP concentration was determined by methods such as a CEER assay. The results show that the median concentration of CRP was lowest (5.0 μg/ml) in ATI− samples and higher (10.0 μg/ml) in ATI+ samples. Sample expressing neutralizing ATI had a yet higher median concentration of CRP (10.0 μg/ml). All pair-wise comparisons between CRP concentrations and ATI status should that the values were significantly different (p<0.0001 by Mann Whitney U tests). FIG. 10C illustrates the relationship between CRP concentrations and the presence of ATI (ATI and/or neutralizing ATI).

Figure 12A:
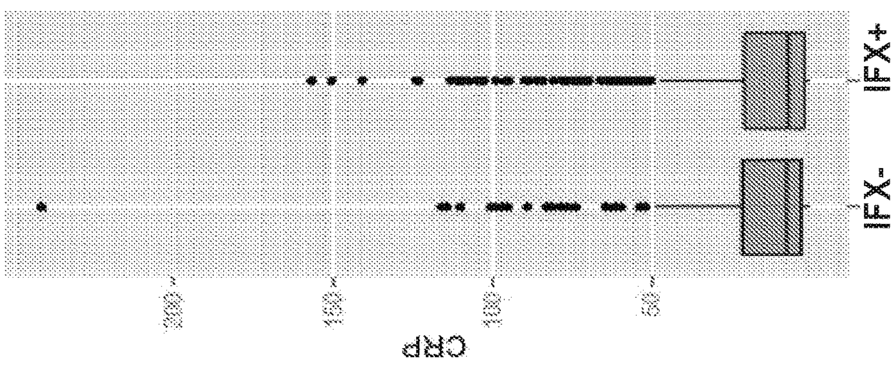
FIG. 12A illustrates the comparison of CRP levels to the presence of IFX.

We also investigated the relationship between ATI and loss of response to therapy. In the cohort, samples were marked as having a "response", "loss of response" and "no information" regarding IFX therapy. The samples were further categorized as being "True" if having a loss of response or "False" if not having a loss of response. In total 777 samples were analyzed. The results showed that in samples marked as "True", there was a significantly higher odds ratio of also being ATI positive (odds ratio=2.254, p<0.0001 by Fisher's Exact Test). Surprisingly, more samples that were positive for neutralizing antibodies to IFX were determined to be responsive to IFX, as compared to being no longer responsive. Of 34 neutralizing ATI+ samples, 21 were marked as "response" and 8 were marked as "loss of response". FIG. 10D illustrates the relationship between loss of responsiveness to IFX therapy and the presence of ATI in the study. FIG. 11 illustrates that levels of ATI and neutralizing antibodies can be determined over time in a series of samples from various patients We compared the concentration of IFX to the presence of the inflammatory marker CRP. We defined "IFX presence" per sample as "True" if IFX was >=0.1 μg/ml which is the LOD of the assay. The results suggest that the median CRP concentration was not different between samples with IFX present or without IFX present. The median CRP level was 7.40 μg/ml in samples with IFX, while median CRP=7.55 μg/ml in samples with IFX absent (p=0.591 by Mann Whitney U Test). FIG. 12A illustrates the comparison of CRP levels to the presence of IFX.

Figure 12B:
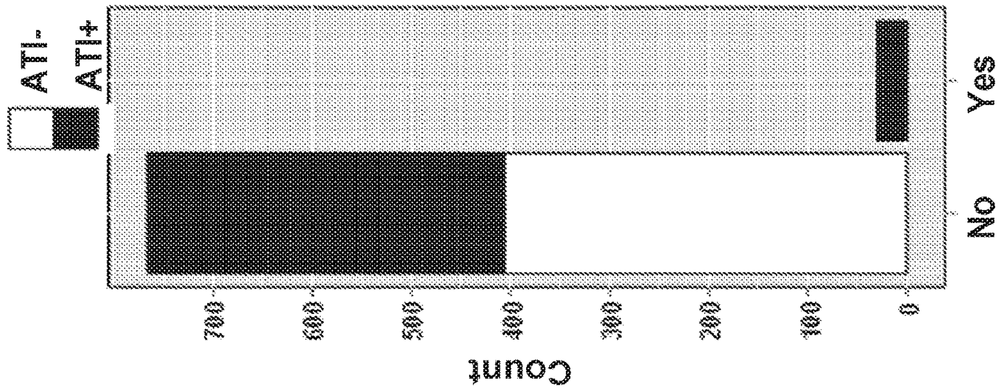
FIG. 12B illustrates the relationship between the presence of ATI and the infusion reaction.

We also compared the relationship between infusion reaction to the presence of ATI. The analysis included a total of 797 samples; 30 samples were categorized as having infusion reaction ("Yes") and 767 samples were categorized as having no infusion reaction ("No"). 29 samples that had an infusion reaction were also ATI+(odds ratio=35.54, p<0.0001 by Fisher's Exact Test). FIG. 12B illustrates the relationship between the presence of ATI and the infusion reaction. Patients expressing ATI were more likely to have had an infusion reaction. Yet, for the 27 samples with neutralizing ATI, no infusion reaction was observed in 22 samples. The remaining 5 samples with neutralizing ATI had infusion reaction.

B. Clinical Study #2B

Figure 12C:
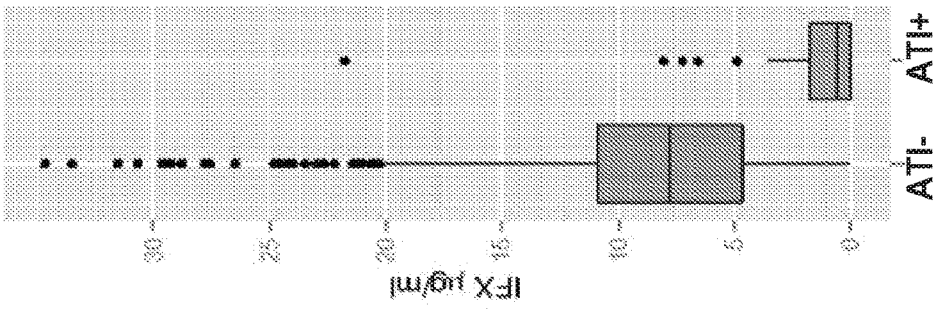
FIG. 12C illustrates the relationship between IFX concentration and the presence of ATI in clinical study #2B.
Figure 12D:
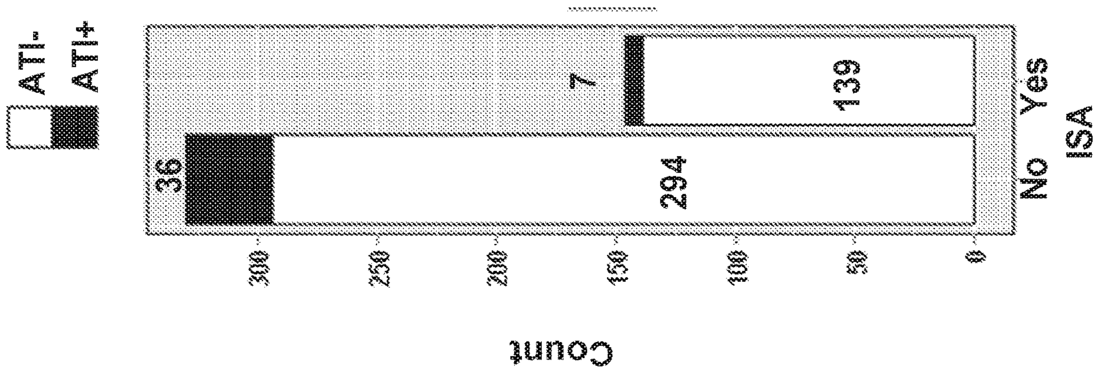
FIG. 12D illustrates the correlation between the presence of ATI and the withdrawal of ISA therapy at a specific, given date.
Figure 13A:
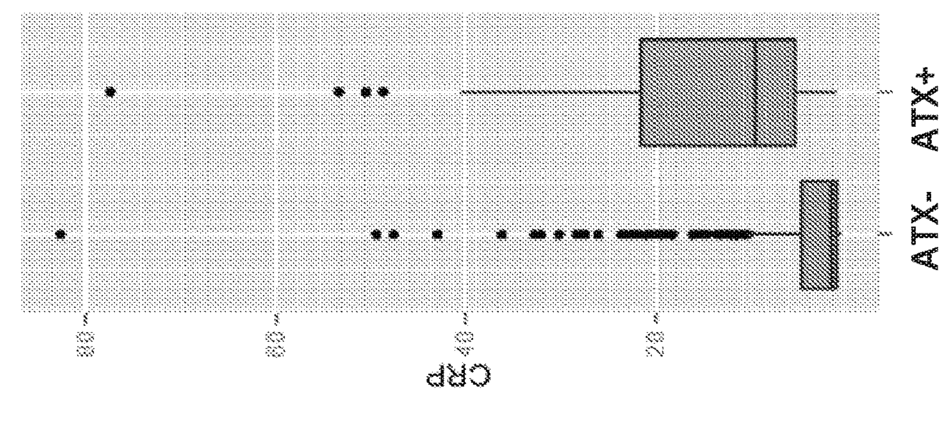
FIG. 13A illustrates the relationship between ATI and the inflammatory marker CRP. Our analysis showed that the odds of experiencing a loss of response to IFX was higher in patients determined to be ATI positive at any time point.
Figure 13B:
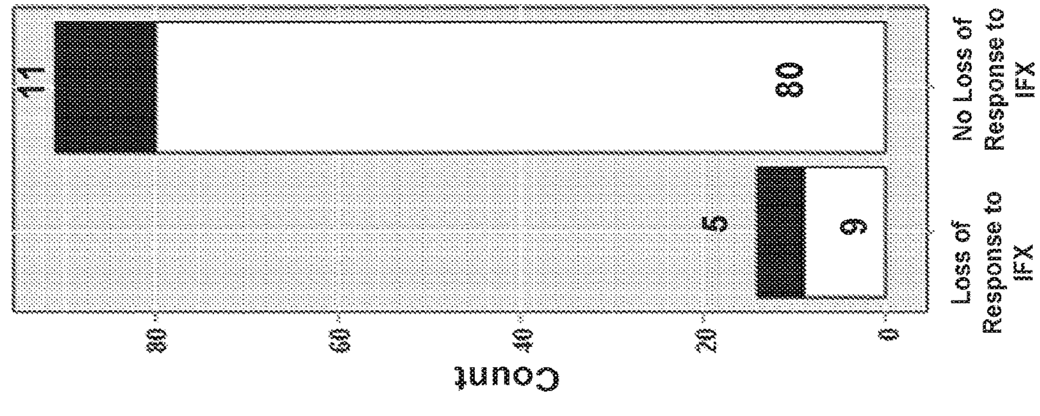
FIG. 13B illustrates the correlation between the presence of ATI at any time point and responsiveness to IFX treatment.
Figure 13C:
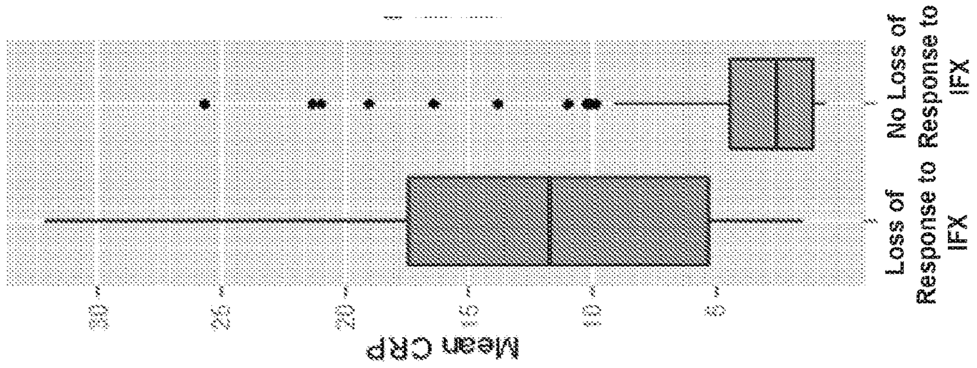
FIG. 13C shows that loss of response can be related to an increase in CRP.
Figure 13D:
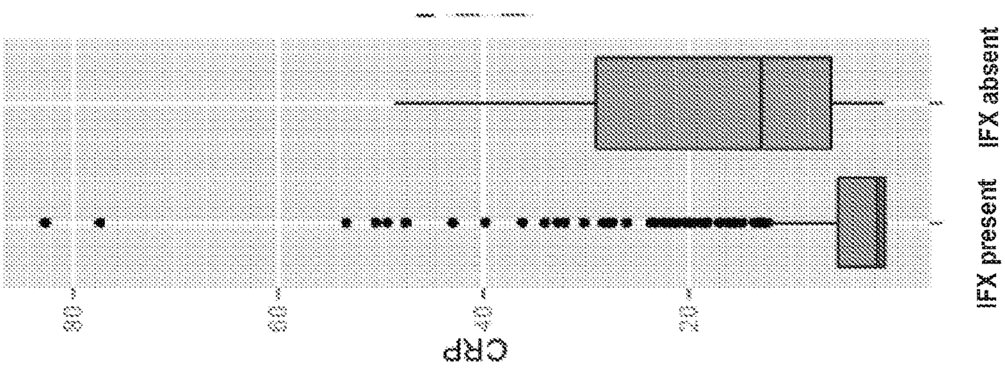
FIG. 13D illustrates the association between the presence of IFX and CRP levels.

In this analysis of clinical study #2B, we investigated the relationships between the presence of ATI, IFX concentration, administration of ISA, the expression of inflammatory markers (e.g., CRP), and loss of response to IFX treatment. We determined that the median IFX concentration was higher in samples expressing ATI compared to those not expressing the antidrug antibodies. 15.2% of the patients (16 out of 105) were ATI+ with a total ATI>3.13 U/ml at at least one time point. Of the 489 samples analyzed, the median IFX concentrations were 0.59 μg/ml in ATI+ samples and 7.78 μg/ml in ATI− samples ($p<2.2\times10^{-16}$ by Mann Whitney U Test). FIG. 12C illustrates the relationship between IFX concentration and the presence of ATI in the cohort. The analysis showed that there are high odds of developing antibodies to IFX when immunosuppressants have been withdrawn (odds ratio=0.412, p=0.0367 by Fisher's Exact Test). FIG. 12D illustrates the correlation between the presence of ATI and the withdrawal of ISA therapy at a specific, given date. We determined that ATI positive samples have a higher median concentration of CRP (9.6 μg/ml, $p=1.25\times10^{-12}$ by Mann Whitney U Test), compared to ATI negative samples (median CRP=1.5 μg/ml). FIG. 13A illustrates the relationship between ATI and the inflammatory marker CRP. Our analysis showed that the odds of experiencing a loss of response to IFX was higher in patients determined to be ATI positive at any time point. (odds ratio=3.967, p=0.0374 for Fisher's Exact Test). FIG. 13B illustrates the correlation between the presence of ATI at any time point and responsiveness to IFX treatment. Loss of response to IFX was also correlated to a higher median concentration of the inflammatory marker CRP. In the analysis there were 14 samples with loss of response at follow-up and 91 samples from responders. The median CRP levels were 11.767 μg/ml for those with loss of response and 2.585 μg/ml for those with response. Patients who had lost response to IFX had a significantly higher mean CRP ($p=7.45\times10^{-5}$ by Mann Whitney U Test). FIG. 13C shows that loss of response can be related to an increase in CRP. CRP was also significantly higher in samples lacking detectable IFX 2. Samples were determined to have IFX ("IFX present") if the level of IFX was >=to 0.1 μg/ml per sample (e.g., LOD of the assay). The median CRP was 1.6 μg/ml in IFX present samples and 13 μg/ml in IFX absent samples ($p=3.69\times10^{-5}$ by Mann Whitney U Test). FIG. 13D illustrates the association between the presence of IFX and CRP levels. In this study "ATI+" was defined as a sample with total ATI>3.13 U/ml at at least one time point.

C. Clinical Study #2C

Figure 14A:
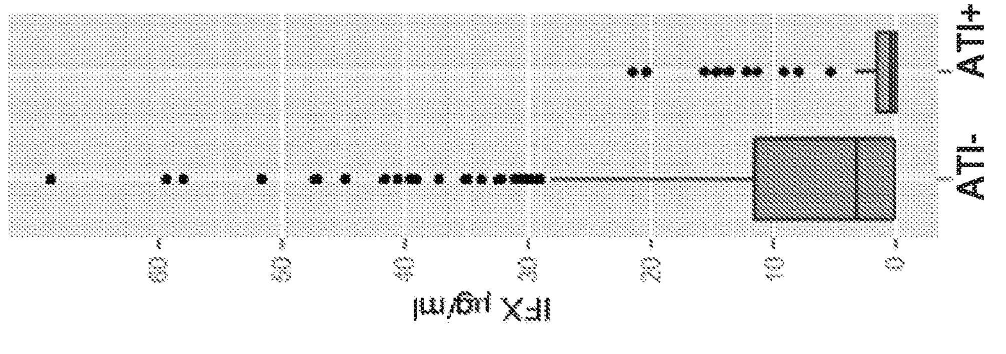
FIG. 14A shows that lower IFX levels are associated with the presence of ATI in clinical study #2C.

In this analysis of clinical study #2C, we investigated the relationship between IFX levels and the presence of ATI. It was determined that ATI+ have a significantly lower median IFX of 0.43 μg/ml as compared to ATI− samples which have a median IFX of 3.28 μg/ml ($p=1.95\times10^{-4}$ by Mann Whitney U test). FIG. 14A shows that lower IFX levels are associated with the presence of ATI.

As such, in one embodiment, the present invention provides a method for determining whether an individual is a candidate for combination therapy wherein said individual is administered infliximab, the method comprising: measuring for the presence or absence of ATI in said individual; and administering an immunosuppressant (e.g., MTX) is the individual has significant levels of ATI. In certain aspects, the concentration level of CRP is indicative of the presence of ATI.

Example 8. Disease Activity Profiling for TNF-α Mediated Disease Prognosis Using Patient Samples from Clinical Study #3

Figure 14B:
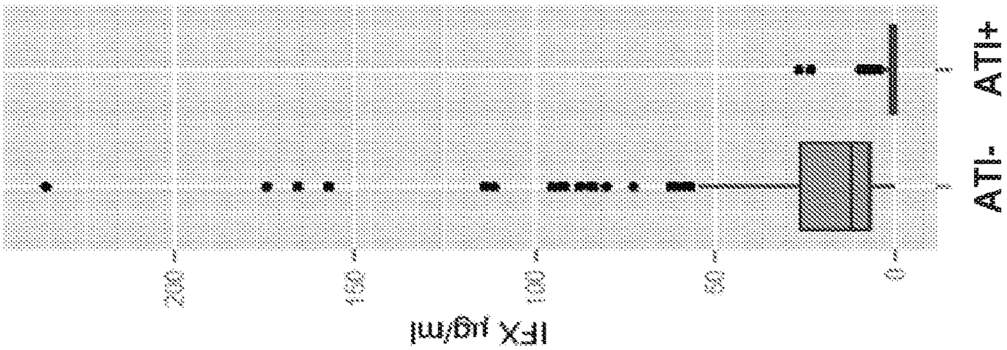
FIG. 14B shows that lower IFX levels are associated with the presence of ATI in clinical study #3.
Figure 14C:
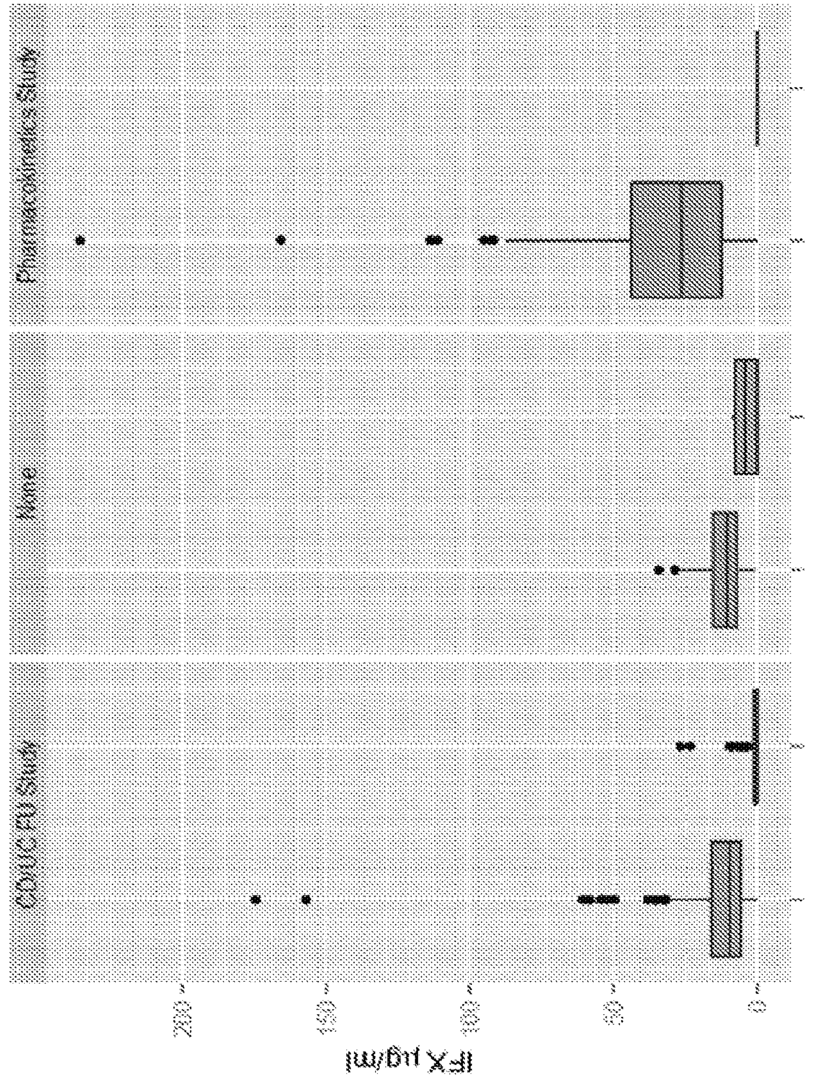
FIG. 14C illustrates that the same correlation between IFX levels and ATI was also present in the study data, follow-up study and in the pharmacokinetics study.
Figure 15A:
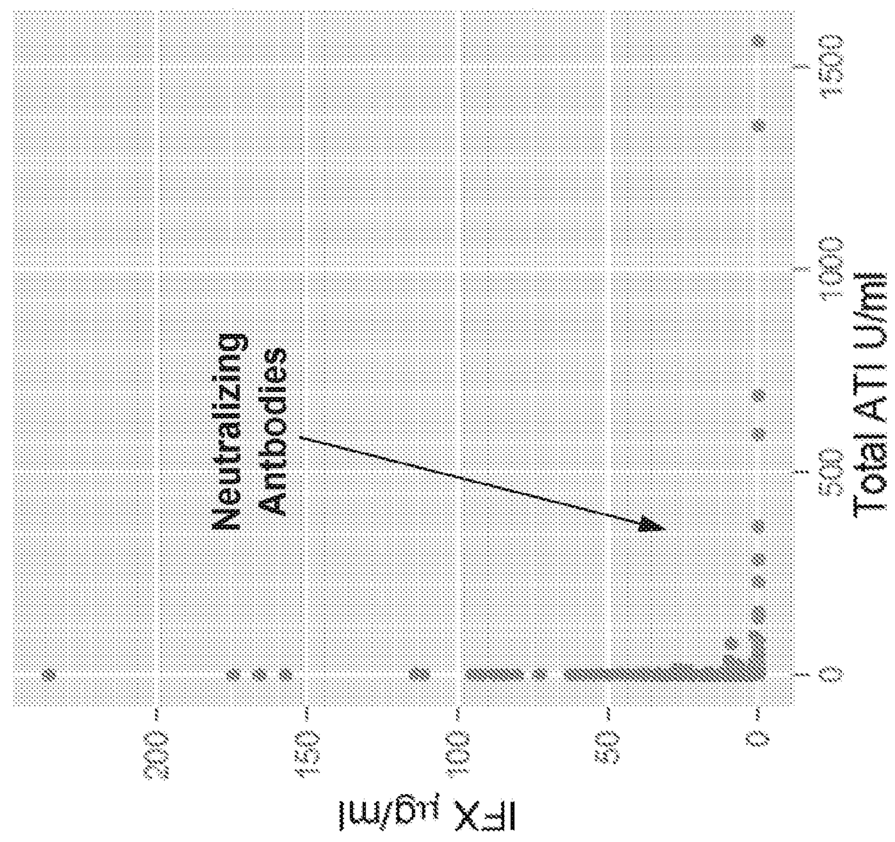
FIG. 15A illustrates the relationship between ATI levels and IFX. It was determined that samples with high concentration ATI are neutralizing on IFX and thus, IFX concentration was determined to be 0 μg/ml.

This example illustrates using methods of the present invention to monitor the therapeutic efficacy of anti-TNF drug therapy. In particular, pooled data including study data, pharmacokinetics data, follow-up study data of clinical study #3 were analyzed. The results showed that the median IFX concentration of 0.0 μg/ml was lower in ATI positive samples compared to an IFX concentration of 12.21 μg/ml ATI negative samples (P<2.2x10-16 by Mann Whitney U test). FIG. 14B shows that lower IFX levels are associated with the presence of ATI in these clinical samples. FIG. 14C illustrates that the same correlation between IFX levels and ATI was also present in the study data, follow-up study and in the pharmacokinetics study ($p<0.05$ by Mann Whitney U tests). We also used methods of the present invention to determine that a high concentration of ATI in a sample have a neutralizing effect on IFX. In particular, high concentrations of ATI act as neutralizing antibodies to inflixamab. Samples with a high concentration of ATI had an IFX level of 0 μg/ml. FIG. 15A illustrates the relationship between ATI levels including neutralizing ATI and IFX.

Figure 15B:
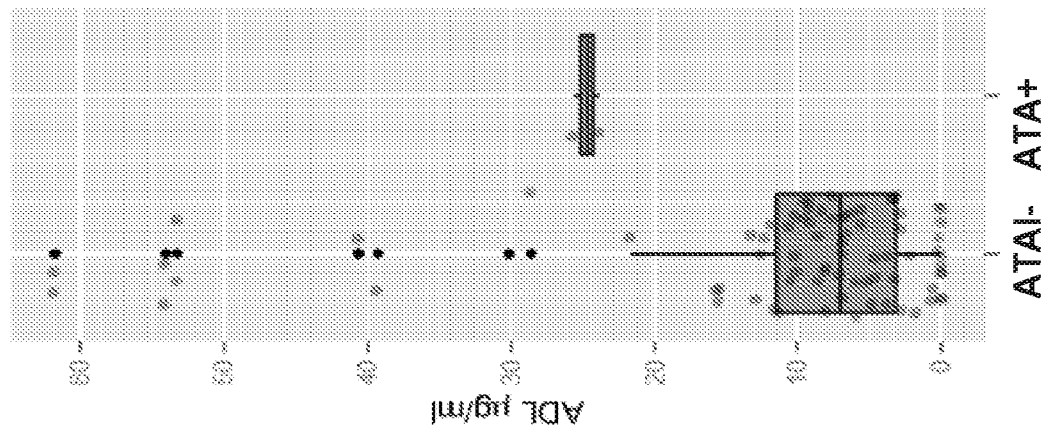
FIG. 15B illustrates an association between ADL concentration and the presence of ATA in patient samples.

Example 9. Methods of Disease Activity Profiling Including the PRO Inflammatory Index in Patients Receiving Humira This example illustrates methods of the present invention including determining the level of TNF-α, biologic (e.g., adalimumab (Humira); ADL) and the presence of anti-drug antibodies to the TNF-α biologic (e.g., ATA) in a patient sample. In this analysis, one sample represents one patient and a total of 98 CD samples were evaluated. 2.04% (2 out of 98 CD patients) of the samples were positive for ATA, when ATA positivity was set as total ATA>0. Surprisingly, the two ATA positive samples also had the highest concentrations of ADL. FIG. 15B illustrates an association between ADL concentration and the presence of ATA in patient samples.

Figures 16A, 16B:
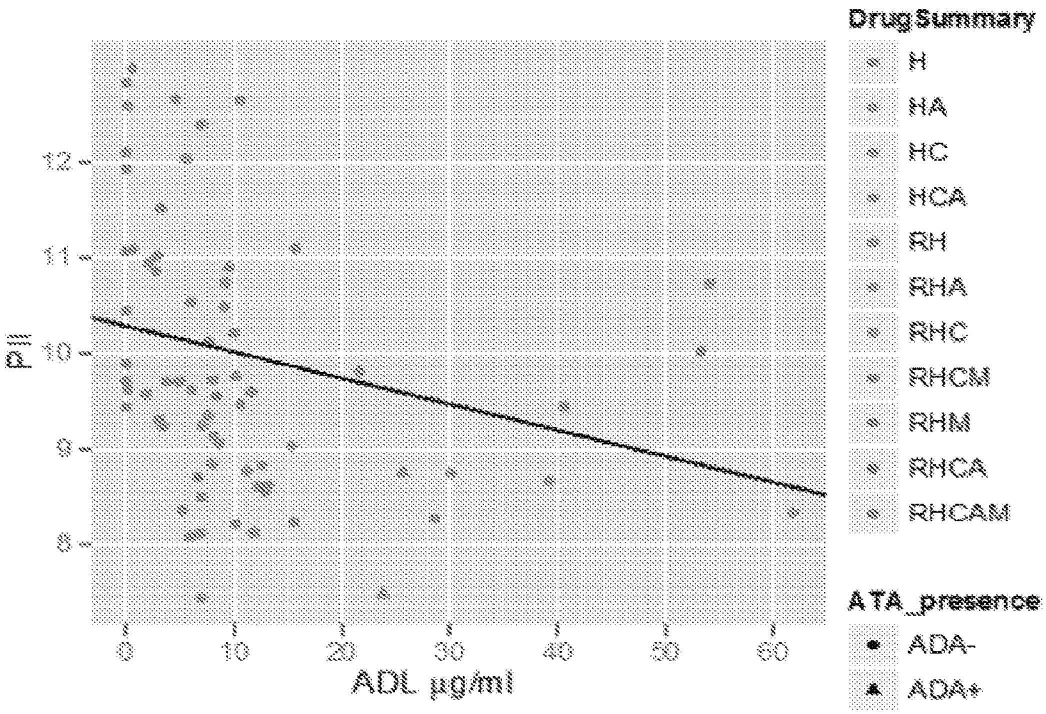
FIG. 16A describes the details of an exemplary PRO Inflammatory Index.
FIG. 16B illustrates that there is no obvious relationship between the PII and the concentration of ADL in an array of samples with ADL alone or in combination with other drugs.

This example describes an exemplary PRO Inflammatory Index (PII). The example also illustrates the use of the PII in patient samples receiving Humira (adalimumab) and different drug combinations. FIG. 16A describes the details of an exemplary PRO Inflammatory Index. The PII can represent a single per-sample score describing inflammation levels based on five biomarkers. The score is obtained from the logarithmic transformation of the sum of the five biomarkers. In some embodiments, the biomarkers include VEGF in μg/ml, CRP in ng/ml, SAA in ng/ml, ICAM in ng/ml and VCAM in ng/ml. FIG. 16B illustrates that there is no obvious relationship between the PII and the concentration of ADL in an array of samples with ADL alone or in combination with other drugs. This could be due to the appearance of high ADL trough serum concentration in the sample cohort. These is a significant negative correlation between PII and ADL concentration ($p=1.66\times10^{5}$ and Spearman's Rho=−0.459). A similar negative correlation relationship was found between IFX and PII.

Figure 17:
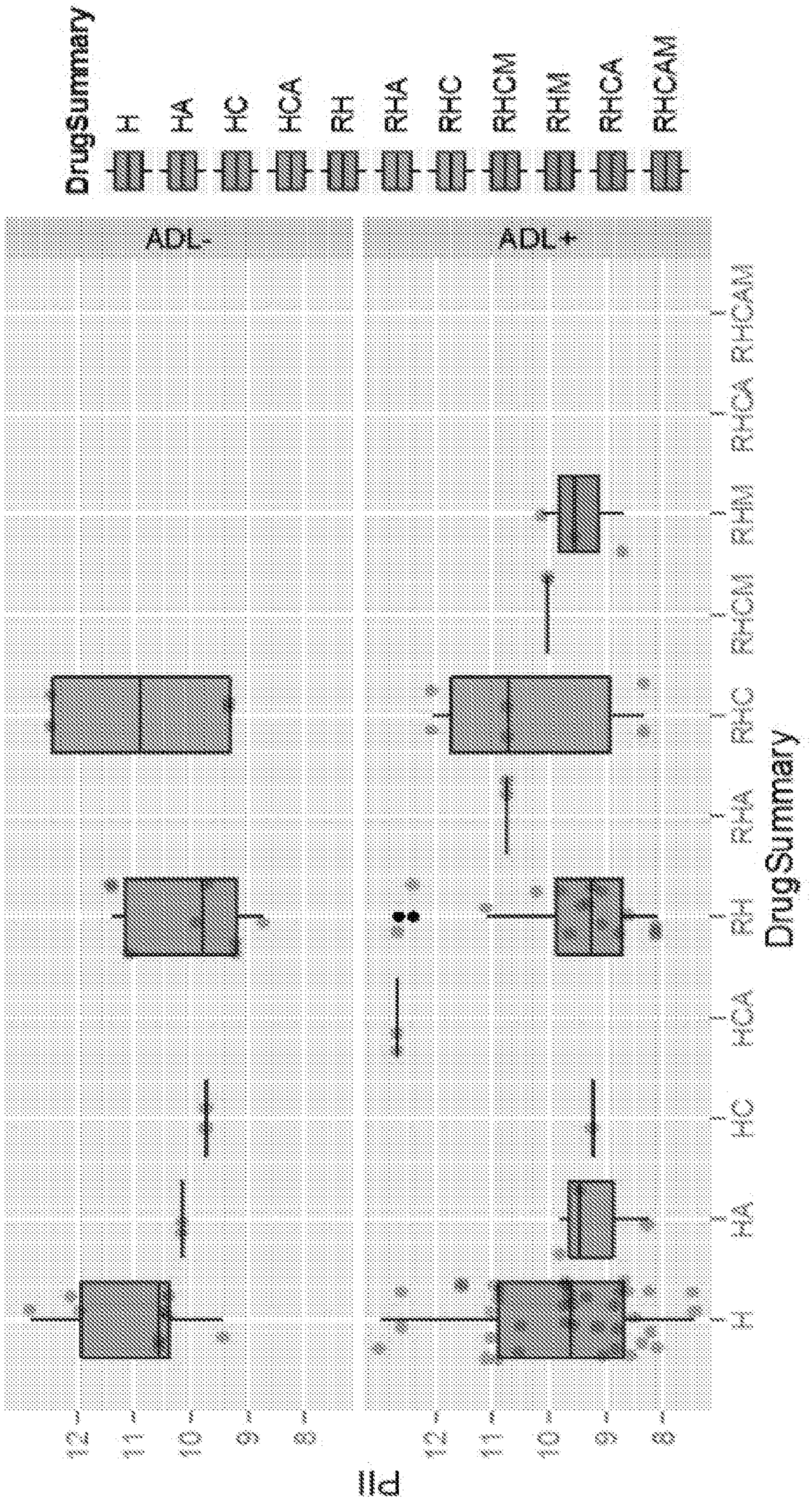
FIG. 17 shows a plot of the PII scores for patients receiving Humira and Humira in combination with other drug such as Remicade, Cimzia, Azathioprine and Methotrexate.

We also compared the relationship between the PII and the presence of therapeutic agents used to treat TNF-α mediated diseases. ADL positive samples were defined as samples with an ADL concentration of greater than 0 μg/ml. The results showed that a higher PII was detected in patients on Humira compared to patients on Remicade and Humira. FIG. 17 shows a plot of the PII scores for patients receiving Humira and Humira in combination with other drug such as Remicade, Cimzia, Asathioprine and Methotrexate.

As such, in one embodiment, the present invention provides a method for monitoring Crohn's disease activity, the method comprising:

determining an inflammatory index comprising the measurement of a panel of markers comprising VEGF in μg/ml, CRP in ng/ml, SAA in ng/ml, ICAM in ng/ml and VCAM in ng/ml;

comparing the index to an efficacy scale or index to monitor and manage the disease.

Example 10. Methods for Improved Patient Management

This example describes methods for improved patient management to assist in developing personalized patient treatment.

In some embodiments, patients with active CD and UC can be analyzed using a mobility shift assay (see, e.g., PCT Publication No. WO 2011/056590, the disclosure of which is hereby incorporated by reference in its entirety for all purposes) in conjunction with disease activity profiling. FIG. 18 shows details of the methods of the present invention for improving the management of patients with CD and/or UC. In some embodiments, the methods of disease activity profiling comprise pharmacokinetics, and determining the presence and/or levels of disease activity profile markers and/or mucosal healing markers.

In some embodiments, disease activity profiling comprises methods of detecting, measuring, and determining the presence and/or levels of biomarkers, cytokines, and/or growth factors. Non-limiting examples of cytokines that can be used in disease activity profiling include bFGF, TNF-α, IL-10, IL-12p70, IL-10, IL-2, IL-6, GM-CSF, IL-13, IFN-γ, TGF-β1, TGF-β2, TGF-β3, and combinations thereof. Non-limiting examples of inflammatory markers include SAA, CRP, ICAM, VCAM, and combinations thereof. Non-limiting examples of anti-inflammatory markers include TGF-β, IL-10, and combinations thereof. Non-limiting examples of growth factors include amphiregulin (AREG), epiregulin (EREG), heparin binding epidermal growth factor (HB-EGF), hepatocye growth factor (HGF), heregulin-β1 (HRG) and isoforms, neuregulins (NRG1, NRG2, NRG3, NRG4), betacellulin (BTC), epidermal growth factor (EGF), insulin growth factor-1 (IGF-1), transforming growth factor (TGF), platelet-derived growth factor (PDGF), vascular endothelial growth factor (VEGF), stem cell factor (SCF), platelet derived growth factor (PDGF), soluble fms-like tyrosine kinase 1 (sFlt1), placenta growth factor (PIGF), fibroblast growth factors (FGFs), and combinations thereof.

In other embodiments, disease activity profiling comprises detecting, measuring and determining pharmacokinetics and mucosal healing. In some aspects, mucosal healing can be assessed by the presence and/or level of selected biomarkers and/or endoscopy. In some instances, mucosal healing can be defined as the absence of friability, blood, erosions and ulcers in all visualized segments of gut mucosa. In some embodiments, biomarkers of mucosal healing, include, but are not limited to, AREG, EREG, HG-EGF, HGF, NRG1, NRG2, NRG3, NRG4, BTC, EGF, IGF-1, HRG, FGF1, FGF2 (bFGF), FGF7, FGF9, SCF, PDGF, TWEAK, GM-CSF, TNF-α, IL-12p70, IL-1β, Il-2, IL-6, IL-10, IL-13, IFN-γ, TGF-α, TGF-β1, TGF-β2, TGF-β3, SAA, CRP, ICAM, VCAM, and combinations thereof. In some embodiments, a growth factor index can be established using statistical analyses of the detected levels of biomarkers of mucosal healing. In some instances, the growth factor index can be associated with other markers of disease activity, and utilized in methods of the present invention to personalize patient treatment.

Figure 19:
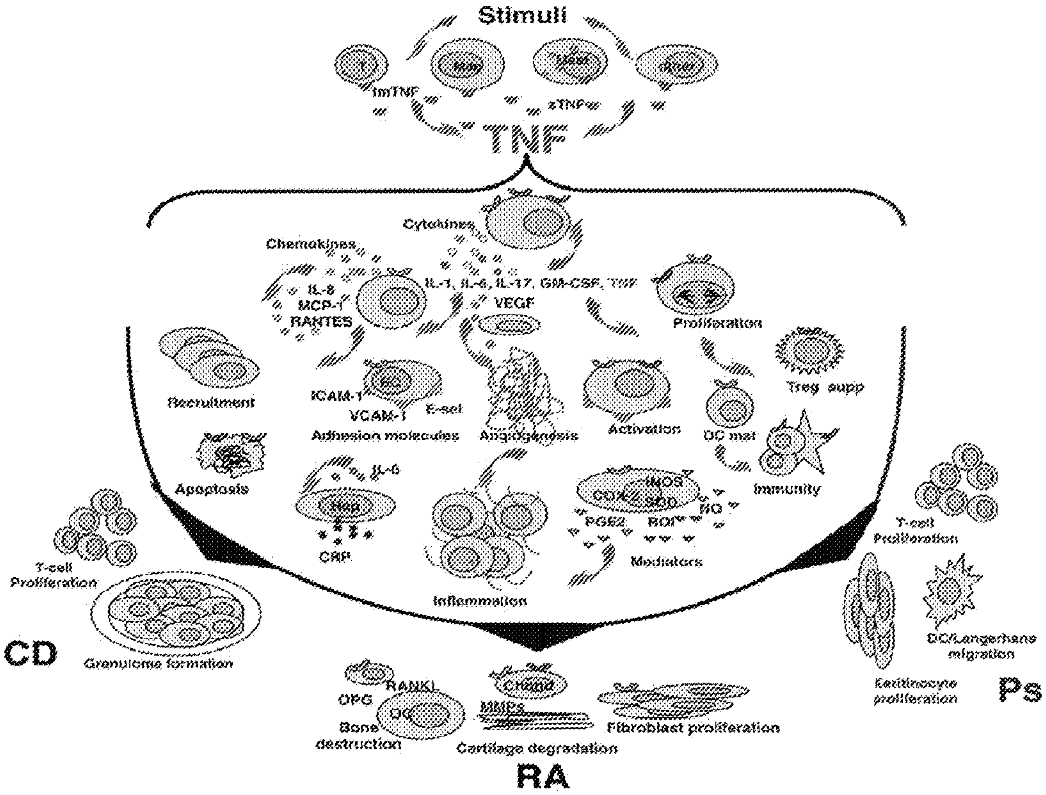
FIG. 19 shows the effect of the TNF-α pathway and related pathways on different cell types, cellular mechanisms and disease (e.g., Crohn's Disease (CD), rheumatoid arthritis (RA) and Psoriasis (Ps)).
Figure 20:
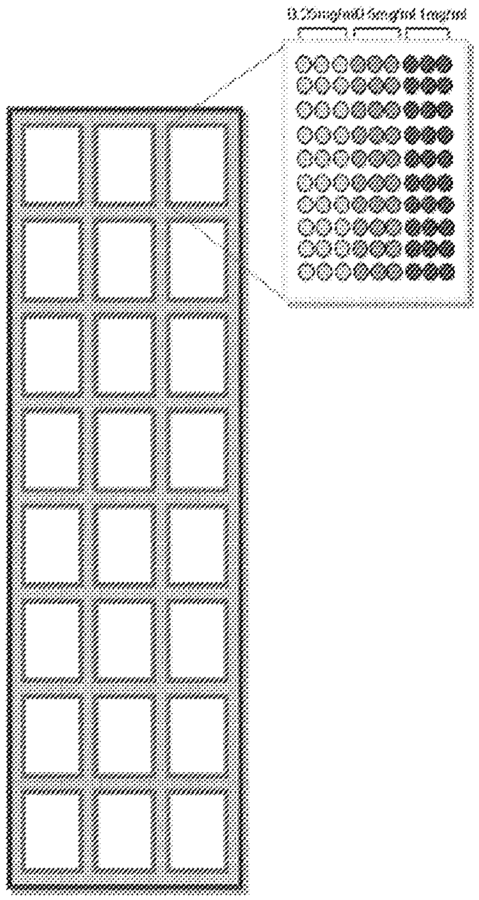
FIG. 20 illustrates an exemplary CEER multiplex growth factor array.
Figure 21A:
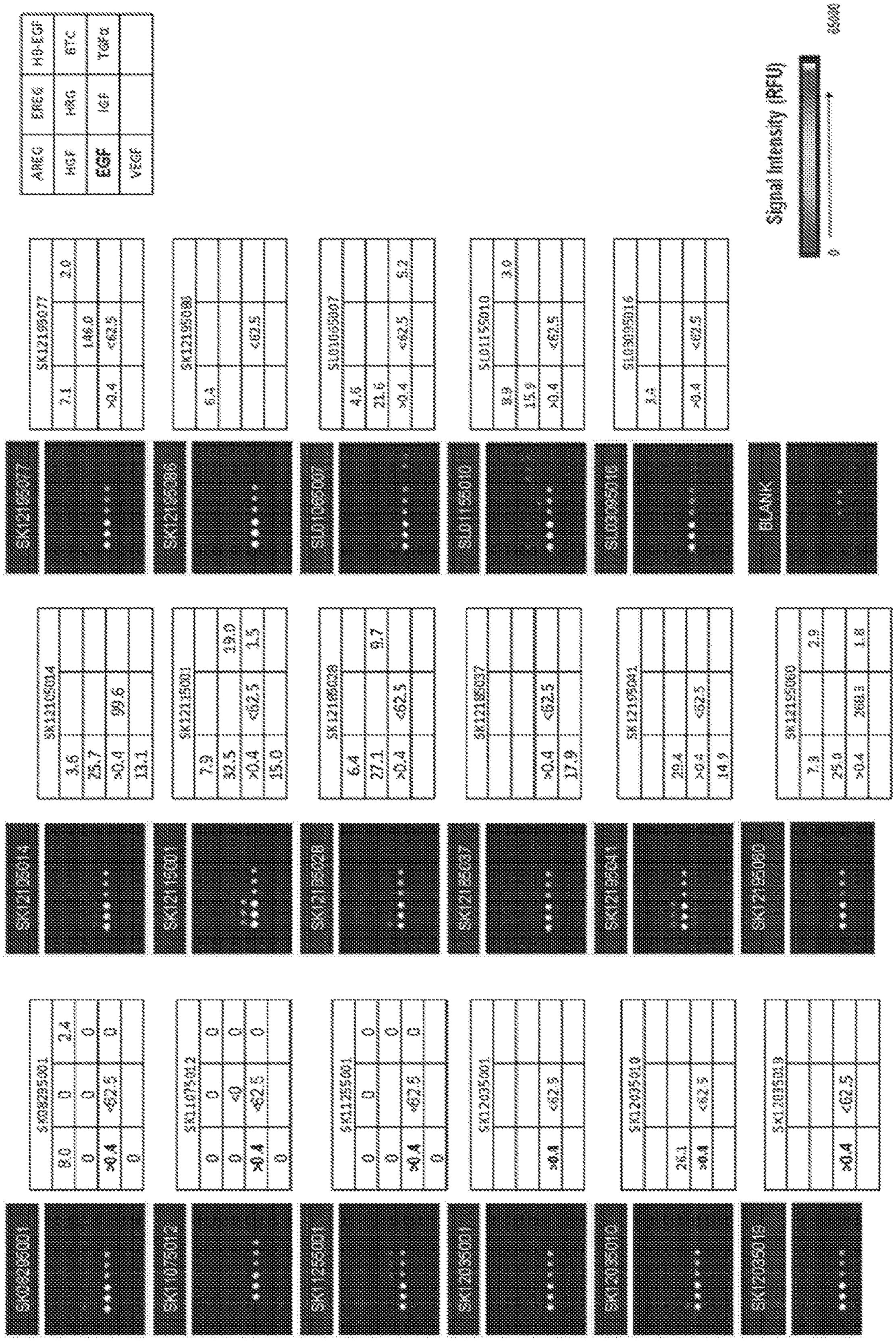
Figure 21C:
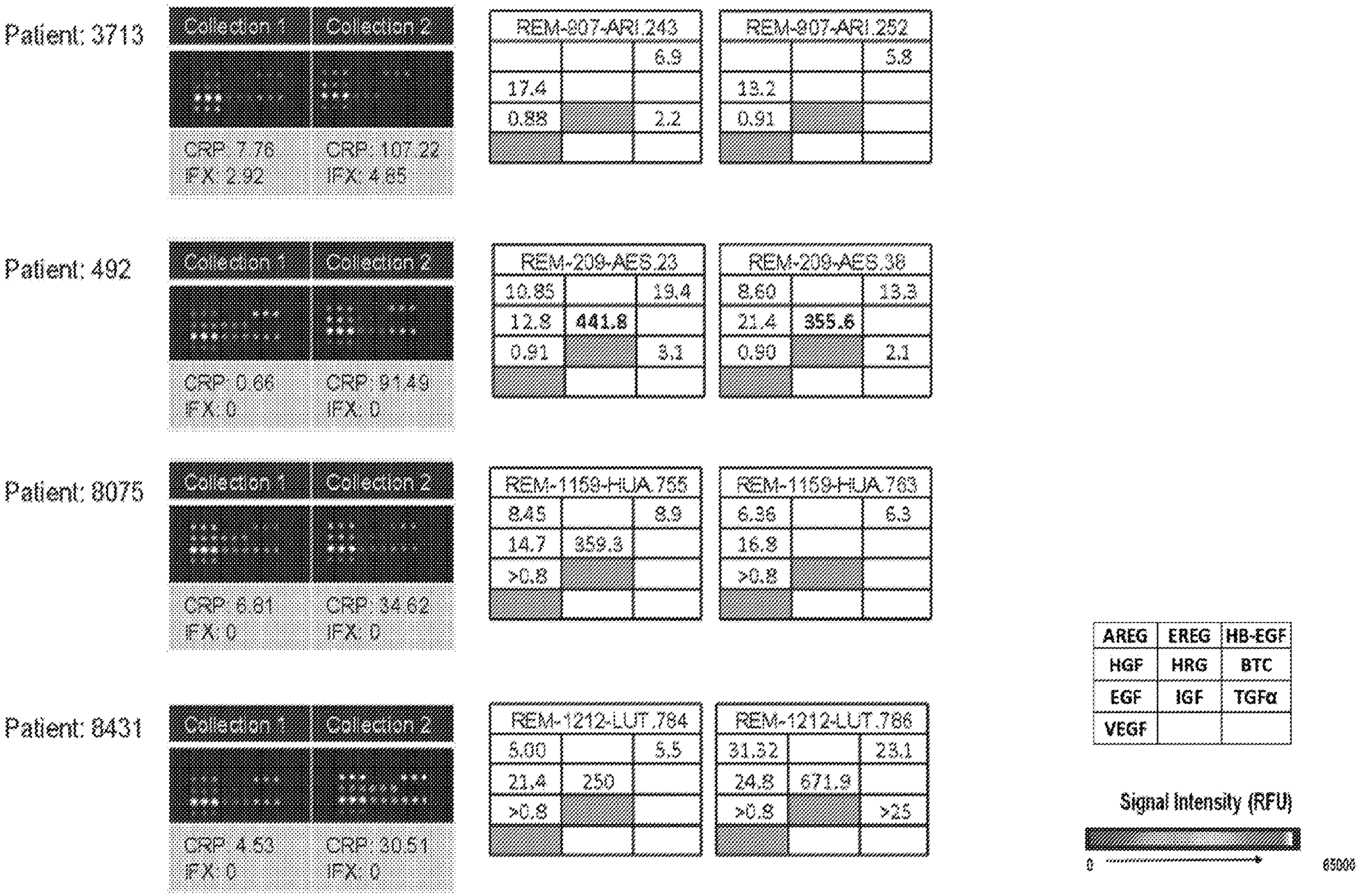
Figure 21F:
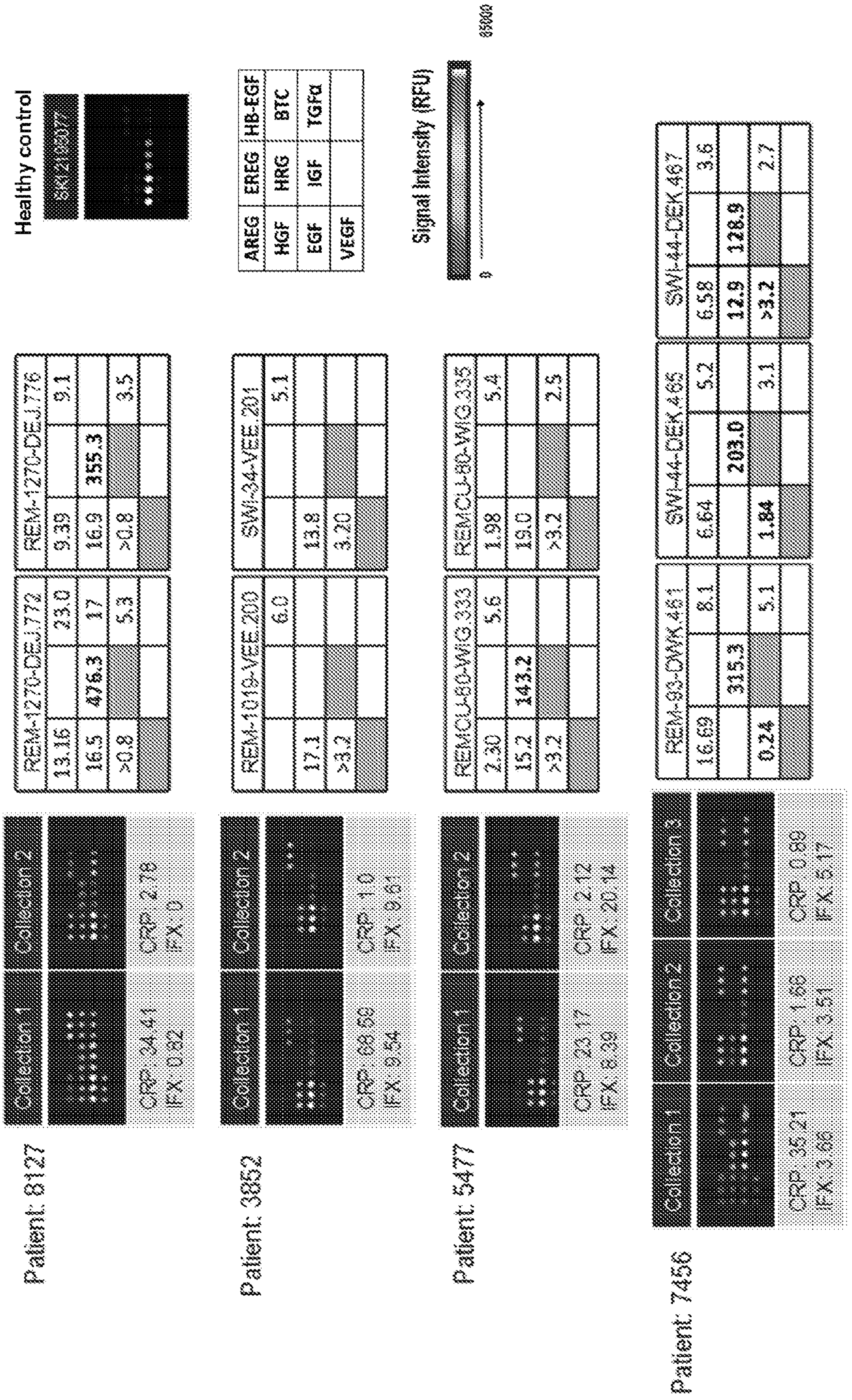
Figure 21G:
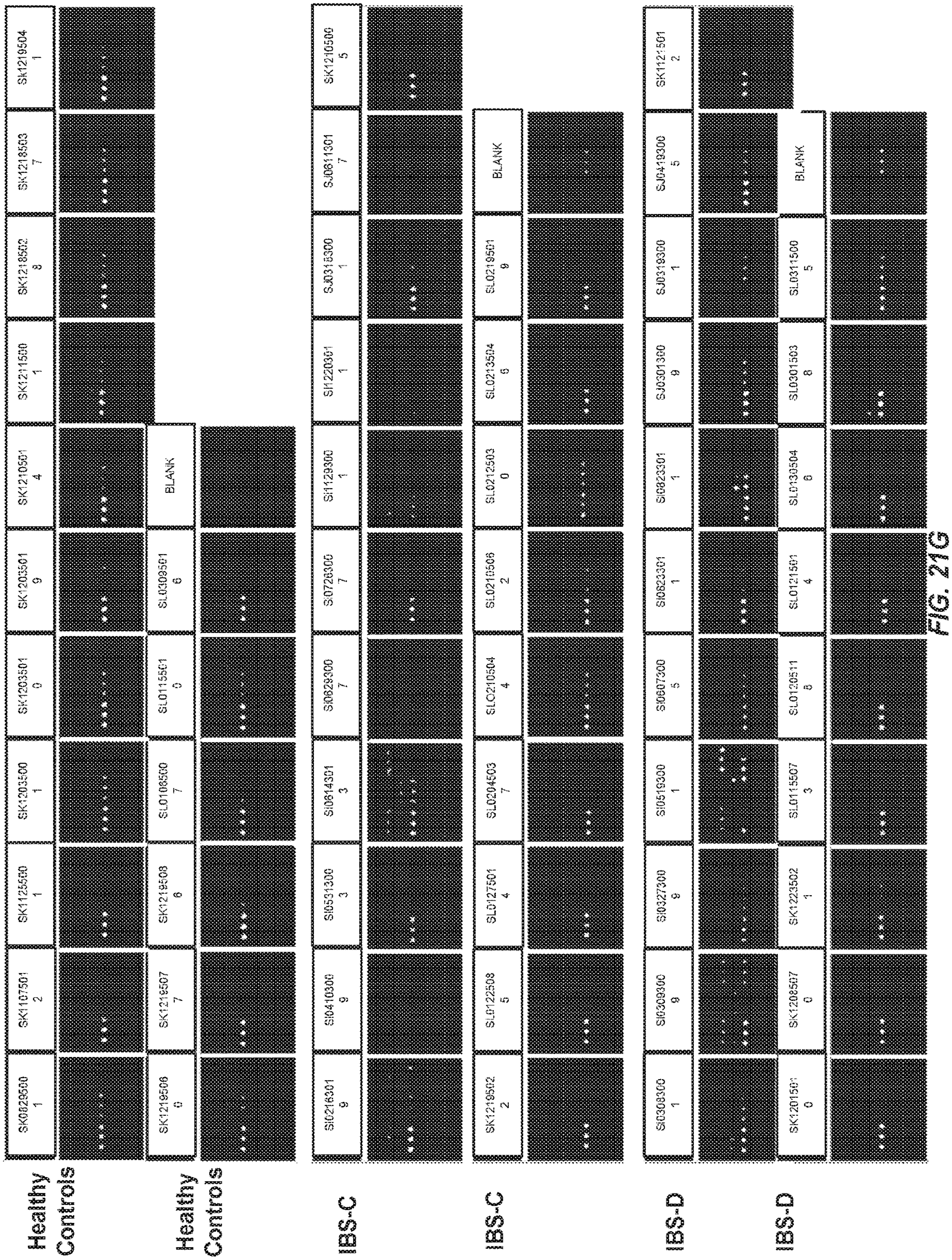

FIG. 19 shows the effect of the TNF-α pathway and related pathways on different cell types, cellular mechanisms and disease (e.g., Crohn's Disease (CD), rheumatoid arthritis (RA) and Psoriasis (Ps)). FIG. 20 illustrates a schematic of an exemplary CEER multiplex growth factor array. In particular embodiments, the methods of the present invention can employ this array. As non-limiting examples, FIG. 21A-F illustrate multiplexed growth factor profiling of patient samples using this array. In particular, longitudinal analysis of growth factors, such as AREG, EREG, B-EGF, HGF, RG. BTC, EGF, GF, TGFα, and VEGF, was performed on a collection of patient samples. FIGS. 21B and E illustrate the determination of the level of serological and immune markers, such as ASCA-a, ASCA-g, Cbirl and OmpC, in samples from Patient 10109, Patient 10118 and Patient 10308. FIG. 21G shows the exemplary growth factor arrays performed on samples from healthy controls, patients with mBS-C, and patients with IBS-D.

A series of multiplexed CEER growth factor and CRP arrays was performed on patient samples. Tables A-D (below) highlight longitudinal analysis of mucosal healing in patient samples. The following Table (A) shows that CR9 and growth factors can be predictive of mucosal healing:

| Subject ID | Collection Date | CRP | | EGF | | bFGF | | VEGF | | FGF1 | | Tweak | | TGF beta1 | | TGF beta2 | |
|---|---|---|---|---|---|---|---|---|---|---|---|---|---|---|---|---|---|
| 10101 | Collection 1 | 3.98 | | 315.67 | | 4.83 | | 1454.94 | | 15.16 | | 0.65 | | 68.64 | | 964.02 | |
| 10101 | Collection 2 | 0.13 | N | 365.74 | P | 3.79 | N | 1201.53 | N | 15.37 | P | 6.39 | P | 78.52 | P | 562.77 | N |
| 10103 | Collection 1 | 0.66 | | 439.03 | | 4.00 | | 969.78 | | 17.86 | | 35.05 | | 67.68 | | 300.36 | |
| 10103 | Collection 2 | 15.44 | P | 372.64 | N | 3.90 | N | 881.27 | N | 17.00 | N | 35.50 | P | 73.85 | P | 311.76 | P |
| 10109 | Collection 1 | 15.86 | | 418.89 | | 1.66 | | 223.85 | | 13.52 | | 6.35 | | 63.79 | | 386.64 | |
| 10109 | Collection 2 | 1.22 | N | 162.75 | N | 0.49 | N | 177.42 | N | 15.66 | P | 5.69 | N | 57.93 | N | 544.34 | P |
| 10118 | Collection 1 | 0.41 | | 126.86 | | 1.31 | | 1173.42 | | 13.11 | | 9.51 | | 71.43 | | 339.43 | |
| 10118 | Collection 2 | 3.54 | P | 282.16 | P | 3.03 | P | 1200.74 | P | 14.43 | P | 1.92 | N | 68.69 | N | 920.00 | P |
| 10308 | Collection 1 | 1.80 | | 336.45 | | 2.23 | | 1361.03 | | 15.05 | | 5.35 | | 98.94 | | 730.52 | |
| 10308 | Collection 2 | 155.95 | P | 525.57 | P | 23.83 | P | 3233.27 | P | 15.34 | P | 11.18 | P | 153.21 | P | 466.49 | N |
| 10503 | Collection 1 | 2.10 | | 237.62 | | 6.76 | | 760.17 | | 13.63 | | 13.07 | | 64.72 | | 475.00 | |
| 10503 | Collection 2 | 27.39 | P | 215.81 | N | 3.59 | N | 1135.46 | P | 11.81 | N | 61.50 | P | 90.11 | P | 737.82 | P |
| 11003 | Collection 1 | 6.32 | | | | 1.58 | | 408.49 | | 14.06 | | 7.69 | | 40.53 | | 395.19 | |
| 11003 | Collection 2 | 0.16 | N | 123.57 | | 1.90 | P | 394.88 | N | 14.81 | P | 5.12 | N | 35.85 | N | 221.67 | N |
| 11601 | Collection 1 | 0.23 | | 241.76 | | 3.36 | | 173.02 | | 15.43 | | 2.54 | | 46.92 | | 589.91 | |
| 11601 | Collection 2 | 0.92 | P | 310.64 | P | 6.89 | P | 169.40 | N | 17.31 | P | 12.50 | P | 61.67 | P | 514.21 | N |
| 11602 | Collection 1 | 1.71 | | 327.92 | | 15.31 | | 562.30 | | 12.82 | | 12.13 | | 58.15 | | 1120.06 | |
| 11602 | Collection 2 | 1.93 | P | 338.88 | P | 4.83 | N | 334.69 | N | 12.36 | N | 14.61 | P | 59.83 | P | 1599.43 | P |
| 12121 | Collection 1 | 6.85 | | 484.22 | | 4.89 | | 477.49 | | 11.90 | | 25.90 | | 35.44 | | 1307.92 | |
| 12121 | Collection 2 | 2.16 | N | 607.95 | P | 4.72 | N | 842.54 | P | 11.13 | N | 10.93 | N | 43.32 | P | 1284.24 | N |
| 12121 | Collection 3 | 58.64 | P | 458.80 | N | 0.81 | N | 286.72 | N | 12.38 | P | 6.71 | N | 60.23 | P | 631.34 | N |
| 190 | Collection 1 | 0.74 | | 353.47 | | | | 252.71 | | | | 1.63 | | 22.79 | | | |
| 190 | Collection 2 | 25.18 | P | 941.21 | P | | | 656.11 | P | | | 4.71 | P | 84.07 | P | | |
| 492 | Collection 1 | 0.66 | | | | | | 351.79 | | | | 3.61 | | 20.02 | | | |

-continued

| Subject ID | Collection Date | CRP | | EGF | | bFGF | | VEGF | | FGF1 | | Tweak | | TGF beta1 | | TGF beta2 | |
|---|---|---|---|---|---|---|---|---|---|---|---|---|---|---|---|---|---|
| 492 | Collection 2 | 91.49 | P | | | | | 962.96 | P | | | | | 27.89 | P | | |
| 2546 | Collection 1 | 4.73 | | 857.25 | | | | 866.87 | | | | 10.37 | | 31.01 | | | |
| 2546 | Collection 2 | 28.18 | P | 805.11 | N | | | 826.44 | N | | | 7.23 | N | 56.28 | P | | |

"N" and "P" denote a negative or positive relationship between pairs of observations for each marker, respectively per subject.
Underlined data are number pairs above upper limit of quantitation and are assumed to have a positive relationship.

The following Table B lists CRP and growth factors predictive of mucosal healing:

| Subject ID | Collection Date | CRP | | AREG | | HGF | | HRG | | HB EGF | | BTC | | TGF alpha | |
|---|---|---|---|---|---|---|---|---|---|---|---|---|---|---|---|
| 10101 | Collection 1 | 3.98 | | 12.16 | | 26.60 | | 143.10 | | 6.60 | | 0.00 | | 3.10 | |
| 10101 | Collection 2 | 0.13 | N | 9.91 | N | 23.90 | N | 46.50 | N | 5.00 | N | 0.00 | | 2.00 | N |
| 10103 | Collection 1 | 0.66 | | 26.06 | | 41.30 | | 2000.00 | | 17.80 | | 0.00 | | 6.60 | |
| 10103 | Collection 2 | 15.44 | P | 50.00 | P | 82.70 | P | 2000.00 | P | 18.10 | P | 0.00 | | 6.60 | P |
| 10109 | Collection 1 | 15.86 | | 13.81 | | 27.40 | | 243.10 | | 7.80 | | 0.00 | | 3.30 | |
| 10109 | Collection 2 | 1.22 | N | 9.71 | N | 0.00 | N | 95.60 | N | 6.30 | N | 0.00 | | 2.60 | N |
| 10118 | Collection 1 | 0.41 | | 27.10 | | 26.12 | | 541.30 | | 10.51 | | 0.00 | | 7.07 | |
| 10118 | Collection 2 | 3.54 | P | 21.40 | N | 29.95 | P | 492.70 | P | 7.83 | N | 26.00 | P | 6.42 | P |
| 10308 | Collection 1 | 1.80 | | 0.00 | | 45.10 | | 0.00 | | 4.28 | | 0.00 | | 0.00 | |
| 10308 | Collection 2 | 155.95 | P | 0.00 | | 121.67 | P | 0.00 | | 5.31 | P | 0.00 | | 0.00 | |
| 10503 | Collection 1 | 2.10 | | 4.90 | | 35.36 | | 0.00 | | 2.80 | | 0.00 | | 0.00 | |
| 10503 | Collection 2 | 27.39 | P | 7.10 | P | 46.07 | P | 145.70 | P | 5.80 | P | 0.00 | | 1.70 | P |
| 11003 | Collection 1 | 6.32 | | 10.20 | | 31.11 | | 205.20 | | 5.80 | | 0.00 | | 3.30 | |
| 11003 | Collection 2 | 0.16 | N | 7.30 | N | 25.98 | N | 124.50 | N | 5.40 | N | 0.00 | | 2.80 | N |
| 11601 | Collection 1 | 0.23 | | 0.00 | | 8.10 | | 0.00 | | 8.40 | | 8.00 | | 1.39 | |
| 11601 | Collection 2 | 0.92 | P | 6.00 | P | 12.90 | P | 467.00 | P | 8.80 | P | 8.30 | P | 1.91 | P |
| 11602 | Collection 1 | 1.71 | | 0.00 | | 55.50 | | 0.00 | | 7.50 | | 7.40 | | 0.70 | |
| 11602 | Collection 2 | 1.93 | P | 0.00 | | 11.90 | N | 0.00 | | 5.40 | N | 7.70 | P | 0.88 | P |
| 12121 | Collection 1 | 6.85 | | 0.00 | | 37.40 | | 0.00 | | 7.80 | | 9.00 | | 2.63 | |
| 12121 | Collection 2 | 2.16 | N | 0.00 | | 54.00 | P | 0.00 | | 8.00 | P | 7.40 | N | 0.24 | N |
| 12121 | Collection 3 | 58.64 | P | 0.00 | | 66.30 | P | 0.00 | | 7.90 | P | 7.50 | N | 1.86 | N |
| 190 | Collection 1 | 0.74 | | 0.00 | | 10.80 | | 0.00 | | 5.90 | | 0.00 | | 1.90 | |
| 190 | Collection 2 | 25.18 | P | 0.00 | | 11.50 | P | 0.00 | | 5.70 | N | 0.00 | | 0.00 | N |
| 492 | Collection 1 | 0.66 | | 10.90 | | 13.00 | | 441.80 | | 19.40 | | 0.00 | | 3.11 | |
| 492 | Collection 2 | 91.49 | P | 8.60 | N | 21.00 | P | 355.60 | P | 13.30 | N | 0.00 | | 2.12 | N |
| 2546 | Collection 1 | 4.73 | | 11.55 | | 16.70 | | 299.40 | | 8.00 | | 0.00 | | 3.50 | |
| 2546 | Collection 2 | 28.18 | P | 26.12 | P | 38.80 | P | 912.70 | P | 13.30 | P | 0.00 | | 5.40 | P |

"N" and "P" denote a negative or positive relationship between pairs of observations for each marker, respectively per subject.
Underlined data are number pairs above upper limit of quantitation and are assumed to have a positive relationship.

The following Table C shows that CRP and growth factors can be predictive of mucosal healing:

| Subject ID | Collection Date | CRP | | EGF | | VEGF | | Tweak | | TGF beta1 | |
|---|---|---|---|---|---|---|---|---|---|---|---|
| 2834 | Collection 1 | 6.88 | | 604.22 | | 624.03 | | 2.00 | | 68.05 | |
| 2834 | Collection 2 | 24.33 | P | 631.31 | P | 509.73 | N | 3.72 | P | 44.79 | N |
| 3570 | Collection 1 | 105.46 | | 1046.04 | | 191.49 | | 5.51 | | 33.61 | |
| 3570 | Collection 2 | 1.31 | N | 487.25 | N | 237.91 | P | 6.33 | P | 41.29 | P |
| 3713 | Collection 1 | 7.76 | | 1117.85 | | 1267.74 | | 3.94 | | 45.08 | |
| 3713 | Collection 2 | 107.22 | P | 633.56 | N | 957.18 | N | 5.44 | P | 39.59 | N |
| 5301 | Collection 1 | 7.62 | | | | | | | | 32.19 | |
| 5301 | Collection 2 | 36.61 | P | 217.02 | | 389.33 | | 2.88 | | 30.89 | N |
| 7757 | Collection 1 | 4.49 | | 838.39 | | 11.24 | | 7.90 | | 43.35 | |
| 7757 | Collection 2 | 138.56 | P | 705.18 | N | | | 5.33 | N | | |
| 7966 | Collection 1 | 3.03 | | 120.82 | | 326.72 | | 5.59 | | 38.67 | |
| 7966 | Collection 2 | 31.04 | P | 1089.52 | P | 691.29 | P | 6.81 | P | 48.68 | P |
| 8075 | Collection 1 | 6.81 | | 968.26 | | 840.06 | | 8.10 | | 58.65 | |
| 8075 | Collection 2 | 34.62 | P | 620.97 | N | 876.55 | P | 6.27 | N | 51.36 | N |
| 8127 | Collection 1 | 34.41 | | 323.51 | | 310.67 | | 5.54 | | 41.13 | |
| 8127 | Collection 2 | 2.78 | N | 318.02 | N | 284.46 | N | 6.87 | P | 51.87 | P |
| 8431 | Collection 1 | 4.53 | | 1829.91 | | 214.78 | | 2.18 | | 52.82 | |
| 8431 | Collection 2 | 30.51 | P | 816.10 | N | 301.14 | P | 3.47 | P | 58.41 | P |
| 3831 | Collection 1 | 32.95 | | 804.87 | | 491.46 | | 6.83 | | 36.16 | |
| 3831 | Collection 2 | 0.29 | N | 491.17 | N | 912.29 | P | 7.31 | P | 23.62 | N |
| 3852 | Collection 1 | 68.59 | | 494.06 | | 252.18 | | 6.10 | | 32.76 | |
| 3852 | Collection 2 | 1.00 | N | 291.49 | N | 122.66 | N | 6.56 | P | 39.22 | P |

-continued

| Subject ID | Collection Date | CRP | | EGF | | VEGF | | Tweak | | TGF beta1 | |
|---|---|---|---|---|---|---|---|---|---|---|---|
| 3852 | Collection 3 | 0.60 | N | 375.97 | N | 100.53 | N | 1.34 | N | 22.83 | N |
| 5477 | Collection 1 | 23.17 | | 550.58 | | 485.76 | | 7.51 | | 36.73 | |
| 5477 | Collection 2 | 2.12 | N | 1101.83 | P | 575.69 | P | 7.55 | P | 34.98 | N |
| 7456 | Collection 1 | 35.21 | | 51.23 | | 452.45 | | 6.13 | | 22.05 | |
| 7456 | Collection 2 | 0.89 | N | 496.87 | P | 366.73 | N | 0.99 | N | 14.19 | N |

"N" and "P" denote a negative or positive relationship between pairs of observations for each marker, respectively per subject. Underlined data are number pairs above upper limit of quantitation and are assumed to have a positive relationship.

The following Table D shows that CRP and growth factors can be predictive of mucosal

| Subject ID | Collection Date | CRP | | AREG | | HGF | | HRG | | HB EGF | | BTC | | TGF alpha | |
|---|---|---|---|---|---|---|---|---|---|---|---|---|---|---|---|
| 2834 | Collection 1 | 6.88 | | | | | | | | | | | | | |
| 2834 | Collection 2 | 24.33 | P | | | | | | | | | | | | |
| 3570 | Collection 1 | 105.46 | | | | | | | | | | | | | |
| 3570 | Collection 2 | 1.31 | N | | | | | | | | | | | | |
| 3713 | Collection 1 | 7.76 | | 0.00 | | 17.40 | | 0.00 | | 6.90 | | 0.00 | | 2.20 | |
| 3713 | Collection 2 | 107.22 | P | 0.00 | | 13.20 | N | 0.00 | | 5.80 | N | 0.00 | | 0.00 | N |
| 5301 | Collection 1 | 7.62 | | | | | | | | | | | | | |
| 5301 | Collection 2 | 36.61 | P | | | | | | | | | | | | |
| 7757 | Collection 1 | 4.49 | | 2.60 | | 26.00 | | 0.00 | | 6.90 | | 0.00 | | 6.82 | |
| 7757 | Collection 2 | 138.56 | P | 2.70 | P | 43.00 | P | 0.00 | | 5.70 | N | 0.00 | | 6.82 | P |
| 7966 | Collection 1 | 3.03 | | 4.20 | | 21.00 | | 0.00 | | 6.10 | | 34.58 | | 3.33 | |
| 7966 | Collection 2 | 31.04 | P | 2.40 | N | 36.00 | P | 0.00 | | 5.70 | N | 0.00 | N | 2.62 | N |
| 8075 | Collection 1 | 6.81 | | 8.50 | | 14.70 | | 359.30 | | 8.90 | | 0.00 | | 0.00 | |
| 8075 | Collection 2 | 34.62 | P | 6.40 | N | 16.80 | P | 0.00 | N | 6.30 | N | 0.00 | | 0.00 | |
| 8127 | Collection 1 | 34.41 | | 13.20 | | 16.50 | | 476.30 | | 23.00 | | 16.90 | | 5.28 | |
| 8127 | Collection 2 | 2.78 | N | 9.40 | N | 16.90 | P | 355.30 | P | 9.10 | N | 0.00 | N | 3.46 | N |
| 8431 | Collection 1 | 4.53 | | 5.00 | | 21.40 | | 0.00 | | 5.50 | | 0.00 | | 0.00 | |
| 8431 | Collection 2 | 30.51 | P | 31.30 | P | 24.80 | P | 671.90 | P | 23.10 | P | 0.00 | | 25.00 | P |
| 3831 | Collection 1 | 32.95 | | | | | | | | | | | | | |
| 3831 | Collection 2 | 0.29 | N | | | | | | | | | | | | |
| 3852 | Collection 1 | 68.59 | | 0.00 | | 17.08 | | 0.00 | | 6.00 | | 0.00 | | 0.00 | |
| 3852 | Collection 2 | 1.00 | N | 0.00 | | 13.84 | N | 0.00 | | 5.10 | N | 0.00 | | 0.00 | |
| 3852 | Collection 3 | 0.60 | N | | | | | | | | | | | | |
| 5477 | Collection 1 | 23.17 | | 2.30 | | 15.25 | | 143.20 | | 5.60 | | 0.00 | | 0.00 | |
| 5477 | Collection 2 | 2.12 | N | 2.00 | N | 19.05 | P | 0.00 | N | 5.40 | N | 0.00 | | 2.50 | P |
| 7456 | Collection 1 | 35.21 | | 16.70 | | 0.00 | | 315.30 | | 8.10 | | 0.00 | | 5.10 | |
| 7456 | Collection 2 | 0.89 | N | 6.60 | N | 12.92 | P | 128.90 | N | 3.60 | N | 0.00 | | 2.70 | N |

"N" and "P" denote a negative or positive relationship between pairs of observations for each marker, respectively per subject. Underlined data are number pairs above upper limit of quantitation and are assumed to have a positive relationship.

Tables A, B, C and D show marker values and relationships between pairs of observations in CRP and growth factor data. Using a criterion of $\alpha=0.1$, we identified an association between three growth factors and CRP. The following Table (E) shows a two-by-two contingency table that highlights that an increase or decrease in AREG, HRG and TGF was found to be significantly associated with an increase or decrease of CRP:

| | | AREG* | | HRG** | | TGF-alpha*** | |
|---|---|---|---|---|---|---|---|
| | | Positive | Negative | Positive | Negative | Positive | Negative |
| CRP | Positive | 6 | 4 | 7 | 1 | 8 | 5 |
| | Negative | 0 | 6 | 1 | 5 | 1 | 6 |

*denotes p = 0.034.
**denotes p = 0.026.
***denotes p = 0.07.

Figure 22:
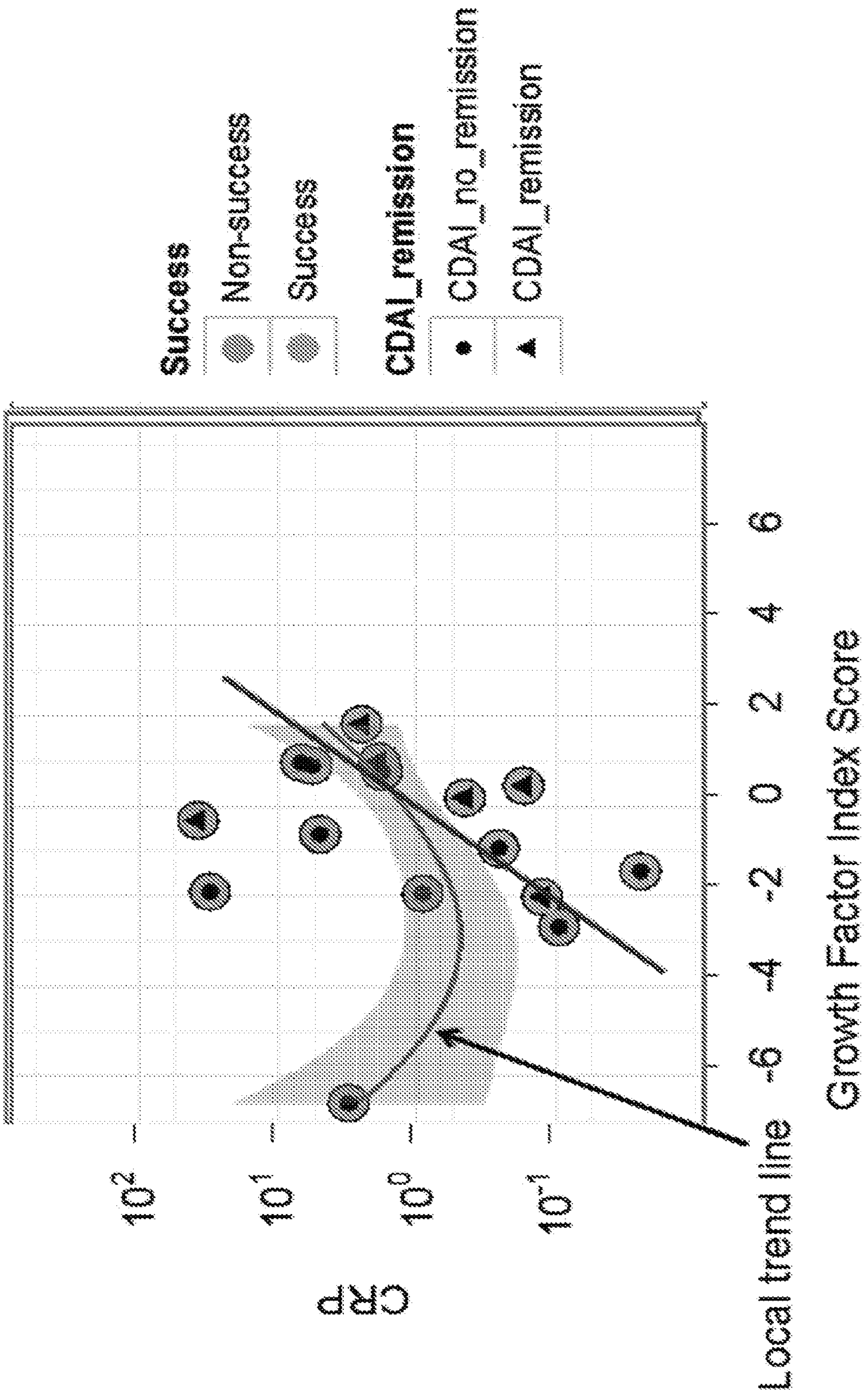
FIG. 22 illustrates the association between CRP levels and the growth factor index score in determining disease remission.

FIG. 22 illustrates the association between CRP levels and the growth factor index score in determining disease remission.

Further studies for identifying predictive markers of mucosal healing may include samples from several clinical studies. As one non-limiting example, Clinical Study A may include 413 samples (paired samples with 1-5 samples per patient). Clinical data may detail patient age, sex, weight, date of diagnosis, disease location, sample collection dates, dose, colonoscopy, improvement of mucosa, presence of mucosal healing, and/or concomitant medication usage. In Clinical Study A, colonoscopy may be performed prior to first drug infusion. As another non-limiting example, in Clinical Study B, 212 UC samples may be analyzed (110 samples were diagnosed for CD at follow-up and 102 samples were diagnosed for UC based on mucosal healing). Clinical data may detail patient age, sex, weight, date of diagnosis, disease location, sample collection dates, IFX dose, colonoscopy results (endoscopic activity score), albumin level, CRP level, and/or Mayo score. In Clinical Studies A and B, three infusions may occur at week 0, 2 and 6 during induction. 6 additional drug infusions may be performed during the maintenance phase at week 14, 22, 30, 38, 46 and 52. A second colonoscopy may be performed during the maintenance phase. A third colonoscopy may be performed during follow-up and patients may continue treatment if responsive to drug.

Figure 23A:
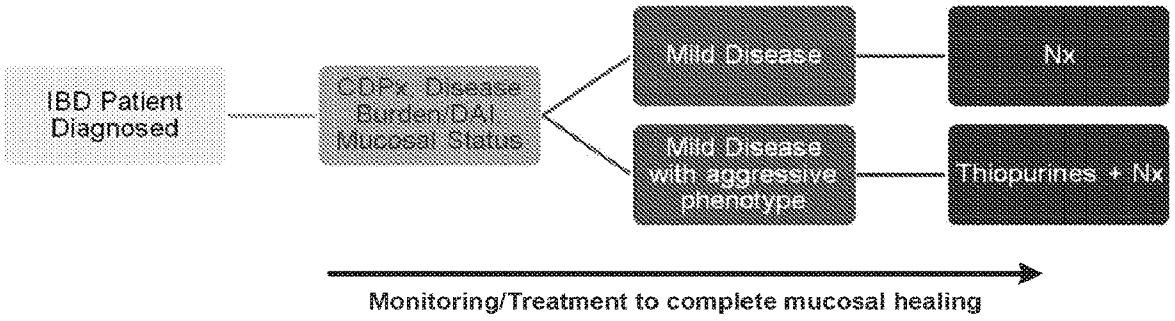
FIGS. 23A-C illustrate embodiments of the present invention to assist in developing personalized patient treatment for an IBD patient with mild, moderate, or severe disease activity.
Figure 23B:
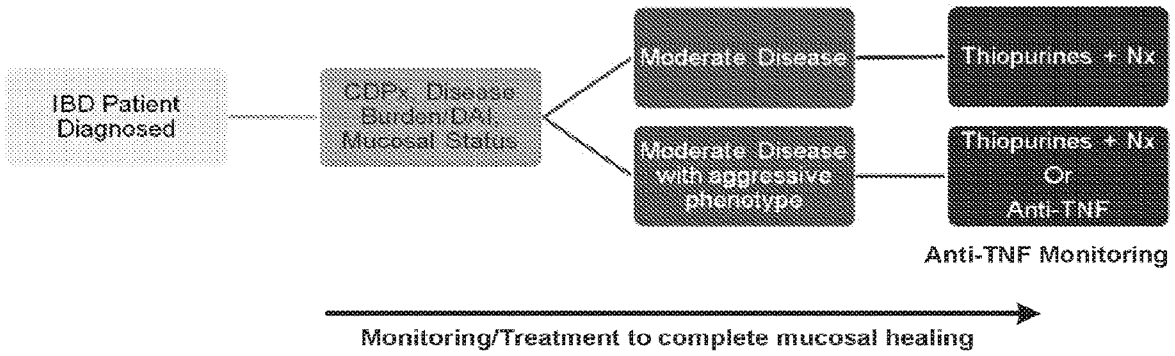
Figure 23C:
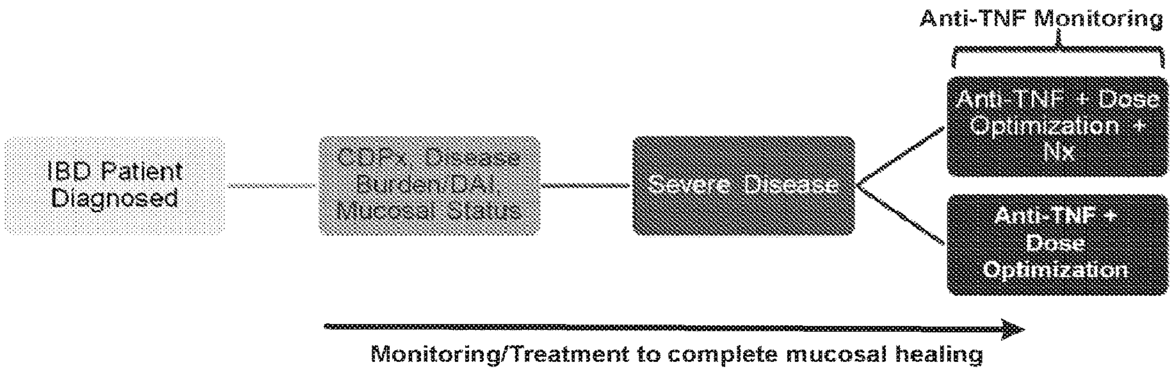

The methods of the present invention can be used to create personalized therapeutic management of a TNFα-mediated disease. A personalized therapeutic regimen for a patient diagnosed with IBD can be selected based on predictors of disease status and/or long-term outcome as described herein, including, but not limited to, a Crohn's prognostic test (see, e.g., PCT Publication No. WO 2010/120814, the disclosure of which is hereby incorporated by reference in its entirety for all purposes), a disease activity profile (e.g., disease burden), a mucosal status index, and/or a PRO Inflammatory Index as described in Example 5. Using the methods of the present invention, it can be determined that a patient has mild disease activity and the clinician can recommend, prescribe, and/or administer a nutrition-based therapy (FIG. 23A). Yet, if it is determined that a patient has mild disease activity with an aggressive phenotype, a nutrition-based therapy in addition to thiopurines can be recommended, prescribed, and/or administered. A similar therapy can be recommended, prescribed, and/or administered if it is determined that the patient has moderate disease activity (FIG. 23B). If it is determined that a patient has moderate disease activity with an aggressive phenotype, either a combination of thiopurines and nutrition therapy (Nx) or an appropriate anti-TNF drug can be recommended, prescribed, and/or administered. In some instances, an anti-TNF monitoring test (see, e.g., PCT Publication No. WO 2011/056590, the disclosure of which is hereby incorporated by reference in its entirety for all purposes) can be used to determine if the patient is likely to respond to the therapy. In the case when severe disease activity is determined, an appropriate anti-TNF drug administered at an optimized dose can be recommended and/or prescribed (FIG. 23C). In such instances, an anti-TNF monitoring test (see, e.g., PCT Publication No. WO 2011/056590, the disclosure of which is hereby incorporated by reference in its entirety for all purposes) can be used to predict if the patient is likely to be responsive to drug. In other instances, it can be recommended and/or prescribed that a patient having severe disease activity also receive nutrition-based therapy.

Figure 24:
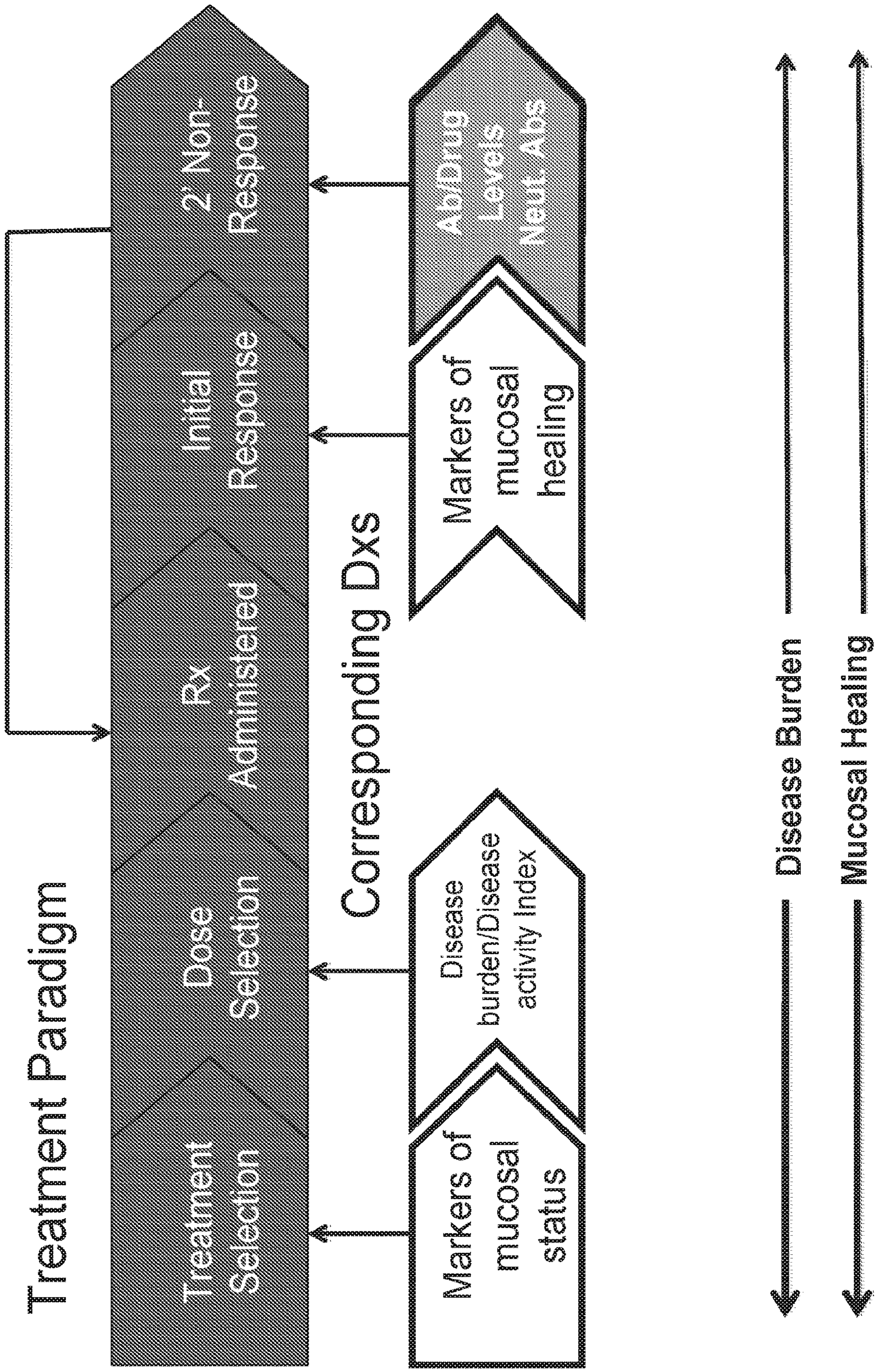
FIG. 24 illustrates a treatment paradigm to personalize patient treatment. Monitoring of disease burden and mucosal healing can assist in determining treatment selection, dose selection, and initial drug response.

In some embodiments, the methods of the present invention can be used in a treatment paradigm to personalize patient treatment (FIG. 24). First, treatment can be selected based on the expression of mucosal status markers. Next, drug dose can be selected based on disease burden (e.g., disease activity index). After the therapeutic drug is administered, the initial response can be determined from the expression of markers of mucosal healing. ATM monitoring can be used to identify patient who are responsive or non-responsive to therapy. Non-responsive patients can then be prescribed an appropriate anti-TNF drug.

Example 11. Novel Infliximab (IFX) and Antibody-to-Infliximab (ATI) Assays are Predictive of Disease Activity in Patients with Crohn's Disease (CD)

Previous studies indicate that patients with CD who have a higher trough concentration of IFX during maintenance dosing are more likely to benefit from treatment. However, development of ATIs can result in increased drug clearance and loss of response. Therapeutic drug monitoring may allow clinicians to maintain effective drug concentrations. Although previous ATI assays have been limited by the inability to measure ATIs in the presence of drug, fluid-phase IFX and ATI assays have overcome this problem (see, e.g., PCT Publication No. WO 2011/056590, the disclosure of which is hereby incorporated by reference in its entirety for all purposes). We used these assays to evaluate the relationship between serum IFX concentration, ATIs and disease activity.

Methods: 2021 serum samples from 532 participants in 4 prospective CD RCTs or cohort studies (COMMIT, Leuven dose optimization study, Canadian Multicenter and IMEDEXI) that evaluated the maintenance phase of IFX treatment were used, and data were combined for analysis. IFX and ATI serum levels were measured using a HPLC-based fluid phase assay. CRP, measured by ELISA, was used to assess disease activity. ROC analysis determined the IFX threshold that best discriminated disease activity, as measured by CRP. We examined pairs of samples taken over sequential time points and evaluated the relationship between IFX and ATI presence in the pair's first data point and CRP in the subsequent measurement. There were 1205 such observations. We identified four distinct patient groups, namely IFX≥threshold and ATI−, IFX<threshold and ATI−, IFX≥threshold and ATI+, and IFX<threshold and ATI+. Regression analyses assessed the potential interaction between IFX and ATI as predictors of CRP.

Results: CRP can best differentiate IFX status with an IFX concentration threshold of 3 μg/ml (ROC AUC=74%). Using paired sequential samples both ATI and IFX were associated with median CRP (Table 2). Although ATI+ patients had higher CRP levels overall, within this group there was no association between IFX higher than threshold and subsequent CRP. In ATI− patients, CRP was significantly higher in patients with IFX levels <3 μg/ml. In the regression analysis ATI positivity, IFX≥3 μg/ml and the interaction term were all significant predictors of CRP. CRP was 31% higher in ATI positive patients than those who were ATI negative and 62% lower in patients with IFX levels ≥3 μg/ml compared to those with IFX<3 μg/ml.

Conclusions: We have shown that ATI positivity is predictive of increased disease activity, while an IFX concentration above the threshold value of 3 μg/ml is predictive of significantly lower disease activity. In ATI+ patients, IFX concentrations above 3 g/ml had no effect on CRP, indicating that the benefits of IFX are diminished in the presence of ATI despite the presence of optimal drug concentration. These findings support the concept that therapeutic drug monitoring is an important tool in optimizing IFX therapy. Using paired sequential samples and regression analysis, both ATI and IFX were associated with median CRP as shown in the following table:

| | Median CRP Concentration (ng/ml; interquartile range) | | |
|---|---|---|---|
| | In ATI− Patients | In ATI+ Patients | Significance |
| IFX < 3 μg/ml | 5.65 (1.68, 16.1) | 8.40 (3.10, 20.1) | *** |
| IFX ≥ 3 μg/ml | 1.50 (1.00, 4.70) | 9.90 (5.82, 20.2) | ** |
| Significance | *** | NS | |

Median CRP concentrations and interquartile ranges (in parentheses) in ng/ml.
Asterisks denote significance levels of two-sample Mann-Whitney U tests (*, $p < 0.001$; , $p < 0.01$; *, $p < 0.05$; NS, not significant).

Example 12. Novel Infliximab (IFX) and Antibody-to-Infliximab (ATI) Assays are Predictive of Disease Activity in Patients with Crohn's Disease (CD)

This example illustrates the use of infliximab (IFX) and antibody-to-infliximab (ATI) assay in predicting disease activity in patients with Crohn's disease (CD). This example also illustrates a method of determining the threshold of IFX that can best discriminate disease activity as measured by C-reactive protein (CRP) levels. This example also illustrates the association of both ATI and IFX to CD and CRP levels, which can serve as a measure of disease activity.

Previous studies have indicated that patients with CD who have a higher trough concentration of IFX during maintenance dosing are more likely to benefit from treatment. However, development of ATIs can result in increased drug clearance and loss of response. Therapeutic drug monitoring may allow clinicians to maintain effective drug concentrations. Although previous ATI assays have been limited by the inability to measure ATIs in the presence of drug, the fluid-phase IFX and ATI assays described in PCT Publication No. WO 2011/056590 (the disclosure of which is hereby incorporated by reference in its entirety for all purposes) have overcome this problem.

In this study we used fluid-phase IFX and ATI assays to evaluate the relationship between serum IFX concentration, ATIs and disease activity, as measured by CRP. We analyzed 2,021 serum samples from 532 participants in 4 prospective CD randomized controlled trials (RCTs) or cohort studies, including COMMIT, Leuven dose optimization study, Canadian Multicenter and AIEDEXl. The combined analysis was restricted to samples during maintenance of IFX treatment. There was evidence of non-heterogeneity among pooled CRP.

Figure 25:
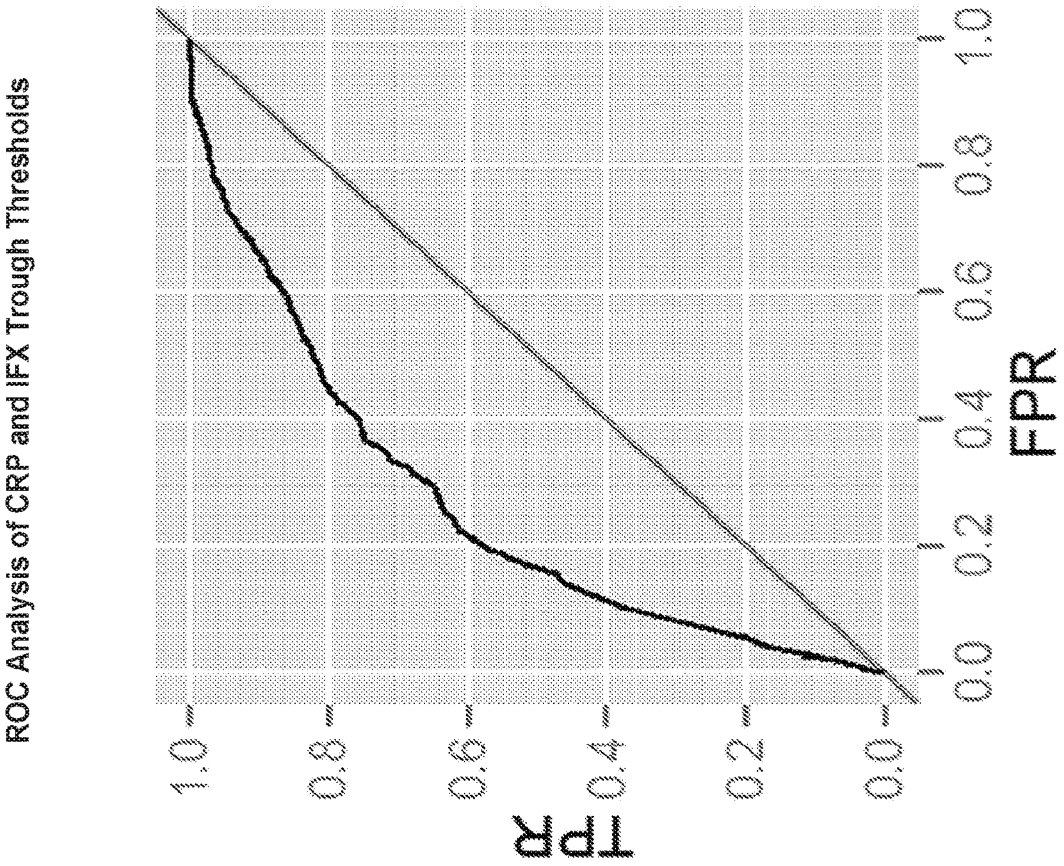
FIG. 25 shows the ROC analysis of CRP and IFX trough thresholds.

IFX and ATI serum levels were measured using a HPLC-based fluid phase assay. CRP was measured by ELISA and used to assess disease activity. Receiver-operator curve (ROC) analysis was performed to determine the IFX trough threshold (e.g., amount or concentration) that can best discriminate disease activity (e.g., between high and low CRP values). FIG. 25 shows the ROC analysis. CRP and nine IFX trough thresholds were analyzed and the ROC area under receiver-operator characteristic curve (AUC) are as follows:

| | IFX trough threshold (μg/ml) | | | | | | | | |
|---|---|---|---|---|---|---|---|---|---|
| | 0.1 | 1.0 | 2.0 | 3.0 | 4.0 | 5.0 | 6.0 | 7.0 | 8.0 |
| ROC AUC | 0.682 | 0.727 | 0.733 | 0.743 | 0.727 | 0.717 | 0.699 | 0.689 | 0.678 |

The ROC analysis showed that CRP can best differentiate IFX status with an IFX concentration threshold of 3 μg/ml (ROC AUC=74%). For example, at an IFX through concentration threshold of 3.0 μg/ml, a randomly chosen sample with a "low" IFX serum concentration will have a higher CRP level than a randomly chosen sample with a "high" IFX serum concentration 74.3% of the time. In the IFX, ATI and CRP association analysis, a serum IFX trough threshold of 3.0 μg/ml was used.

Figure 26A:
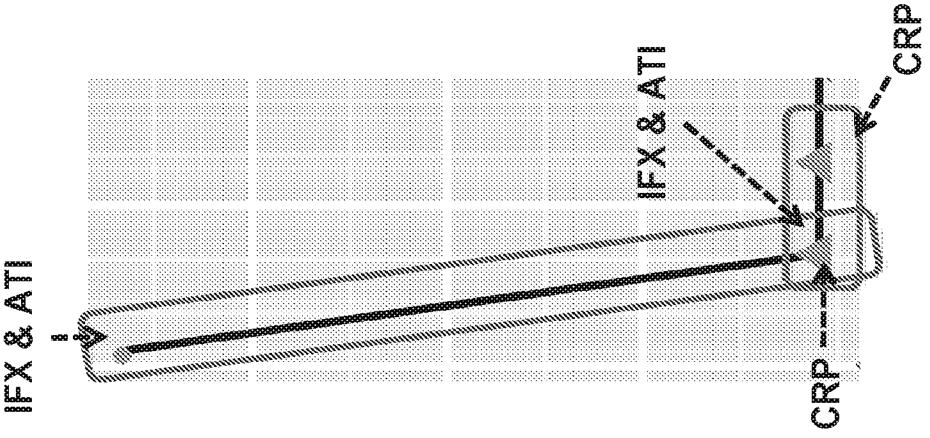
FIGS. 26A-B show the relationship of CRP, serum IFX concentration and ATI at sequential time points.
Figure 26B:
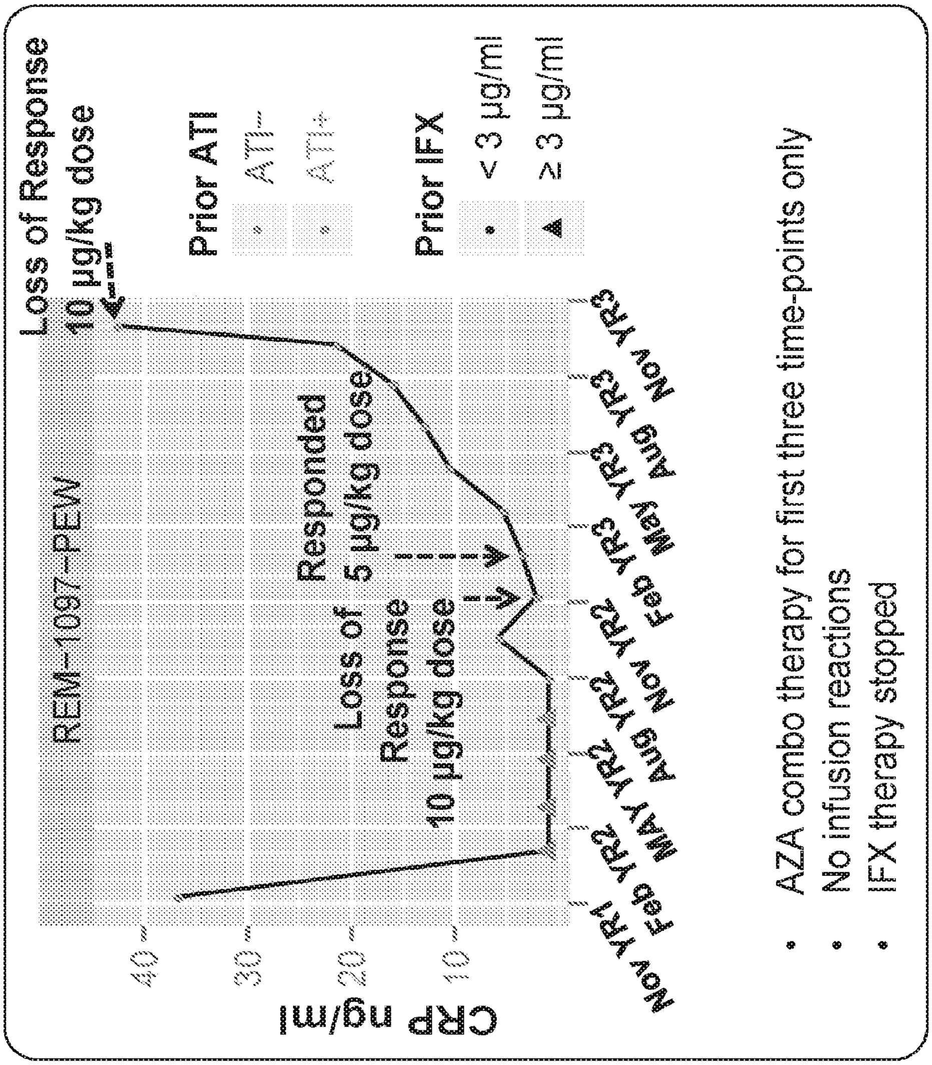

To determine the association of serum IFX concentration, ATI, and CRP levels over time, we examined pairs of samples taken over sequential time points. A 100-day time gap limit was imposed for the time points. We evaluated the relationship between the presence of IFX and ATI in the pair's first data point and CRP in the subsequent measurements (FIG. 26A). FIG. 26B shows CRP levels, IFX serum concentration and ATI status at sequential time points for a sample. In total, 1,205 observations were examined.

Regression analysis (e.g., ordinary least squares regression) was performed to assess the potential interaction between prior IFX and prior ATI as predictors of disease (i.e., CRP levels). In particular, CRP was log transformed at the second time point observation. Prior IFX is the first time point with IFX concentration above or below the calculated trough threshold of 3 μg/ml. Prior ATI is the first time point ATI is above or below 3.13 U/ml which is the limit of detection (LOD). Using paired sequential samples and regression analysis, both ATI and IFX were associated with median CRP as shown in the following table:

| | Median CRP Concentration (ng/ml; interquartile range) | | |
|---|---|---|---|
| | In ATI− Patients | In ATI+ Patients | Significance |
| IFX < 3 μg/ml | 5.65 (1.68, 16.1) | 8.40 (3.10, 20.1) | *** |
| IFX ≥ 3 μg/ml | 1.50 (1.00, 4.70) | 9.90 (5.82, 20.2) | ** |
| Significance | *** | NS | |

Median CRP concentrations and interquartile ranges (in parentheses) in ng/ml.
Asterisks denote significance levels of two-sample Mann-Whitney U tests (*, $p < 0.001$; , $p < 0.01$; *, $p < 0.05$; NS, not significant).

The results shows that the factors and interactions between the factors are significant. The regression coefficients were calculated to be 0.272 for ATI+ samples and −0.979 for IFX≥3 μg/ml.

We identified four distinct patient groups: (1) IFX≥threshold and ATI−, (2) IFX<threshold and ATI−, (3) IFX≥threshold and ATI+, and (4) IFX<threshold and ATI+. Of the 1,205 observations used in the analysis, 605 were IFX≥threshold and ATI−; 196 were IFX<threshold and ATI−; 41 were IFX≥threshold and ATI+; and 363 were IFX<threshold and ATI+.

Figure 27:
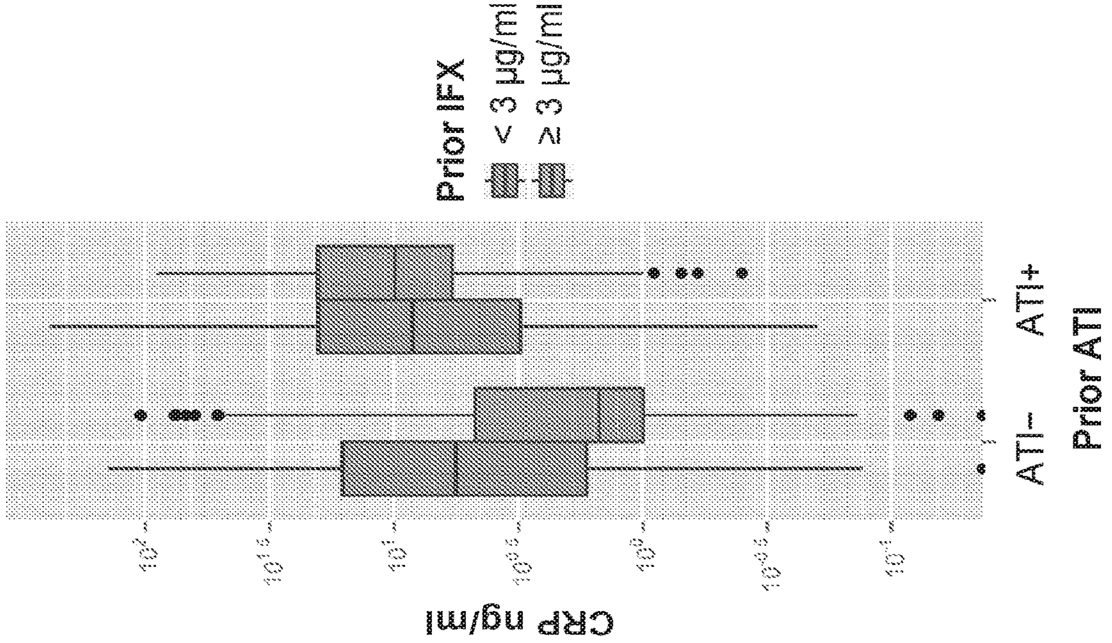
FIG. 27 shows that there was no association between IFX levels higher than threshold and CRP in ATI+ patients. Yet, in ATI− patients CRP levels were significantly higher in patients with IFX levels less than threshold (3 μg/ml).

Although ATI+ patients had higher CRP levels overall, within this group there was no association between IFX levels higher than threshold and CRP (FIG. 27). In ATI-patients, CRP levels were significantly higher in patients with IFX levels less than threshold (FIG. 27).

In the regression analysis, ATI positivity, IFX≥3 μg/ml and their interaction were all significant predictors of CRP levels. CRP was 31% higher in ATI+ patients than those who were ATI−, and 62% lower in patients with IFX levels ≥3 μg/ml compared to those with IFX<3 μg/ml. The relationship between IFX concentration and CRP levels differs between ATI+ and ATI− patient groups.

In this study we showed that ATI positivity is predictive of increased disease activity, as measured by CRP. We also showed that IFX concentration above the threshold value of 3 μg/ml is predictive of significantly lower disease activity. In ATI+ patients, IFX concentrations above 3 μg/ml had no effect on CRP levels, suggesting that the benefits of IFX are diminished in the presence of ATI even despite the presence of optimal drug concentration.

We showed that disease activity, as measured by CRP, is strongly linked to both IFX and ATI in a large combined dataset. Thus, patients with active Crohn's disease can benefit from knowledge of both IFX and ATI levels at trough. Based on the experimental derivation of these relationships, the following treatment paradigms were created. For instance, a symptomatic patient with Crohn's disease with IFX<threshold at trough and ATI− can benefit from an increased dose of IFX therapy. A patient with IFX≥threshold and ATI− can benefit from receiving endoscopy or switching therapy. A symptomatic patient with IFX<threshold at trough and ATI+ can benefit from switching therapy if ATI is high or optimizing therapy dose if ATI is low. A patient with IFX≥threshold and ATI+ can benefit from switching therapy if disease activity (e.g., CRP level) is high. Alternatively, if disease activity (e.g., CRP level) is low in that patient, further monitoring is recommended. The treatment paradigms are described in the following table:

| | ATI− | ATI+ |
|---|---|---|
| IFX < threshold | Increase dose | Switch therapy (high ATI) or Optimize dose (low ATI) |
| IFX ≥ threshold | Check endoscopy or Switch therapy | Switch therapy (high activity) or Monitor (low activity) |

These findings demonstrate that therapeutic drug monitoring using methods of the present invention are important tools in optimizing IFX therapy.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each as individually incorporated by reference.

What is claimed is:

1. A method of treating Ulcerative Colitis (UC) in a subject, the method comprising: administering a therapeutically effective amount of a therapeutic agent to the subject to treat the UC, based, at least partially, on a Mucosal Healing Index (MHI) score of the subject calculated by applying a statistical algorithm to levels of mucosal healing markers measured in a sample obtained from the subject to generate a MHI, and comparing the MHI to an endoscopic score, wherein the therapeutic agent comprises a TNFα inhibitor therapy, an immunosuppressive agent, a corticosteroid, an IL-6 receptor inhibiting antibody, an anti-integrin molecule, a JAK-2 inhibitor, a tyrosine kinase inhibitor, nutrition therapy, or combinations thereof.

2. The method of claim 1, wherein the TNFα inhibitor therapy comprises an anti-TNFα antibody.

3. The method of claim 2, wherein the anti-TNFα antibody comprises REMICADE™ (infliximab), ENBREL™ (etanercept), HUMIRA™ (adalimumab), CIMZIA® (certolizumab pegol), or any combination thereof.

4. The method of claim 1, wherein the immunosuppressive agent comprises azathioprine, 6-mercaptopurine, methotrexate, or any combination thereof.

5. The method of claim 1, wherein the nutrition therapy comprises a special carbohydrate diet.

6. The method of claim 1, wherein the mucosal healing markers are measured in a sample selected from the group consisting of serum, plasma, whole blood, stool, peripheral blood mononuclear cells (PBMC), polymorphonuclear (PMN) cells, and a tissue biopsy.

7. The method of claim 1, wherein the mucosal healing markers comprise AREG, EREG, HB-EGF, HGF, NRG1, NRG2, NRG3, NRG4, BTC, EGF, IGF, TGF-α, VEGF-A, VEGF-B, VEGF-C, VEGF-D, FGF1, FGF2, FGF7, FGF9, TWEAK or combinations thereof.

8. The method of claim 1, wherein the mucosal healing markers comprise an anti-TNFα antibody, an anti-drug antibody (ADA), an inflammatory marker, an anti-inflammatory marker, or combinations thereof.

9. The method of claim 8, wherein the anti-TNFα antibody comprises REMICADE™ (infliximab), ENBREL™ (etanercept), HUMIRA™ (adalimumab), CIMZIA® (certolizumab pegol), or any combination thereof.

10. The method of claim 8, wherein the anti-drug antibody (ADA) comprises a human anti-chimeric antibody (HACA), a human anti-humanized antibody (HAHA), a human anti-mouse antibody (HAMA), or any combination thereof.

11. The method of claim 8, wherein the inflammatory marker comprises GM-CSF, IFN-γ, IL-1B, IL-2, IL-6, IL-8, TNF-α, sTNF RII, or any combination thereof.

12. The method of claim 8, wherein the anti-inflammatory marker comprises IL-12p70, IL-10, or any combination thereof.

13. The method of claim 1, wherein:

(i) the mucosal healing markers comprise GM-CSF, IFN-γ, IL-1β, IL-2, IL-6, IL-8, TNF-α, soluble tumor necrosis factor-α receptor II (sTNF RII), TNF-related weak inducer of apoptosis (TWEAK), osteoprotegerin (OPG), IFN-α, IFN-β, IL-1α, IL-1 receptor antagonist (IL-1ra), IL-4, IL-5, soluble IL-6 receptor (sIL-6R), IL-7, IL-9, IL-12, IL-13, IL-15, IL-17, IL-23, IL-27, or any combination thereof;

(ii) the mucosal healing markers comprise MMP-1, MMP-2, MMP-3, MMP-7, MMP-8, MMP-9, MMP-12, MMP-13, MT1-MMP-1, or any combination thereof; or (iii) the mucosal healing markers comprise C-reactive protein (CRP), D-dimer protein, mannose-binding protein, alpha 1-antitrypsin, alpha 1-antichymotrypsin, alpha 2-macroglobulin, fibrinogen, prothrombin, factor VIII, von Willebrand factor, plasminogen, complement factors, ferritin, serum amyloid P component, serum amyloid A (SAA), orosomucoid (alpha 1-acid glycoprotein (AGP)), ceruloplasmin, haptoglobin, or any combination thereof;

(iv) the mucosal healing markers comprise TGF-α, TGF-β, TGF-2, TGF-β3, or any combination thereof; or (v) the mucosal healing markers comprise AREG, EREG, HB-EGF, HGF, HRG, NRG1, NRG2, NRG3, NRG4, BTC, EGF, IGF-1, TGF, VEGF-A, VEGF-B, VEGF-C, VEGF-D, FGF1, FGF2, FGF7, FGF9, TWEAK, or any combination thereof; or (vi) the mucosal healing markers comprise IL-10, SCF, ICAM, VCAM, IL-12p40, VEGFA, or any combination thereof.

14. The method of claim 9, wherein the mucosal healing markers comprise C-reactive protein (CRP), IL 7, MMP 1, MMP 2, MMP 3, MMP 9, serum amyloid A (SAA), TGFα, VCAM, or any combination thereof.

15. The method of claim 1, wherein the subject has rheumatoid arthritis.

16. The method of claim 1, further comprising calculating a second MHI score for the subject following the administration of the therapeutically effective amount of the therapeutic agent to the subject to treat the UC.

17. The method of claim 1, further comprising administering the therapeutically effective amount of the therapeutic agent to the subject again.

18. The method of claim 1, further comprising predicting whether the subject will respond to the TNFα inhibitor therapy.

* * * * *